US012605571B2

(12) United States Patent
Wiener et al.

(10) Patent No.: US 12,605,571 B2
(45) Date of Patent: Apr. 21, 2026

(54) SURGICAL INSTRUMENTS

(71) Applicant: Cilag GmbH International, Zug (CH)

(72) Inventors: Eitan T. Wiener, Cincinnati, OH (US);
Kenneth S. Kramer, Trabuco Canyon,
CA (US); Ashvani K. Madan, Mason,
OH (US); Kevin L. Houser,
Springboro, OH (US)

(73) Assignee: Cilag GmbH International, Zug (CH)

( * ) Notice: Subject to any disclaimer, the term of this
patent is extended or adjusted under 35
U.S.C. 154(b) by 371 days.

(21) Appl. No.: 18/206,391

(22) Filed: Jun. 6, 2023

(65) Prior Publication Data

US 2023/0390591 A1 Dec. 7, 2023

Related U.S. Application Data

(63) Continuation of application No. 16/539,122, filed on
Aug. 13, 2019, now Pat. No. 11,666,784, which is a
(Continued)

(51) Int. Cl.
*A61N 7/02* (2006.01)
*A61B 17/00* (2006.01)
(Continued)

(52) U.S. Cl.
CPC ........ *A61N 7/02* (2013.01); *A61B 17/320068*
(2013.01); *A61B 17/320092* (2013.01);
(Continued)

(58) Field of Classification Search
CPC .... A61B 17/320068; A61B 17/320092; A61B
2017/00084; A61B 2017/00106; A61B
2017/00128
See application file for complete search history.

(56) References Cited

U.S. PATENT DOCUMENTS

| | | | |
|---|---|---|---|
| 969,528 | A | 9/1910 | Disbrow |
| 1,570,025 | A | 1/1926 | Young |

(Continued)

FOREIGN PATENT DOCUMENTS

| | | | |
|---|---|---|---|
| AU | 2003241752 A1 | 9/2003 | |
| CA | 837241 A | 3/1970 | |

(Continued)

OTHER PUBLICATIONS

Technology Overview, printed from www.harmonicscalpel.com,
Internet site, website accessed on Jun. 13, 2007, (3 pages).
(Continued)

*Primary Examiner* — Ashley L Fishback

(57) ABSTRACT

A surgical device. The surgical device may comprise a
transducer, an end effector, a generator and a control circuit.
The transducer may be configured to provide vibrations. The
end effector may be coupled to the transducer and may
extend from the transducer along the longitudinal axis. The
generator may provide an electrical signal to the transducer.
Also, the control circuit may modify a current amplitude of
the electrical signal in response to a change in a vibration
frequency of the end effector. Accordingly to various
embodiments, the control circuit may detect a first contri-
bution to a vibration frequency of the end effector, the first
contribution originating from tissue in contact with the end
effector. Also, according to various embodiments, the con-
trol circuit may indicate a change in a vibration frequency of
the end effector.

18 Claims, 18 Drawing Sheets

Related U.S. Application Data continuation of application No. 15/257,385, filed on Sep. 6, 2016, now Pat. No. 10,420,579, which is a continuation of application No. 13/923,954, filed on Jun. 21, 2013, now Pat. No. 9,445,832, which is a continuation of application No. 11/888,222, filed on Jul. 31, 2007, now Pat. No. 8,512,365.

(51) Int. Cl.
  *A61B 17/32*     (2006.01)
  *A61B 18/00*     (2006.01)

(52) U.S. Cl.
  CPC .............. *A61B 2017/00084* (2013.01); *A61B 2017/00106* (2013.01); *A61B 2017/00128* (2013.01); *A61B 2017/00353* (2013.01); *A61B 2017/320069* (2017.08); *A61B 2017/320071* (2017.08); *A61B 2017/320089* (2017.08); *A61B 2017/320094* (2017.08); *A61B 2017/320095* (2017.08); *A61B 2018/00607* (2013.01); *A61B 2018/00642* (2013.01); *A61B 2018/00791* (2013.01)

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,743,726 A | 5/1956 | Grieshaber |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,503,396 A | 3/1970 | Pierie et al. |
| 3,503,397 A | 3/1970 | Fogarty et al. |
| 3,503,398 A | 3/1970 | Fogarty et al. |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatolan et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,792,701 A | 2/1974 | Kloz et al. |
| 3,805,787 A | 4/1974 | Banko |
| 3,809,977 A | 5/1974 | Balamuth et al. |
| 3,830,098 A | 8/1974 | Antonevich |
| 3,832,776 A | 9/1974 | Sawyer |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,057,660 A | 11/1977 | Yoshida et al. |
| 4,058,126 A | 11/1977 | Leveen |
| 4,074,719 A | 2/1978 | Semm |
| 4,085,893 A | 4/1978 | Durley, III |
| 4,156,187 A | 5/1979 | Murry et al. |
| 4,167,944 A | 9/1979 | Banko |
| 4,169,984 A | 10/1979 | Paris |
| 4,173,725 A | 11/1979 | Asal et al. |
| 4,188,927 A | 2/1980 | Harris |
| 4,193,009 A | 3/1980 | Durley, III |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,281,785 A | 8/1981 | Brooks |
| 4,300,083 A | 11/1981 | Heiges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,352,459 A | 10/1982 | Berger et al. |
| 4,445,063 A | 4/1984 | Smith |
| 4,452,473 A | 6/1984 | Ruschke |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,663,677 A | 5/1987 | Griffith et al. |
| 4,674,502 A | 6/1987 | Imonti |
| 4,696,667 A | 9/1987 | Masch |
| 4,708,127 A | 11/1987 | Abdelghani |
| 4,712,722 A | 12/1987 | Hood et al. |
| 4,735,603 A | 4/1988 | Goodson et al. |
| 4,750,488 A | 6/1988 | Wuchinich et al. |
| 4,761,871 A | 8/1988 | O'Connor et al. |
| 4,783,997 A | 11/1988 | Lynnworth |
| 4,808,154 A | 2/1989 | Freeman |
| 4,819,635 A | 4/1989 | Shapiro |
| 4,821,719 A | 4/1989 | Fogarty |

(56) References Cited

U.S. PATENT DOCUMENTS

| | | | |
|---|---|---|---|
| 4,827,911 | A | 5/1989 | Broadwin et al. |
| 4,830,462 | A | 5/1989 | Karny et al. |
| 4,832,683 | A | 5/1989 | Idemoto et al. |
| 4,836,186 | A | 6/1989 | Scholz |
| 4,838,853 | A | 6/1989 | Parisi |
| 4,844,064 | A | 7/1989 | Thimsen et al. |
| 4,849,133 | A | 7/1989 | Yoshida et al. |
| 4,850,354 | A | 7/1989 | McGurk-Burleson et al. |
| 4,852,578 | A | 8/1989 | Companion et al. |
| 4,860,745 | A | 8/1989 | Farin et al. |
| 4,862,890 | A | 9/1989 | Stasz et al. |
| 4,865,159 | A | 9/1989 | Jamison |
| 4,867,157 | A | 9/1989 | McGurk-Burleson et al. |
| 4,869,715 | A | 9/1989 | Sherburne |
| 4,878,493 | A | 11/1989 | Pasternak et al. |
| 4,880,015 | A | 11/1989 | Nierman |
| 4,881,550 | A | 11/1989 | Kothe |
| 4,896,009 | A | 1/1990 | Pawlowski |
| 4,903,696 | A | 2/1990 | Stasz et al. |
| 4,910,389 | A | 3/1990 | Sherman et al. |
| 4,915,643 | A | 4/1990 | Samejima et al. |
| 4,920,978 | A | 5/1990 | Colvin |
| 4,922,902 | A | 5/1990 | Wuchinich et al. |
| 4,936,842 | A | 6/1990 | D'Amelio et al. |
| 4,954,960 | A | 9/1990 | Lo et al. |
| 4,965,532 | A | 10/1990 | Sakural |
| 4,978,067 | A | 12/1990 | Berger et al. |
| 4,979,952 | A | 12/1990 | Kubota et al. |
| 4,981,756 | A | 1/1991 | Rhandhawa |
| 4,983,160 | A | 1/1991 | Steppe et al. |
| 5,013,956 | A | 5/1991 | Kurozumi et al. |
| 5,015,227 | A | 5/1991 | Broadwin et al. |
| 5,020,514 | A | 6/1991 | Heckele |
| 5,026,370 | A | 6/1991 | Lottick |
| 5,026,387 | A | 6/1991 | Thomas |
| 5,035,695 | A | 7/1991 | Weber, Jr. et al. |
| 5,042,461 | A | 8/1991 | Inoue et al. |
| 5,042,707 | A | 8/1991 | Taheri |
| 5,047,043 | A | 9/1991 | Kubota et al. |
| 5,057,119 | A | 10/1991 | Clark et al. |
| 5,058,570 | A | 10/1991 | Idemoto et al. |
| 5,059,210 | A | 10/1991 | Clark et al. |
| 5,061,269 | A | 10/1991 | Muller |
| 5,084,052 | A | 1/1992 | Jacobs |
| 5,088,687 | A | 2/1992 | Stender |
| 5,096,532 | A | 3/1992 | Neuwirth et al. |
| 5,099,840 | A | 3/1992 | Goble et al. |
| 5,104,025 | A | 4/1992 | Main et al. |
| 5,105,117 | A | 4/1992 | Yamaguchi |
| 5,106,538 | A | 4/1992 | Barma et al. |
| 5,108,383 | A | 4/1992 | White |
| 5,109,819 | A | 5/1992 | Custer et al. |
| 5,112,300 | A | 5/1992 | Ureche |
| 5,123,903 | A | 6/1992 | Quaid et al. |
| 5,126,618 | A | 6/1992 | Takahashi et al. |
| D327,872 | S | 7/1992 | McMills et al. |
| D330,253 | S | 10/1992 | Burek |
| 5,152,762 | A | 10/1992 | McElhenney |
| 5,156,613 | A | 10/1992 | Sawyer |
| 5,156,633 | A | 10/1992 | Smith |
| 5,159,226 | A | 10/1992 | Montgomery |
| 5,160,334 | A | 11/1992 | Billings et al. |
| 5,162,044 | A | 11/1992 | Gahn et al. |
| 5,163,421 | A | 11/1992 | Bernstein et al. |
| 5,163,537 | A | 11/1992 | Radev |
| 5,167,619 | A | 12/1992 | Wuchinich |
| 5,167,725 | A | 12/1992 | Clark et al. |
| 5,172,344 | A | 12/1992 | Ehrlich |
| 5,174,276 | A | 12/1992 | Crockard |
| D332,660 | S | 1/1993 | Rawson et al. |
| 5,176,677 | A | 1/1993 | Wuchinich |
| 5,176,695 | A | 1/1993 | Dulebohn |
| 5,184,605 | A | 2/1993 | Grzeszykowski |
| 5,188,102 | A | 2/1993 | Idemoto et al. |
| D334,173 | S | 3/1993 | Liu et al. |
| 5,190,518 | A | 3/1993 | Takasu |
| 5,190,541 | A | 3/1993 | Abele et al. |
| 5,196,007 | A | 3/1993 | Ellman et al. |
| 5,205,459 | A | 4/1993 | Brinkerhoff et al. |
| 5,205,817 | A | 4/1993 | Idemoto et al. |
| 5,209,719 | A | 5/1993 | Baruch et al. |
| 5,209,776 | A | 5/1993 | Bass et al. |
| 5,213,103 | A | 5/1993 | Martin et al. |
| 5,213,569 | A | 5/1993 | Davis |
| 5,214,339 | A | 5/1993 | Naito |
| 5,217,460 | A | 6/1993 | Knoepfler |
| 5,218,529 | A | 6/1993 | Mever et al. |
| 5,221,282 | A | 6/1993 | Wuchinich |
| 5,222,937 | A | 6/1993 | Kagawa |
| 5,226,909 | A | 7/1993 | Evans et al. |
| 5,226,910 | A | 7/1993 | Kajiyama et al. |
| 5,234,428 | A | 8/1993 | Kaufman |
| 5,234,436 | A | 8/1993 | Eaton et al. |
| 5,241,236 | A | 8/1993 | Sasaki et al. |
| 5,241,968 | A | 9/1993 | Slater |
| 5,242,385 | A | 9/1993 | Strukel |
| 5,242,460 | A | 9/1993 | Klein et al. |
| 5,254,129 | A | 10/1993 | Alexander |
| 5,257,988 | A | 11/1993 | L'Esperance, Jr. |
| 5,258,004 | A | 11/1993 | Bales et al. |
| 5,258,006 | A | 11/1993 | Rydell et al. |
| 5,261,922 | A | 11/1993 | Hood |
| 5,263,957 | A | 11/1993 | Davison |
| 5,264,925 | A | 11/1993 | Shipp et al. |
| 5,269,297 | A | 12/1993 | Weng et al. |
| 5,275,166 | A | 1/1994 | Vaitekunas et al. |
| 5,275,607 | A | 1/1994 | Lo et al. |
| 5,275,609 | A | 1/1994 | Pingleton et al. |
| 5,282,800 | A | 2/1994 | Foshee et al. |
| 5,282,817 | A | 2/1994 | Hoogeboom et al. |
| 5,285,795 | A | 2/1994 | Ryan et al. |
| 5,285,945 | A | 2/1994 | Brinkerhoff et al. |
| 5,289,436 | A | 2/1994 | Terhune |
| 5,290,286 | A | 3/1994 | Parins |
| 5,293,863 | A | 3/1994 | Zhu et al. |
| 5,300,068 | A | 4/1994 | Rosar et al. |
| 5,304,115 | A | 4/1994 | Pflueger et al. |
| 5,306,280 | A | 4/1994 | Bregen et al. |
| D347,474 | S | 5/1994 | Olson |
| 5,307,976 | A | 5/1994 | Olson et al. |
| 5,309,927 | A | 5/1994 | Welch |
| 5,312,023 | A | 5/1994 | Green et al. |
| 5,312,327 | A | 5/1994 | Bales et al. |
| 5,312,425 | A | 5/1994 | Evans et al. |
| 5,318,525 | A | 6/1994 | West et al. |
| 5,318,563 | A | 6/1994 | Malis et al. |
| 5,318,564 | A | 6/1994 | Eggers |
| 5,318,570 | A | 6/1994 | Hood et al. |
| 5,318,589 | A | 6/1994 | Lichtman |
| 5,322,055 | A | 6/1994 | Davison et al. |
| 5,323,055 | A | 6/1994 | Yamazaki |
| 5,324,289 | A | 6/1994 | Eggers |
| 5,324,297 | A | 6/1994 | Hood et al. |
| 5,324,299 | A | 6/1994 | Davison et al. |
| 5,326,013 | A | 7/1994 | Green et al. |
| 5,326,342 | A | 7/1994 | Pflueger et al. |
| 5,330,471 | A | 7/1994 | Eggers |
| 5,330,502 | A | 7/1994 | Hassler et al. |
| 5,338,292 | A | 8/1994 | Clement et al. |
| 5,339,723 | A | 8/1994 | Huitema |
| 5,342,292 | A | 8/1994 | Nita et al. |
| 5,342,359 | A | 8/1994 | Rydel |
| 5,344,420 | A | 9/1994 | Hilal et al. |
| 5,345,937 | A | 9/1994 | Middleman et al. |
| 5,346,502 | A | 9/1994 | Estabrook et al. |
| 5,353,474 | A | 10/1994 | Good et al. |
| 5,354,265 | A | 10/1994 | Mackool |
| 5,356,064 | A | 10/1994 | Green et al. |
| 5,357,164 | A | 10/1994 | Imabayashi et al. |
| 5,357,423 | A | 10/1994 | Weaver et al. |
| 5,358,506 | A | 10/1994 | Green et al. |
| 5,359,994 | A | 11/1994 | Krauter et al. |
| 5,361,583 | A | 11/1994 | Huitema |
| 5,366,466 | A | 11/1994 | Christian et al. |

(56)         References Cited

U.S. PATENT DOCUMENTS

| 5,368,557 | A | 11/1994 | Nita et al. |
| 5,370,645 | A | 12/1994 | Klicek et al. |
| 5,371,429 | A | 12/1994 | Manna |
| 5,372,585 | A | 12/1994 | Tiefenbrun et al. |
| 5,374,813 | A | 12/1994 | Shipp |
| D354,564 | S | 1/1995 | Medema |
| 5,381,067 | A | 1/1995 | Greenstein et al. |
| 5,383,874 | A | 1/1995 | Jackson et al. |
| 5,383,883 | A | 1/1995 | Wilk et al. |
| 5,387,207 | A | 2/1995 | Dyer et al. |
| 5,387,215 | A | 2/1995 | Fisher |
| 5,389,098 | A | 2/1995 | Tsuruta et al. |
| 5,391,144 | A | 2/1995 | Sakural et al. |
| 5,394,187 | A | 2/1995 | Shipp |
| 5,395,033 | A | 3/1995 | Byme et al. |
| 5,395,312 | A | 3/1995 | Desal |
| 5,395,363 | A | 3/1995 | Billings et al. |
| 5,395,364 | A | 3/1995 | Anderhub et al. |
| 5,396,266 | A | 3/1995 | Brimhall |
| 5,396,900 | A | 3/1995 | Slater et al. |
| 5,397,293 | A | 3/1995 | Alliger et al. |
| 5,400,267 | A | 3/1995 | Denen et al. |
| 5,403,312 | A | 4/1995 | Yates et al. |
| 5,403,334 | A | 4/1995 | Evans et al. |
| 5,406,503 | A | 4/1995 | Williams, Jr. et al. |
| 5,408,268 | A | 4/1995 | Shipp |
| 5,409,453 | A | 4/1995 | Lundquist et al. |
| D358,887 | S | 5/1995 | Feinberg |
| 5,411,481 | A | 5/1995 | Allen et al. |
| 5,413,107 | A | 5/1995 | Oakley et al. |
| 5,417,709 | A | 5/1995 | Slater |
| 5,419,761 | A | 5/1995 | Narayanan et al. |
| 5,421,829 | A | 6/1995 | Olichney et al. |
| 5,423,844 | A | 6/1995 | Miller |
| 5,428,504 | A | 6/1995 | Bhatla |
| 5,429,131 | A | 7/1995 | Scheinman et al. |
| 5,438,997 | A | 8/1995 | Sieben et al. |
| 5,441,499 | A | 8/1995 | Fritzsch |
| 5,443,463 | A | 8/1995 | Stern et al. |
| 5,445,638 | A | 8/1995 | Rydell et al. |
| 5,445,639 | A | 8/1995 | Kuslich et al. |
| 5,447,509 | A | 9/1995 | Mills et al. |
| 5,449,370 | A | 9/1995 | Vaitekunas |
| 5,451,220 | A | 9/1995 | Ciervo |
| 5,451,227 | A | 9/1995 | Michaelson |
| 5,456,684 | A | 10/1995 | Schmidt et al. |
| 5,458,598 | A | 10/1995 | Feinberg et al. |
| 5,462,604 | A | 10/1995 | Shibano et al. |
| 5,465,895 | A | 11/1995 | Knodel et al. |
| 5,471,988 | A | 12/1995 | Fujio et al. |
| 5,472,443 | A | 12/1995 | Cordis et al. |
| 5,476,479 | A | 12/1995 | Green et al. |
| 5,478,003 | A | 12/1995 | Green et al. |
| 5,480,409 | A | 1/1996 | Riza |
| 5,483,501 | A | 1/1996 | Park et al. |
| 5,484,436 | A | 1/1996 | Eggers et al. |
| 5,486,162 | A | 1/1996 | Brumbach |
| 5,486,189 | A | 1/1996 | Mudry et al. |
| 5,490,860 | A | 2/1996 | Middle et al. |
| 5,496,317 | A | 3/1996 | Goble et al. |
| 5,496,411 | A | 3/1996 | Candy |
| 5,499,992 | A | 3/1996 | Meade et al. |
| 5,500,216 | A | 3/1996 | Julian et al. |
| 5,501,654 | A | 3/1996 | Failla et al. |
| 5,504,650 | A | 4/1996 | Katsui et al. |
| 5,505,693 | A | 4/1996 | Mackool |
| 5,507,738 | A | 4/1996 | Ciervo |
| 5,509,922 | A | 4/1996 | Aranyi et al. |
| 5,511,556 | A | 4/1996 | DeSantis |
| 5,520,704 | A | 5/1996 | Castro et al. |
| 5,522,832 | A | 6/1996 | Kugo et al. |
| 5,522,839 | A | 6/1996 | Pilling |
| 5,527,273 | A | 6/1996 | Manna et al. |
| 5,527,331 | A | 6/1996 | Kresch et al. |
| 5,531,744 | A | 7/1996 | Nardella et al. |
| 5,540,681 | A | 7/1996 | Strul et al. |
| 5,540,693 | A | 7/1996 | Fisher |
| 5,542,916 | A | 8/1996 | Hirsch et al. |
| 5,553,675 | A | 9/1996 | Pitzen et al. |
| 5,558,671 | A | 9/1996 | Yates |
| 5,562,609 | A | 10/1996 | Brumbach |
| 5,562,610 | A | 10/1996 | Brumbach |
| 5,562,659 | A | 10/1996 | Morris |
| 5,562,703 | A | 10/1996 | Desal |
| 5,563,179 | A | 10/1996 | Stone et al. |
| 5,569,164 | A | 10/1996 | Lurz |
| 5,571,121 | A | 11/1996 | Heifetz |
| 5,573,424 | A | 11/1996 | Poppe |
| 5,573,534 | A | 11/1996 | Stone |
| 5,575,799 | A | 11/1996 | Bolanos et al. |
| 5,577,654 | A | 11/1996 | Bishop |
| 5,582,618 | A | 12/1996 | Chin et al. |
| 5,584,830 | A | 12/1996 | Ladd et al. |
| 5,591,187 | A | 1/1997 | Dekel |
| 5,593,414 | A | 1/1997 | Shipp et al. |
| 5,599,350 | A | 2/1997 | Schulze et al. |
| 5,601,601 | A | 2/1997 | Tal et al. |
| 5,603,773 | A | 2/1997 | Campbell |
| 5,607,436 | A | 3/1997 | Pratt et al. |
| 5,607,450 | A | 3/1997 | Zvenyatsky et al. |
| 5,609,573 | A | 3/1997 | Sandock |
| 5,611,813 | A | 3/1997 | Lichtman |
| 5,618,304 | A | 4/1997 | Hart et al. |
| 5,618,307 | A | 4/1997 | Donlon et al. |
| 5,618,492 | A | 4/1997 | Auten et al. |
| 5,620,447 | A | 4/1997 | Smith et al. |
| 5,624,452 | A | 4/1997 | Yates |
| 5,626,578 | A | 5/1997 | Tihon |
| 5,626,587 | A | 5/1997 | Bishop et al. |
| 5,626,595 | A | 5/1997 | Sklar et al. |
| 5,628,760 | A | 5/1997 | Knoepfler |
| 5,630,420 | A | 5/1997 | Vaitekunas |
| 5,630,837 | A | 5/1997 | Crowley |
| 5,632,432 | A | 5/1997 | Schulze et al. |
| 5,632,717 | A | 5/1997 | Yoon |
| 5,640,741 | A | 6/1997 | Yano |
| D381,077 | S | 7/1997 | Hunt |
| 5,643,301 | A | 7/1997 | Mollenauer |
| 5,647,851 | A | 7/1997 | Pokras |
| 5,647,871 | A | 7/1997 | Levine et al. |
| 5,649,937 | A | 7/1997 | Bito et al. |
| 5,649,955 | A | 7/1997 | Hashimoto et al. |
| 5,651,780 | A | 7/1997 | Jackson et al. |
| 5,653,713 | A | 8/1997 | Michelson |
| 5,658,281 | A | 8/1997 | Heard |
| 5,662,662 | A | 9/1997 | Bishop et al. |
| 5,662,667 | A | 9/1997 | Knode |
| 5,665,085 | A | 9/1997 | Nardella |
| 5,665,100 | A | 9/1997 | Yoon |
| 5,669,922 | A | 9/1997 | Hood |
| 5,674,219 | A | 10/1997 | Monson et al. |
| 5,674,220 | A | 10/1997 | Fox et al. |
| 5,674,235 | A | 10/1997 | Parisi |
| 5,678,568 | A | 10/1997 | Uchikubo et al. |
| 5,688,270 | A | 11/1997 | Yates et al. |
| 5,690,269 | A | 11/1997 | Bolanos et al. |
| 5,693,051 | A | 12/1997 | Schulze et al. |
| 5,694,936 | A | 12/1997 | Fujimoto et al. |
| 5,695,510 | A | 12/1997 | Hood |
| 5,700,261 | A | 12/1997 | Brinkerhoff |
| 5,704,534 | A | 1/1998 | Huitema et al. |
| 5,704,791 | A | 1/1998 | Gillio |
| 5,709,680 | A | 1/1998 | Yates et al. |
| 5,711,472 | A | 1/1998 | Bryan |
| 5,713,896 | A | 2/1998 | Nardella |
| 5,715,817 | A | 2/1998 | Stevens-Wright et al. |
| 5,716,366 | A | 2/1998 | Yates |
| 5,717,306 | A | 2/1998 | Shipp |
| 5,720,742 | A | 2/1998 | Zacharias |
| 5,720,744 | A | 2/1998 | Eggleston et al. |
| 5,722,980 | A | 3/1998 | Schulz et al. |
| 5,728,130 | A | 3/1998 | Ishikawa et al. |
| 5,730,752 | A | 3/1998 | Alden et al. |
| 5,733,074 | A | 3/1998 | Stock et al. |

(56) References Cited

U.S. PATENT DOCUMENTS

| | | | |
|---|---|---|---|
| 5,735,848 | A | 4/1998 | Yates et al. |
| 5,735,875 | A | 4/1998 | Bonutti et al. |
| 5,741,226 | A | 4/1998 | Strukel et al. |
| 5,743,906 | A | 4/1998 | Parins et al. |
| 5,752,973 | A | 5/1998 | Kieturakis |
| 5,755,717 | A | 5/1998 | Yates et al. |
| 5,762,255 | A | 6/1998 | Chrisman et al. |
| 5,766,164 | A | 6/1998 | Mueller et al. |
| 5,772,659 | A | 6/1998 | Becker et al. |
| 5,776,130 | A | 7/1998 | Buysse et al. |
| 5,776,155 | A | 7/1998 | Beaupre et al. |
| 5,779,130 | A | 7/1998 | Alesi et al. |
| 5,779,701 | A | 7/1998 | McBrayer et al. |
| 5,782,834 | A | 7/1998 | Lucey et al. |
| 5,792,135 | A | 8/1998 | Madhani et al. |
| 5,792,138 | A | 8/1998 | Shipp |
| 5,792,165 | A | 8/1998 | Klieman et al. |
| 5,796,188 | A | 8/1998 | Bays |
| 5,797,941 | A | 8/1998 | Schulze et al. |
| 5,797,959 | A | 8/1998 | Castro et al. |
| 5,800,432 | A | 9/1998 | Swanson |
| 5,800,448 | A | 9/1998 | Banko |
| 5,800,449 | A | 9/1998 | Wales |
| 5,805,141 | A | 9/1998 | Rosenberg et al. |
| 5,807,310 | A | 9/1998 | Hood |
| 5,807,393 | A | 9/1998 | Williamson, IV et al. |
| 5,808,396 | A | 9/1998 | Boukhny |
| 5,810,811 | A | 9/1998 | Yates et al. |
| 5,810,828 | A | 9/1998 | Lightman et al. |
| 5,810,859 | A | 9/1998 | DiMatteo et al. |
| 5,810,869 | A | 9/1998 | Kaplan et al. |
| 5,817,033 | A | 10/1998 | DeSantis et al. |
| 5,817,084 | A | 10/1998 | Jensen |
| 5,817,093 | A | 10/1998 | Williamson, IV et al. |
| 5,817,119 | A | 10/1998 | Klieman et al. |
| 5,823,197 | A | 10/1998 | Edwards |
| 5,827,323 | A | 10/1998 | Klieman et al. |
| 5,828,160 | A | 10/1998 | Sugishita |
| 5,833,696 | A | 11/1998 | Whitfield et al. |
| 5,836,897 | A | 11/1998 | Sakurai et al. |
| 5,836,909 | A | 11/1998 | Cosmescu |
| 5,836,943 | A | 11/1998 | Miller, III |
| 5,836,957 | A | 11/1998 | Schulz et al. |
| 5,836,990 | A | 11/1998 | Li |
| 5,843,109 | A | 12/1998 | Mehta et al. |
| 5,851,212 | A | 12/1998 | Ziros et al. |
| 5,853,290 | A | 12/1998 | Winston |
| 5,853,412 | A | 12/1998 | Berger |
| 5,858,018 | A | 1/1999 | Shipp et al. |
| 5,865,361 | A | 2/1999 | Milliman et al. |
| 5,873,873 | A | 2/1999 | Smith et al. |
| 5,873,882 | A | 2/1999 | Straub et al. |
| 5,876,401 | A | 3/1999 | Schulze et al. |
| 5,878,193 | A | 3/1999 | Wang et al. |
| 5,879,363 | A | 3/1999 | Urich |
| 5,879,364 | A | 3/1999 | Bromfield et al. |
| 5,880,668 | A | 3/1999 | Hall |
| 5,883,615 | A | 3/1999 | Fago et al. |
| 5,891,142 | A | 4/1999 | Eggers et al. |
| 5,893,835 | A | 4/1999 | Witt et al. |
| 5,893,880 | A | 4/1999 | Egan et al. |
| 5,895,412 | A | 4/1999 | Tucker |
| 5,897,523 | A | 4/1999 | Wright et al. |
| 5,897,569 | A | 4/1999 | Kellogg et al. |
| 5,903,607 | A | 5/1999 | Tailliet |
| 5,904,681 | A | 5/1999 | West, Jr. |
| 5,906,625 | A | 5/1999 | Bito et al. |
| 5,906,627 | A | 5/1999 | Spaulding |
| 5,906,628 | A | 5/1999 | Miyawaki et al. |
| 5,910,129 | A | 6/1999 | Koblish et al. |
| 5,910,150 | A | 6/1999 | Saadat |
| 5,911,699 | A | 6/1999 | Anis et al. |
| 5,916,229 | A | 6/1999 | Evans |
| 5,921,956 | A | 7/1999 | Grinberg et al. |
| 5,929,846 | A | 7/1999 | Rosenberg et al. |
| 5,935,143 | A | 8/1999 | Hood |
| 5,935,144 | A | 8/1999 | Estabrook |
| 5,938,633 | A | 8/1999 | Beaupre |
| 5,941,887 | A | 8/1999 | Steen et al. |
| 5,944,718 | A | 8/1999 | Austin et al. |
| 5,944,737 | A | 8/1999 | Tsonton et al. |
| 5,947,984 | A | 9/1999 | Whipple |
| 5,954,736 | A | 9/1999 | Bishop et al. |
| 5,954,746 | A | 9/1999 | Holthaus et al. |
| 5,957,882 | A | 9/1999 | Nita et al. |
| 5,957,943 | A | 9/1999 | Vaitekunas |
| 5,968,007 | A | 10/1999 | Simon et al. |
| 5,968,060 | A | 10/1999 | Kellogg |
| 5,971,949 | A | 10/1999 | Levin et al. |
| 5,974,342 | A | 10/1999 | Petrofsky |
| D416,089 | S | 11/1999 | Barton et al. |
| 5,980,510 | A | 11/1999 | Tsonton et al. |
| 5,980,546 | A | 11/1999 | Hood |
| 5,984,938 | A | 11/1999 | Yoon |
| 5,989,274 | A | 11/1999 | Davison et al. |
| 5,989,275 | A | 11/1999 | Estabrook et al. |
| 5,993,465 | A | 11/1999 | Shipp et al. |
| 5,993,972 | A | 11/1999 | Reich et al. |
| 5,994,855 | A | 11/1999 | Lundell et al. |
| 6,001,120 | A | 12/1999 | Levin |
| 6,003,517 | A | 12/1999 | Sheffield et al. |
| 6,004,335 | A | 12/1999 | Vaitekunas et al. |
| 6,007,552 | A | 12/1999 | Fogarty et al. |
| 6,013,052 | A | 1/2000 | Durman et al. |
| 6,024,741 | A | 2/2000 | Williamson, IV et al. |
| 6,024,744 | A | 2/2000 | Kese et al. |
| 6,024,750 | A | 2/2000 | Mastri et al. |
| 6,027,515 | A | 2/2000 | Cimino |
| 6,031,526 | A | 2/2000 | Shipp |
| 6,033,375 | A | 3/2000 | Brumbach |
| 6,033,399 | A | 3/2000 | Gines |
| 6,036,667 | A | 3/2000 | Manna et al. |
| 6,036,707 | A | 3/2000 | Spaulding |
| 6,039,734 | A | 3/2000 | Goble |
| 6,048,224 | A | 4/2000 | Kay |
| 6,050,943 | A | 4/2000 | Slayton et al. |
| 6,050,996 | A | 4/2000 | Schmaltz et al. |
| 6,051,010 | A | 4/2000 | DiMatteo et al. |
| 6,053,906 | A | 4/2000 | Honda et al. |
| 6,056,735 | A | 5/2000 | Okada et al. |
| 6,063,050 | A | 5/2000 | Manna et al. |
| 6,063,098 | A | 5/2000 | Houser et al. |
| 6,066,132 | A | 5/2000 | Chen et al. |
| 6,066,151 | A | 5/2000 | Miyawaki et al. |
| 6,068,627 | A | 5/2000 | Orszulak et al. |
| 6,068,629 | A | 5/2000 | Haissaguerre et al. |
| 6,068,647 | A | 5/2000 | Witt et al. |
| 6,074,389 | A | 6/2000 | Levine et al. |
| 6,077,285 | A | 6/2000 | Boukhny |
| 6,083,191 | A | 7/2000 | Rose |
| 6,086,544 | A | 7/2000 | Hibner et al. |
| 6,086,584 | A | 7/2000 | Miller |
| 6,090,120 | A | 7/2000 | Wright et al. |
| 6,091,995 | A | 7/2000 | Ingle et al. |
| 6,096,033 | A | 8/2000 | Tu et al. |
| 6,099,483 | A | 8/2000 | Palmer et al. |
| 6,099,542 | A | 8/2000 | Cohn et al. |
| 6,099,550 | A | 8/2000 | Yoon |
| 6,109,500 | A | 8/2000 | Alli et al. |
| 6,110,127 | A | 8/2000 | Suzuki |
| 6,113,594 | A | 9/2000 | Savage |
| 6,113,598 | A | 9/2000 | Baker |
| 6,117,152 | A | 9/2000 | Huitema |
| 6,120,519 | A | 9/2000 | Weber et al. |
| H1904 | H | 10/2000 | Yates et al. |
| 6,126,629 | A | 10/2000 | Perkins |
| 6,129,735 | A | 10/2000 | Okada et al. |
| 6,129,740 | A | 10/2000 | Michelson |
| 6,132,368 | A | 10/2000 | Cooper |
| 6,132,427 | A | 10/2000 | Jones et al. |
| 6,132,448 | A | 10/2000 | Perez et al. |
| 6,139,320 | A | 10/2000 | Hahn |
| 6,139,561 | A | 10/2000 | Shibata et al. |
| 6,142,615 | A | 11/2000 | Qiu et al. |

(56)        References Cited

U.S. PATENT DOCUMENTS

| 6,142,994 | A | 11/2000 | Swanson et al. |
| 6,144,402 | A | 11/2000 | Norsworthy et al. |
| 6,147,560 | A | 11/2000 | Erhage et al. |
| 6,152,902 | A | 11/2000 | Christian et al. |
| 6,152,923 | A | 11/2000 | Ryan |
| 6,154,198 | A | 11/2000 | Rosenberg |
| 6,156,029 | A | 12/2000 | Mueller |
| 6,159,160 | A | 12/2000 | Hsel et al. |
| 6,159,175 | A | 12/2000 | Strukel et al. |
| 6,162,194 | A | 12/2000 | Shipp |
| 6,162,208 | A | 12/2000 | Hipos |
| 6,165,150 | A | 12/2000 | Banko |
| 6,165,186 | A | 12/2000 | Fogarty et al. |
| 6,165,191 | A | 12/2000 | Shibata et al. |
| 6,174,309 | B1 | 1/2001 | Wrublewski et al. |
| 6,174,310 | B1 | 1/2001 | Kirwan, Jr. |
| 6,176,857 | B1 | 1/2001 | Ashley |
| 6,179,853 | B1 | 1/2001 | Sachse et al. |
| 6,183,426 | B1 | 2/2001 | Akisada et al. |
| 6,187,003 | B1 | 2/2001 | Buysse et al. |
| 6,190,386 | B1 | 2/2001 | Rydell |
| 6,193,709 | B1 | 2/2001 | Miyawaki et al. |
| 6,204,592 | B1 | 3/2001 | Hur |
| 6,205,855 | B1 | 3/2001 | Pfeiffer |
| 6,206,844 | B1 | 3/2001 | Reichel et al. |
| 6,206,876 | B1 | 3/2001 | Levine et al. |
| 6,206,877 | B1 | 3/2001 | Kese et al. |
| 6,210,337 | B1 | 4/2001 | Dunham et al. |
| 6,210,402 | B1 | 4/2001 | Olsen et al. |
| 6,210,403 | B1 | 4/2001 | Klicek |
| 6,214,023 | B1 | 4/2001 | Whipple et al. |
| 6,217,591 | B1 | 4/2001 | Egan et al. |
| 6,228,080 | B1 | 5/2001 | Gines |
| 6,228,104 | B1 | 5/2001 | Fogarty et al. |
| 6,231,565 | B1 | 5/2001 | Tovey et al. |
| 6,233,476 | B1 | 5/2001 | Strommer et al. |
| 6,238,366 | B1 | 5/2001 | Savage et al. |
| 6,241,724 | B1 | 6/2001 | Fleischman et al. |
| 6,245,065 | B1 | 6/2001 | Panescu et al. |
| 6,251,110 | B1 | 6/2001 | Wampler |
| 6,252,110 | B1 | 6/2001 | Uemura et al. |
| D444,365 | S | 7/2001 | Bass et al. |
| D445,092 | S | 7/2001 | Lee |
| D445,764 | S | 7/2001 | Lee |
| 6,254,623 | B1 | 7/2001 | Halbel, Jr. et al. |
| 6,257,241 | B1 | 7/2001 | Wampler |
| 6,258,034 | B1 | 7/2001 | Hanafy |
| 6,259,230 | B1 | 7/2001 | Chou |
| 6,267,761 | B1 | 7/2001 | Ryan |
| 6,270,471 | B1 | 8/2001 | Hechel et al. |
| 6,270,831 | B2 | 8/2001 | Kumar et al. |
| 6,273,852 | B1 | 8/2001 | Lehe et al. |
| 6,273,902 | B1 | 8/2001 | Fogarty et al. |
| 6,274,963 | B1 | 8/2001 | Estabrook et al. |
| 6,277,115 | B1 | 8/2001 | Saadat |
| 6,277,117 | B1 | 8/2001 | Tetzlaff et al. |
| 6,278,218 | B1 | 8/2001 | Madan et al. |
| 6,280,407 | B1 | 8/2001 | Manna et al. |
| 6,283,981 | B1 | 9/2001 | Beaupre |
| 6,287,344 | B1 | 9/2001 | Wampler et al. |
| 6,290,575 | B1 | 9/2001 | Shipp |
| 6,292,700 | B1 | 9/2001 | Morrison et al. |
| 6,293,954 | B1 | 9/2001 | Fogarty et al. |
| 6,299,591 | B1 | 10/2001 | Banko |
| 6,299,621 | B1 | 10/2001 | Fogarty et al. |
| 6,306,131 | B1 | 10/2001 | Hareyama et al. |
| 6,306,157 | B1 | 10/2001 | Shchervinsky |
| 6,309,400 | B2 | 10/2001 | Beaupre |
| 6,311,783 | B1 | 11/2001 | Harpell |
| 6,312,445 | B1 | 11/2001 | Fogarty et al. |
| 6,319,221 | B1 | 11/2001 | Savage et al. |
| 6,325,795 | B1 | 12/2001 | Lindemann et al. |
| 6,325,799 | B1 | 12/2001 | Goble |
| 6,325,811 | B1 | 12/2001 | Messerly |
| 6,328,751 | B1 | 12/2001 | Beaupre |
| 6,332,891 | B1 | 12/2001 | Himes |
| 6,333,488 | B1 | 12/2001 | Lawrence et al. |
| 6,338,657 | B1 | 1/2002 | Harper et al. |
| 6,340,352 | B1 | 1/2002 | Okada et al. |
| 6,340,878 | B1 | 1/2002 | Oglesbee |
| 6,350,269 | B1 | 2/2002 | Shipp et al. |
| 6,352,532 | B1 | 3/2002 | Kramer et al. |
| 6,358,264 | B2 | 3/2002 | Banko |
| 6,364,888 | B1 | 4/2002 | Niemeyer et al. |
| 6,379,320 | B1 | 4/2002 | Lafon et al. |
| D457,958 | S | 5/2002 | Dycus et al. |
| 6,383,194 | B1 | 5/2002 | Pothula |
| 6,384,690 | B1 | 5/2002 | Wilhelmsson et al. |
| 6,387,094 | B1 | 5/2002 | Eitenmuller |
| 6,387,109 | B1 | 5/2002 | Davison et al. |
| 6,387,112 | B1 | 5/2002 | Fogarty et al. |
| 6,388,657 | B1 | 5/2002 | Natoli |
| 6,391,026 | B1 | 5/2002 | Hung et al. |
| 6,391,042 | B1 | 5/2002 | Cimino |
| 6,398,779 | B1 | 6/2002 | Buysse et al. |
| 6,402,743 | B1 | 6/2002 | Orszulak et al. |
| 6,402,748 | B1 | 6/2002 | Schoenman et al. |
| 6,405,733 | B1 | 6/2002 | Fogarty et al. |
| 6,409,722 | B1 | 6/2002 | Hoey et al. |
| 6,409,743 | B1 | 6/2002 | Fenton, Jr. |
| H2037 | H | 7/2002 | Yates et al. |
| 6,416,469 | B1 | 7/2002 | Phung et al. |
| 6,416,486 | B1 | 7/2002 | Wampler |
| 6,416,525 | B1 | 7/2002 | Shibata |
| 6,419,675 | B1 | 7/2002 | Gallo, Sr. |
| 6,423,073 | B2 | 7/2002 | Bowman |
| 6,423,082 | B1 | 7/2002 | Houser et al. |
| 6,425,906 | B1 | 7/2002 | Young et al. |
| 6,425,907 | B1 | 7/2002 | Shibata et al. |
| 6,428,538 | B1 | 8/2002 | Blewett et al. |
| 6,428,539 | B1 | 8/2002 | Baxter et al. |
| 6,430,446 | B1 | 8/2002 | Knowlton |
| 6,432,118 | B1 | 8/2002 | Messerly |
| 6,436,114 | B1 | 8/2002 | Novak et al. |
| 6,436,115 | B1 | 8/2002 | Beaupre |
| 6,440,062 | B1 | 8/2002 | Ouchi |
| 6,443,968 | B1 | 9/2002 | Holthaus et al. |
| 6,443,969 | B1 | 9/2002 | Novak et al. |
| 6,449,006 | B1 | 9/2002 | Shipp |
| 6,454,781 | B1 | 9/2002 | Witt et al. |
| 6,454,782 | B1 | 9/2002 | Schwemberger |
| 6,458,128 | B1 | 10/2002 | Schulze |
| 6,458,130 | B1 | 10/2002 | Frazier et al. |
| 6,458,142 | B1 | 10/2002 | Faller et al. |
| 6,461,363 | B1 | 10/2002 | Gadberry et al. |
| 6,464,689 | B1 | 10/2002 | Qin et al. |
| 6,464,702 | B2 | 10/2002 | Schulze et al. |
| 6,468,286 | B2 | 10/2002 | Mastri et al. |
| 6,475,211 | B2 | 11/2002 | Chess et al. |
| 6,475,215 | B1 | 11/2002 | Tanrisever |
| 6,480,796 | B2 | 11/2002 | Wiener |
| 6,485,490 | B2 | 11/2002 | Wampler et al. |
| 6,491,690 | B1 | 12/2002 | Goble et al. |
| 6,491,701 | B2 | 12/2002 | Tierney et al. |
| 6,491,708 | B2 | 12/2002 | Madan et al. |
| 6,497,715 | B2 | 12/2002 | Satou |
| 6,498,421 | B1 | 12/2002 | Oh et al. |
| 6,500,112 | B1 | 12/2002 | Khouri |
| 6,500,176 | B1 | 12/2002 | Truckal et al. |
| 6,500,188 | B2 | 12/2002 | Harper et al. |
| 6,500,312 | B2 | 12/2002 | Wedekamp |
| 6,503,248 | B1 | 1/2003 | Levine |
| 6,506,208 | B2 | 1/2003 | Hunt et al. |
| 6,511,478 | B1 | 1/2003 | Burnside et al. |
| 6,511,480 | B1 | 1/2003 | Tetzlaff et al. |
| 6,511,493 | B1 | 1/2003 | Moutafis et al. |
| 6,514,252 | B2 | 2/2003 | Nezhat et al. |
| 6,514,267 | B2 | 2/2003 | Jewett |
| 6,517,565 | B1 | 2/2003 | Whitman et al. |
| 6,524,251 | B2 | 2/2003 | Rabiner et al. |
| 6,524,316 | B1 | 2/2003 | Nicholson et al. |
| 6,526,976 | B1 | 3/2003 | Baran |
| 6,527,736 | B1 | 3/2003 | Attinger et al. |
| 6,531,846 | B1 | 3/2003 | Smith |

(56)  References Cited

U.S. PATENT DOCUMENTS

| | | | |
|---|---|---|---|
| 6,533,784 B2 | 3/2003 | Truckal et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,561,983 B2 | 5/2003 | Cronin et al. |
| 6,562,035 B1 | 5/2003 | Levin |
| 6,562,037 B2 | 5/2003 | Paton et al. |
| 6,562,059 B2 | 5/2003 | Edwards et al. |
| 6,565,558 B1 | 5/2003 | Lindenmeier et al. |
| 6,569,109 B2 | 5/2003 | Sakurai et al. |
| 6,569,178 B1 | 5/2003 | Miyawaki et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,929 B2 | 6/2003 | Sussman et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,599,288 B2 | 7/2003 | Maguire et al. |
| 6,602,229 B2 | 8/2003 | Coss |
| 6,602,252 B2 | 8/2003 | Mollenauer |
| 6,607,540 B1 | 8/2003 | Shipp |
| 6,610,059 B1 | 8/2003 | West, Jr. |
| 6,610,060 B2 | 8/2003 | Mulier et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,444 B2 | 9/2003 | Babaev |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,648,839 B2 | 11/2003 | Manna et al. |
| 6,648,883 B2 | 11/2003 | Francischelli et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,124 B2 | 12/2003 | Flesch et al. |
| 6,656,132 B1 | 12/2003 | Ouchi |
| 6,656,177 B2 | 12/2003 | Truckal et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,696 B2 | 12/2003 | Bacher et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,701 B2 | 2/2004 | Orszulak et al. |
| 6,685,703 B2 | 2/2004 | Pearson et al. |
| 6,689,086 B1 | 2/2004 | Nita et al. |
| 6,689,145 B2 | 2/2004 | Lee et al. |
| 6,689,146 B1 | 2/2004 | Himes |
| 6,690,960 B2 | 2/2004 | Chen et al. |
| 6,695,782 B2 | 2/2004 | Ranucci et al. |
| 6,695,840 B2 | 2/2004 | Schulze |
| 6,699,214 B2 | 3/2004 | Gellman |
| 6,702,761 B1 | 3/2004 | Damadian et al. |
| 6,702,821 B2 | 3/2004 | Bonutti |
| 6,712,805 B2 | 3/2004 | Weimann |
| 6,716,215 B1 | 4/2004 | David et al. |
| 6,719,692 B2 | 4/2004 | Kleffner et al. |
| 6,719,765 B2 | 4/2004 | Bonutti |
| 6,719,766 B1 | 4/2004 | Buelna et al. |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,154 B2 | 6/2004 | Fogarty et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckal et al. |
| 6,773,409 B2 | 8/2004 | Truckal et al. |
| 6,773,434 B2 | 8/2004 | Clarrocca |
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckal et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehmsperger et al. |
| 6,814,731 B2 | 11/2004 | Swanson |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,832,988 B2 | 12/2004 | Sproul |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,221 B1 | 5/2005 | Baillargeon et al. |
| 6,887,252 B1 | 5/2005 | Okada et al. |
| 6,893,435 B2 | 5/2005 | Goble |

(56)                References Cited

U.S. PATENT DOCUMENTS

| | | | |
|---|---|---|---|
| 6,899,685 B2 | 5/2005 | Kermode et al. |
| 6,905,497 B2 | 6/2005 | Truckal et al. |
| 6,908,463 B2 | 6/2005 | Treat et al. |
| 6,908,466 B1 | 6/2005 | Bonutti et al. |
| 6,908,472 B2 | 6/2005 | Wiener et al. |
| 6,913,579 B2 | 7/2005 | Truckal et al. |
| 6,915,623 B2 | 7/2005 | Dey et al. |
| 6,923,804 B2 | 8/2005 | Eggers et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakul et al. |
| 6,929,622 B2 | 8/2005 | Chian |
| 6,929,632 B2 | 8/2005 | Nita et al. |
| 6,929,644 B2 | 8/2005 | Truckal et al. |
| 6,932,876 B1 | 8/2005 | Statnikov |
| 6,933,656 B2 | 8/2005 | Matsushita et al. |
| D509,589 S | 9/2005 | Wells |
| 6,942,660 B2 | 9/2005 | Pantera et al. |
| 6,942,676 B2 | 9/2005 | Buelna |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,988,295 B2 | 1/2006 | Tillim |
| 6,989,017 B2 | 1/2006 | Howell et al. |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,382 B2 | 2/2006 | Gallo, Sr. |
| 7,002,283 B2 | 2/2006 | Li et al. |
| 7,004,951 B2 | 2/2006 | Gibbens, III |
| 7,011,657 B2 | 3/2006 | Truckal et al. |
| 7,014,638 B2 | 3/2006 | Michelson |
| 7,018,354 B2 | 3/2006 | Tazi |
| 7,018,389 B2 | 3/2006 | Camerlengo |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckal et al. |
| 7,074,218 B2 | 7/2006 | Washington et al. |
| 7,074,219 B2 | 7/2006 | Levine et al. |
| 7,077,036 B1 | 7/2006 | Adams |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,618 B2 | 8/2006 | Couture et al. |
| 7,083,619 B2 | 8/2006 | Truckal et al. |
| 7,087,054 B2 | 8/2006 | Truckal et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckal et al. |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,119,516 B2 | 10/2006 | Denning |
| 7,124,932 B2 | 10/2006 | Isaacson et al. |
| 7,125,409 B2 | 10/2006 | Truckal et al. |
| 7,128,720 B2 | 10/2006 | Podany |
| 7,131,860 B2 | 11/2006 | Sartor et al. |
| 7,131,970 B2 | 11/2006 | Moses et al. |
| 7,131,983 B2 | 11/2006 | Murakami |
| 7,135,018 B2 | 11/2006 | Ryan et al. |
| 7,135,029 B2 | 11/2006 | Makin et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,201 B2 | 1/2007 | Peshkovskiy et al. |
| 7,156,846 B2 | 1/2007 | Dycus et al. |
| 7,156,853 B2 | 1/2007 | Muratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,169,144 B2 | 1/2007 | Hoey et al. |
| 7,169,146 B2 | 1/2007 | Truckal et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,182,762 B2 | 2/2007 | Bortkiewicz |
| 7,186,253 B2 | 3/2007 | Truckal et al. |
| 7,189,233 B2 | 3/2007 | Truckal et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckal et al. |
| 7,223,229 B2 | 5/2007 | Inman et al. |
| 7,225,964 B2 | 6/2007 | Mastri et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,282,836 B2 | 10/2007 | Kwon et al. |
| 7,285,895 B2 | 10/2007 | Beaupre |
| 7,287,682 B1 | 10/2007 | Ezzat et al. |

(56) References Cited

U.S. PATENT DOCUMENTS

| | | | |
|---|---|---|---|
| 7,300,431 | B2 | 11/2007 | Dubrovsky |
| 7,300,435 | B2 | 11/2007 | Wham et al. |
| 7,300,446 | B2 | 11/2007 | Beaupre |
| 7,300,450 | B2 | 11/2007 | Vleugels et al. |
| 7,303,531 | B2 | 12/2007 | Lee et al. |
| 7,303,557 | B2 | 12/2007 | Wham et al. |
| 7,306,597 | B2 | 12/2007 | Manzo |
| 7,307,313 | B2 | 12/2007 | Ohyanagi et al. |
| 7,309,849 | B2 | 12/2007 | Truckal et al. |
| 7,311,706 | B2 | 12/2007 | Schoenman et al. |
| 7,311,709 | B2 | 12/2007 | Truckal et al. |
| 7,317,955 | B2 | 1/2008 | McGreevy |
| 7,318,831 | B2 | 1/2008 | Alvarez et al. |
| 7,318,832 | B2 | 1/2008 | Young et al. |
| 7,326,236 | B2 | 2/2008 | Andreas et al. |
| 7,329,257 | B2 | 2/2008 | Kanehira et al. |
| 7,331,410 | B2 | 2/2008 | Yong et al. |
| 7,335,165 | B2 | 2/2008 | Truwit et al. |
| 7,335,997 | B2 | 2/2008 | Wiener |
| 7,337,010 | B2 | 2/2008 | Howard et al. |
| 7,338,463 | B2 | 3/2008 | Vigil |
| 7,353,068 | B2 | 4/2008 | Tanaka et al. |
| 7,354,440 | B2 | 4/2008 | Truckal et al. |
| 7,357,287 | B2 | 4/2008 | Shelton, IV et al. |
| 7,361,172 | B2 | 4/2008 | Cimino |
| 7,364,577 | B2 | 4/2008 | Wham et al. |
| 7,367,976 | B2 | 5/2008 | Lawes et al. |
| 7,371,227 | B2 | 5/2008 | Zeiner |
| RE40,388 | E | 6/2008 | Gines |
| 7,380,695 | B2 | 6/2008 | Doll et al. |
| 7,380,696 | B2 | 6/2008 | Shelton, IV et al. |
| 7,381,209 | B2 | 6/2008 | Truckal et al. |
| 7,384,420 | B2 | 6/2008 | Dycus et al. |
| 7,390,317 | B2 | 6/2008 | Taylor et al. |
| 7,396,356 | B2 | 7/2008 | Mollenauer |
| 7,403,224 | B2 | 7/2008 | Fuller et al. |
| 7,404,508 | B2 | 7/2008 | Smith et al. |
| 7,407,077 | B2 | 8/2008 | Ortiz et al. |
| 7,408,288 | B2 | 8/2008 | Hara |
| 7,413,123 | B2 | 8/2008 | Ortenzi |
| 7,416,101 | B2 | 8/2008 | Shelton, IV et al. |
| 7,416,437 | B2 | 8/2008 | Sartor et al. |
| D576,725 | S | 9/2008 | Shumer et al. |
| 7,419,490 | B2 | 9/2008 | Falkenstein et al. |
| 7,422,139 | B2 | 9/2008 | Shelton, IV et al. |
| 7,422,463 | B2 | 9/2008 | Kuo |
| D578,643 | S | 10/2008 | Shumer et al. |
| D578,644 | S | 10/2008 | Shumer et al. |
| D578,645 | S | 10/2008 | Shumer et al. |
| 7,431,694 | B2 | 10/2008 | Stefanchik et al. |
| 7,431,704 | B2 | 10/2008 | Babaev |
| 7,435,582 | B2 | 10/2008 | Zimmermann et al. |
| 7,441,684 | B2 | 10/2008 | Shelton, IV et al. |
| 7,442,168 | B2 | 10/2008 | Novak et al. |
| 7,442,193 | B2 | 10/2008 | Shields et al. |
| 7,445,621 | B2 | 11/2008 | Dumbauld et al. |
| 7,449,004 | B2 | 11/2008 | Yamada et al. |
| 7,451,904 | B2 | 11/2008 | Shelton, IV |
| 7,455,208 | B2 | 11/2008 | Wales et al. |
| 7,455,641 | B2 | 11/2008 | Yamada et al. |
| 7,462,181 | B2 | 12/2008 | Kraft et al. |
| 7,464,846 | B2 | 12/2008 | Shelton, IV et al. |
| 7,472,815 | B2 | 1/2009 | Shelton, IV et al. |
| 7,473,253 | B2 | 1/2009 | Dycus et al. |
| 7,473,263 | B2 | 1/2009 | Johnston et al. |
| 7,479,148 | B2 | 1/2009 | Beaupre |
| 7,479,160 | B2 | 1/2009 | Branch et al. |
| 7,481,775 | B2 | 1/2009 | Weikel, Jr. et al. |
| 7,488,285 | B2 | 2/2009 | Honda et al. |
| 7,488,319 | B2 | 2/2009 | Yates |
| 7,491,201 | B2 | 2/2009 | Shields et al. |
| 7,491,202 | B2 | 2/2009 | Odom et al. |
| 7,494,468 | B2 | 2/2009 | Rabiner et al. |
| 7,494,501 | B2 | 2/2009 | Ahlberg et al. |
| 7,498,080 | B2 | 3/2009 | Tung et al. |
| 7,502,234 | B2 | 3/2009 | Goliszek et al. |
| 7,503,893 | B2 | 3/2009 | Kucklick |
| 7,503,895 | B2 | 3/2009 | Rabiner et al. |
| 7,506,790 | B2 | 3/2009 | Shelton, IV |
| 7,506,791 | B2 | 3/2009 | Omaits et al. |
| 7,510,107 | B2 | 3/2009 | Timm et al. |
| 7,510,556 | B2 | 3/2009 | Nguyen et al. |
| 7,513,025 | B2 | 4/2009 | Fischer |
| 7,517,349 | B2 | 4/2009 | Truckai et al. |
| 7,520,865 | B2 | 4/2009 | Radley Young et al. |
| 7,524,320 | B2 | 4/2009 | Tierney et al. |
| 7,530,986 | B2 | 5/2009 | Beaupre et al. |
| 7,533,830 | B1 | 5/2009 | Rose |
| 7,534,243 | B1 | 5/2009 | Chin et al. |
| D594,983 | S | 6/2009 | Price et al. |
| 7,540,871 | B2 | 6/2009 | Gonnering |
| 7,540,872 | B2 | 6/2009 | Schechter et al. |
| 7,543,730 | B1 | 6/2009 | Marczyk |
| 7,544,200 | B2 | 6/2009 | Houser |
| 7,549,564 | B2 | 6/2009 | Boudreaux |
| 7,550,216 | B2 | 6/2009 | Ofer et al. |
| 7,553,309 | B2 | 6/2009 | Buysse et al. |
| 7,559,450 | B2 | 7/2009 | Wales et al. |
| 7,559,452 | B2 | 7/2009 | Wales et al. |
| 7,563,259 | B2 | 7/2009 | Takahashi |
| 7,563,269 | B2 | 7/2009 | Hashiguch |
| 7,566,318 | B2 | 7/2009 | Haefner |
| 7,567,012 | B2 | 7/2009 | Namikawa |
| 7,568,603 | B2 | 8/2009 | Shelton, IV et al. |
| 7,569,057 | B2 | 8/2009 | Liu et al. |
| 7,572,266 | B2 | 8/2009 | Young et al. |
| 7,572,268 | B2 | 8/2009 | Babaev |
| 7,578,166 | B2 | 8/2009 | Ethridge et al. |
| 7,578,820 | B2 | 8/2009 | Moore et al. |
| 7,582,084 | B2 | 9/2009 | Swanson et al. |
| 7,582,086 | B2 | 9/2009 | Privitera et al. |
| 7,582,095 | B2 | 9/2009 | Shipp et al. |
| 7,585,181 | B2 | 9/2009 | Olsen |
| 7,586,289 | B2 | 9/2009 | Andruk et al. |
| 7,587,536 | B2 | 9/2009 | McLeod |
| 7,588,176 | B2 | 9/2009 | Timm et al. |
| 7,588,177 | B2 | 9/2009 | Racenet |
| 7,594,925 | B2 | 9/2009 | Danek et al. |
| 7,597,693 | B2 | 10/2009 | Garrison |
| 7,601,119 | B2 | 10/2009 | Shahinian |
| 7,604,150 | B2 | 10/2009 | Boudreaux |
| 7,607,557 | B2 | 10/2009 | Shelton, IV et al. |
| 7,608,054 | B2 | 10/2009 | Soring et al. |
| 7,617,961 | B2 | 11/2009 | Viola |
| 7,621,930 | B2 | 11/2009 | Houser |
| 7,625,370 | B2 | 12/2009 | Hart et al. |
| 7,627,936 | B2 | 12/2009 | Bromfield |
| 7,628,791 | B2 | 12/2009 | Garrison et al. |
| 7,628,792 | B2 | 12/2009 | Guerra |
| 7,632,267 | B2 | 12/2009 | Dahla |
| 7,632,269 | B2 | 12/2009 | Truckal et al. |
| 7,637,410 | B2 | 12/2009 | Marczyk |
| 7,641,653 | B2 | 1/2010 | Dalla Betta et al. |
| 7,641,671 | B2 | 1/2010 | Crainich |
| 7,644,848 | B2 | 1/2010 | Swayze et al. |
| 7,645,245 | B2 | 1/2010 | Sekino et al. |
| 7,645,277 | B2 | 1/2010 | McClurken et al. |
| 7,645,278 | B2 | 1/2010 | Ichihashi et al. |
| 7,648,499 | B2 | 1/2010 | Orszulak et al. |
| 7,654,431 | B2 | 2/2010 | Hueil et al. |
| 7,658,311 | B2 | 2/2010 | Boudreaux |
| 7,659,833 | B2 | 2/2010 | Warner et al. |
| 7,662,151 | B2 | 2/2010 | Crompton, Jr. et al. |
| 7,665,647 | B2 | 2/2010 | Shelton, IV et al. |
| 7,666,206 | B2 | 2/2010 | Taniguchi et al. |
| 7,670,334 | B2 | 3/2010 | Hueil et al. |
| 7,670,338 | B2 | 3/2010 | Albrecht et al. |
| 7,674,263 | B2 | 3/2010 | Ryan |
| 7,678,069 | B1 | 3/2010 | Baker et al. |
| 7,678,125 | B2 | 3/2010 | Shipp |
| 7,682,366 | B2 | 3/2010 | Sakurai et al. |
| 7,686,763 | B2 | 3/2010 | Vaezy et al. |
| 7,686,770 | B2 | 3/2010 | Cohen |
| 7,686,826 | B2 | 3/2010 | Lee et al. |

(56)                References Cited

U.S. PATENT DOCUMENTS

| | | | |
|---|---|---|---|
| 7,688,028 | B2 | 3/2010 | Phillips et al. |
| 7,691,095 | B2 | 4/2010 | Bednarek et al. |
| 7,691,098 | B2 | 4/2010 | Wallace et al. |
| 7,696,670 | B2 | 4/2010 | Sakamoto |
| 7,699,846 | B2 | 4/2010 | Ryan |
| 7,703,459 | B2 | 4/2010 | Saadat et al. |
| 7,703,653 | B2 | 4/2010 | Shah et al. |
| 7,708,735 | B2 | 5/2010 | Chapman et al. |
| 7,708,751 | B2 | 5/2010 | Hughes et al. |
| 7,708,758 | B2 | 5/2010 | Lee et al. |
| 7,713,202 | B2 | 5/2010 | Boukhny et al. |
| 7,713,267 | B2 | 5/2010 | Pozzato |
| 7,714,481 | B2 | 5/2010 | Sakai |
| 7,717,312 | B2 | 5/2010 | Beetel |
| 7,717,914 | B2 | 5/2010 | Kimura |
| 7,717,915 | B2 | 5/2010 | Miyazawa |
| 7,721,935 | B2 | 5/2010 | Racenet et al. |
| 7,722,527 | B2 | 5/2010 | Bouchier et al. |
| 7,722,607 | B2 | 5/2010 | Dumbauld et al. |
| D618,797 | S | 6/2010 | Price et al. |
| 7,726,537 | B2 | 6/2010 | Olson et al. |
| 7,727,177 | B2 | 6/2010 | Bayat |
| 7,734,476 | B2 | 6/2010 | Wildman et al. |
| 7,738,969 | B2 | 6/2010 | Bleich |
| 7,740,594 | B2 | 6/2010 | Hibner |
| 7,749,240 | B2 | 7/2010 | Takahashi et al. |
| 7,749,273 | B2 | 7/2010 | Cauthen, III et al. |
| 7,751,115 | B2 | 7/2010 | Song |
| 7,753,904 | B2 | 7/2010 | Shelton, IV et al. |
| 7,753,908 | B2 | 7/2010 | Swanson |
| 7,762,445 | B2 | 7/2010 | Heinrich et al. |
| 7,762,979 | B2 | 7/2010 | Wuchinich |
| D621,503 | S | 8/2010 | Otten et al. |
| 7,766,210 | B2 | 8/2010 | Shelton, IV et al. |
| 7,766,693 | B2 | 8/2010 | Sartor et al. |
| 7,766,910 | B2 | 8/2010 | Hixson et al. |
| 7,770,774 | B2 | 8/2010 | Mastri et al. |
| 7,770,775 | B2 | 8/2010 | Shelton, IV et al. |
| 7,771,425 | B2 | 8/2010 | Dycus et al. |
| 7,771,444 | B2 | 8/2010 | Patel et al. |
| 7,775,972 | B2 | 8/2010 | Brock et al. |
| 7,776,036 | B2 | 8/2010 | Schechter et al. |
| 7,776,037 | B2 | 8/2010 | Odom |
| 7,778,733 | B2 | 8/2010 | Nowlin et al. |
| 7,780,054 | B2 | 8/2010 | Wales |
| 7,780,593 | B2 | 8/2010 | Ueno et al. |
| 7,780,651 | B2 | 8/2010 | Madhani et al. |
| 7,780,659 | B2 | 8/2010 | Okada et al. |
| 7,780,663 | B2 | 8/2010 | Yates et al. |
| 7,784,662 | B2 | 8/2010 | Wales et al. |
| 7,784,663 | B2 | 8/2010 | Shelton, IV |
| 7,789,883 | B2 | 9/2010 | Takashino et al. |
| 7,793,814 | B2 | 9/2010 | Racenet et al. |
| 7,796,969 | B2 | 9/2010 | Kelly et al. |
| 7,798,386 | B2 | 9/2010 | Schall et al. |
| 7,799,020 | B2 | 9/2010 | Shores et al. |
| 7,799,045 | B2 | 9/2010 | Masuda |
| 7,803,152 | B2 | 9/2010 | Honda et al. |
| 7,803,156 | B2 | 9/2010 | Eder et al. |
| 7,803,168 | B2 | 9/2010 | Gifford et al. |
| 7,806,891 | B2 | 10/2010 | Nowlin et al. |
| 7,810,693 | B2 | 10/2010 | Broeh et al. |
| 7,811,283 | B2 | 10/2010 | Moses et al. |
| 7,815,641 | B2 | 10/2010 | Dodde et al. |
| 7,815,658 | B2 | 10/2010 | Murakami |
| 7,819,298 | B2 | 10/2010 | Hall et al. |
| 7,819,299 | B2 | 10/2010 | Shelton, IV et al. |
| 7,819,819 | B2 | 10/2010 | Quick et al. |
| 7,819,872 | B2 | 10/2010 | Johnson et al. |
| 7,821,143 | B2 | 10/2010 | Wiener |
| D627,066 | S | 11/2010 | Romero |
| 7,824,401 | B2 | 11/2010 | Manzo et al. |
| 7,828,808 | B2 | 11/2010 | Hinman et al. |
| 7,832,408 | B2 | 11/2010 | Shelton, IV et al. |
| 7,832,611 | B2 | 11/2010 | Boyden et al. |
| 7,832,612 | B2 | 11/2010 | Baxter, III et al. |
| 7,834,484 | B2 | 11/2010 | Sartor |
| 7,834,521 | B2 | 11/2010 | Habu et al. |
| 7,837,699 | B2 | 11/2010 | Yamada et al. |
| 7,845,537 | B2 | 12/2010 | Shelton, IV et al. |
| 7,846,155 | B2 | 12/2010 | Houser et al. |
| 7,846,159 | B2 | 12/2010 | Morrison et al. |
| 7,846,160 | B2 | 12/2010 | Payne et al. |
| 7,846,161 | B2 | 12/2010 | Dumbauld et al. |
| 7,854,735 | B2 | 12/2010 | Houser et al. |
| D631,155 | S | 1/2011 | Peine et al. |
| 7,861,906 | B2 | 1/2011 | Doll et al. |
| 7,862,560 | B2 | 1/2011 | Marion |
| 7,867,228 | B2 | 1/2011 | Nobis et al. |
| 7,871,392 | B2 | 1/2011 | Sartor |
| 7,871,423 | B2 | 1/2011 | Livneh |
| 7,876,030 | B2 | 1/2011 | Taki et al. |
| D631,965 | S | 2/2011 | Price et al. |
| 7,878,991 | B2 | 2/2011 | Babaev |
| 7,879,033 | B2 | 2/2011 | Sartor et al. |
| 7,879,035 | B2 | 2/2011 | Garrison et al. |
| 7,879,070 | B2 | 2/2011 | Ortiz et al. |
| 7,883,465 | B2 | 2/2011 | Donofrio et al. |
| 7,883,475 | B2 | 2/2011 | Dupont et al. |
| 7,892,606 | B2 | 2/2011 | Thies et al. |
| 7,896,875 | B2 | 3/2011 | Heim et al. |
| 7,897,792 | B2 | 3/2011 | Iikura et al. |
| 7,901,400 | B2 | 3/2011 | Wham et al. |
| 7,901,423 | B2 | 3/2011 | Stulen et al. |
| 7,905,881 | B2 | 3/2011 | Masuda et al. |
| 7,909,220 | B2 | 3/2011 | Viola |
| 7,909,824 | B2 | 3/2011 | Masuda et al. |
| 7,918,848 | B2 | 4/2011 | Lau et al. |
| 7,919,184 | B2 | 4/2011 | Mohapatra et al. |
| 7,922,061 | B2 | 4/2011 | Shelton, IV et al. |
| 7,922,651 | B2 | 4/2011 | Yamada et al. |
| 7,922,716 | B2 | 4/2011 | Malecki et al. |
| 7,931,611 | B2 | 4/2011 | Novak et al. |
| 7,931,649 | B2 | 4/2011 | Couture et al. |
| D637,288 | S | 5/2011 | Houghton |
| D638,540 | S | 5/2011 | Ijiri et al. |
| 7,935,114 | B2 | 5/2011 | Takashino et al. |
| 7,936,203 | B2 | 5/2011 | Zimlich |
| 7,951,095 | B2 | 5/2011 | Makin et al. |
| 7,951,165 | B2 | 5/2011 | Golden et al. |
| 7,955,331 | B2 | 6/2011 | Truckal et al. |
| 7,959,050 | B2 | 6/2011 | Smith et al. |
| 7,959,626 | B2 | 6/2011 | Hong et al. |
| 7,963,963 | B2 | 6/2011 | Francischelli et al. |
| 7,967,602 | B2 | 6/2011 | Lindquist |
| 7,972,329 | B2 | 7/2011 | Refior et al. |
| 7,976,544 | B2 | 7/2011 | McClurken et al. |
| 7,980,443 | B2 | 7/2011 | Scheib et al. |
| 7,981,050 | B2 | 7/2011 | Ritchart et al. |
| 7,981,113 | B2 | 7/2011 | Truckai et al. |
| 7,997,278 | B2 | 8/2011 | Utley et al. |
| 7,998,157 | B2 | 8/2011 | Culp et al. |
| 8,002,732 | B2 | 8/2011 | Visconti |
| 8,006,358 | B2 | 8/2011 | Cooke et al. |
| 8,016,843 | B2 | 9/2011 | Escaf |
| 8,020,743 | B2 | 9/2011 | Shelton, IV |
| 8,025,630 | B2 | 9/2011 | Murakami et al. |
| 8,028,885 | B2 | 10/2011 | Smith et al. |
| 8,033,173 | B2 | 10/2011 | Ehlert et al. |
| 8,038,693 | B2 | 10/2011 | Allen |
| 8,048,011 | B2 | 11/2011 | Okabe |
| 8,048,070 | B2 | 11/2011 | O'Brien et al. |
| 8,052,672 | B2 | 11/2011 | Laufer et al. |
| 8,056,720 | B2 | 11/2011 | Hawkes |
| 8,057,467 | B2 | 11/2011 | Faller et al. |
| 8,057,468 | B2 | 11/2011 | Konesky |
| 8,057,498 | B2 | 11/2011 | Robertson |
| 8,058,771 | B2 | 11/2011 | Giordano et al. |
| 8,061,014 | B2 | 11/2011 | Smith et al. |
| 8,066,167 | B2 | 11/2011 | Measamer et al. |
| 8,070,036 | B1 | 12/2011 | Knodel |
| 8,070,711 | B2 | 12/2011 | Bassinger et al. |
| 8,070,762 | B2 | 12/2011 | Escudero et al. |
| 8,075,555 | B2 | 12/2011 | Truckal et al. |

(56)                   References Cited

U.S. PATENT DOCUMENTS

| | | | |
|---|---|---|---|
| 8,075,558 | B2 | 12/2011 | Truckal et al. |
| 8,089,197 | B2 | 1/2012 | Rinner et al. |
| 8,092,475 | B2 | 1/2012 | Cotter et al. |
| 8,097,012 | B2 | 1/2012 | Kagarise |
| 8,100,894 | B2 | 1/2012 | Mucko et al. |
| 8,105,230 | B2 | 1/2012 | Honda et al. |
| 8,105,323 | B2 | 1/2012 | Buysse et al. |
| 8,105,324 | B2 | 1/2012 | Palanker et al. |
| 8,114,104 | B2 | 2/2012 | Young et al. |
| 8,128,624 | B2 | 3/2012 | Couture et al. |
| 8,133,218 | B2 | 3/2012 | Daw et al. |
| 8,136,712 | B2 | 3/2012 | Zingman |
| 8,137,263 | B2 | 3/2012 | Marescaux et al. |
| 8,141,762 | B2 | 3/2012 | Bedi et al. |
| 8,142,421 | B2 | 3/2012 | Cooper et al. |
| 8,142,461 | B2 | 3/2012 | Houser et al. |
| 8,147,488 | B2 | 4/2012 | Masuda |
| 8,147,508 | B2 | 4/2012 | Madan et al. |
| 8,152,801 | B2 | 4/2012 | Goldberg et al. |
| 8,152,825 | B2 | 4/2012 | Madan et al. |
| 8,157,145 | B2 | 4/2012 | Shelton, IV et al. |
| 8,161,977 | B2 | 4/2012 | Shelton, IV et al. |
| 8,162,966 | B2 | 4/2012 | Connor et al. |
| 8,172,846 | B2 | 5/2012 | Brunnett et al. |
| 8,172,870 | B2 | 5/2012 | Shipp |
| 8,177,800 | B2 | 5/2012 | Spitz et al. |
| 8,182,501 | B2 | 5/2012 | Houser et al. |
| 8,182,502 | B2 | 5/2012 | Stulen et al. |
| 8,186,560 | B2 | 5/2012 | Hess et al. |
| 8,186,877 | B2 | 5/2012 | Klimovitch et al. |
| 8,187,267 | B2 | 5/2012 | Pappone et al. |
| D661,801 | S | 6/2012 | Price et al. |
| D661,802 | S | 6/2012 | Price et al. |
| D661,803 | S | 6/2012 | Price et al. |
| D661,804 | S | 6/2012 | Price et al. |
| 8,197,472 | B2 | 6/2012 | Lau et al. |
| 8,197,479 | B2 | 6/2012 | Olson et al. |
| 8,197,502 | B2 | 6/2012 | Smith et al. |
| 8,207,651 | B2 | 6/2012 | Gilbert |
| 8,210,411 | B2 | 7/2012 | Yates et al. |
| 8,221,306 | B2 | 7/2012 | Okada et al. |
| 8,221,415 | B2 | 7/2012 | Francischelli |
| 8,226,665 | B2 | 7/2012 | Cohen |
| 8,226,675 | B2 | 7/2012 | Houser et al. |
| 8,231,607 | B2 | 7/2012 | Takuma |
| 8,235,917 | B2 | 8/2012 | Joseph et al. |
| 8,236,018 | B2 | 8/2012 | Yoshimine et al. |
| 8,236,019 | B2 | 8/2012 | Houser |
| 8,236,020 | B2 | 8/2012 | Smith et al. |
| 8,241,235 | B2 | 8/2012 | Kahler et al. |
| 8,241,271 | B2 | 8/2012 | Millman et al. |
| 8,241,282 | B2 | 8/2012 | Unger et al. |
| 8,241,283 | B2 | 8/2012 | Guerra et al. |
| 8,241,284 | B2 | 8/2012 | Dycus et al. |
| 8,241,312 | B2 | 8/2012 | Messerly |
| 8,246,575 | B2 | 8/2012 | Viola |
| 8,246,615 | B2 | 8/2012 | Behrike |
| 8,246,618 | B2 | 8/2012 | Bucciaglia et al. |
| 8,246,642 | B2 | 8/2012 | Houser et al. |
| 8,251,994 | B2 | 8/2012 | McKenna et al. |
| 8,252,012 | B2 | 8/2012 | Stulen |
| 8,253,303 | B2 | 8/2012 | Giordano et al. |
| 8,257,377 | B2 | 9/2012 | Wiener et al. |
| 8,257,387 | B2 | 9/2012 | Cunningham |
| 8,262,563 | B2 | 9/2012 | Bakos et al. |
| 8,267,300 | B2 | 9/2012 | Boudreaux |
| 8,273,087 | B2 | 9/2012 | Kimura et al. |
| D669,992 | S | 10/2012 | Schafer et al. |
| D669,993 | S | 10/2012 | Merchant et al. |
| 8,277,446 | B2 | 10/2012 | Heard |
| 8,277,447 | B2 | 10/2012 | Garrison et al. |
| 8,277,471 | B2 | 10/2012 | Wiener et al. |
| 8,282,581 | B2 | 10/2012 | Zhao et al. |
| 8,282,669 | B2 | 10/2012 | Gerber et al. |
| 8,286,846 | B2 | 10/2012 | Smith et al. |
| 8,287,485 | B2 | 10/2012 | Kimura et al. |
| 8,287,528 | B2 | 10/2012 | Wham et al. |
| 8,287,532 | B2 | 10/2012 | Carroll et al. |
| 8,292,886 | B2 | 10/2012 | Kerr et al. |
| 8,292,888 | B2 | 10/2012 | Whitman |
| 8,298,223 | B2 | 10/2012 | Wham et al. |
| 8,298,225 | B2 | 10/2012 | Gilbert |
| 8,298,232 | B2 | 10/2012 | Unger |
| 8,298,233 | B2 | 10/2012 | Mueller |
| 8,303,576 | B2 | 11/2012 | Brock |
| 8,303,580 | B2 | 11/2012 | Wham et al. |
| 8,303,583 | B2 | 11/2012 | Hosier et al. |
| 8,303,613 | B2 | 11/2012 | Crandall et al. |
| 8,306,629 | B2 | 11/2012 | Mioduski et al. |
| 8,308,040 | B2 | 11/2012 | Huang et al. |
| 8,319,400 | B2 | 11/2012 | Houser et al. |
| 8,323,302 | B2 | 12/2012 | Robertson et al. |
| 8,323,310 | B2 | 12/2012 | Kingsley |
| 8,328,061 | B2 | 12/2012 | Kasvikis |
| 8,328,761 | B2 | 12/2012 | Widenhouse et al. |
| 8,328,802 | B2 | 12/2012 | Deville et al. |
| 8,328,833 | B2 | 12/2012 | Cuny |
| 8,328,834 | B2 | 12/2012 | Isaacs et al. |
| 8,333,778 | B2 | 12/2012 | Smith et al. |
| 8,333,779 | B2 | 12/2012 | Smith et al. |
| 8,334,468 | B2 | 12/2012 | Palmer et al. |
| 8,334,635 | B2 | 12/2012 | Voegele et al. |
| 8,337,407 | B2 | 12/2012 | Quistgaard et al. |
| 8,338,726 | B2 | 12/2012 | Palmer et al. |
| 8,343,146 | B2 | 1/2013 | Godara et al. |
| 8,344,596 | B2 | 1/2013 | Nield et al. |
| 8,348,880 | B2 | 1/2013 | Messerly et al. |
| 8,348,967 | B2 | 1/2013 | Stulen |
| 8,353,297 | B2 | 1/2013 | Dacquay et al. |
| 8,357,103 | B2 | 1/2013 | Mark et al. |
| 8,357,158 | B2 | 1/2013 | McKenna et al. |
| 8,366,727 | B2 | 2/2013 | Witt et al. |
| 8,372,064 | B2 | 2/2013 | Douglass et al. |
| 8,372,099 | B2 | 2/2013 | Deville et al. |
| 8,372,101 | B2 | 2/2013 | Smith et al. |
| 8,372,102 | B2 | 2/2013 | Stulen et al. |
| 8,374,670 | B2 | 2/2013 | Selkee |
| 8,377,044 | B2 | 2/2013 | Coe et al. |
| 8,377,059 | B2 | 2/2013 | Deville et al. |
| 8,377,085 | B2 | 2/2013 | Smith et al. |
| 8,382,748 | B2 | 2/2013 | Geisel |
| 8,382,775 | B1 | 2/2013 | Bender et al. |
| 8,382,782 | B2 | 2/2013 | Robertson et al. |
| 8,382,792 | B2 | 2/2013 | Chojin |
| 8,388,646 | B2 | 3/2013 | Chojin |
| 8,388,647 | B2 | 3/2013 | Nau, Jr. et al. |
| 8,394,096 | B2 | 3/2013 | Moses et al. |
| 8,394,115 | B2 | 3/2013 | Houser et al. |
| 8,397,971 | B2 | 3/2013 | Yates et al. |
| 8,403,926 | B2 | 3/2013 | Nobis et al. |
| 8,403,945 | B2 | 3/2013 | Whitfield et al. |
| 8,403,948 | B2 | 3/2013 | Deville et al. |
| 8,403,949 | B2 | 3/2013 | Palmer et al. |
| 8,403,950 | B2 | 3/2013 | Palmer et al. |
| 8,409,234 | B2 | 4/2013 | Stahler et al. |
| 8,414,577 | B2 | 4/2013 | Boudreaux et al. |
| 8,418,073 | B2 | 4/2013 | Mohr et al. |
| 8,418,349 | B2 | 4/2013 | Smith et al. |
| 8,419,757 | B2 | 4/2013 | Smith et al. |
| 8,419,758 | B2 | 4/2013 | Smith et al. |
| 8,419,759 | B2 | 4/2013 | Dietz |
| 8,423,182 | B2 | 4/2013 | Robinson et al. |
| 8,425,161 | B2 | 4/2013 | Nagaya et al. |
| 8,425,410 | B2 | 4/2013 | Murray et al. |
| 8,425,545 | B2 | 4/2013 | Smith et al. |
| 8,430,811 | B2 | 4/2013 | Hess et al. |
| 8,430,876 | B2 | 4/2013 | Kappus et al. |
| 8,430,897 | B2 | 4/2013 | Novak et al. |
| 8,430,898 | B2 | 4/2013 | Wiener et al. |
| 8,435,257 | B2 | 5/2013 | Smith et al. |
| 8,435,258 | B2 | 5/2013 | Young et al. |
| 8,439,912 | B2 | 5/2013 | Cunningham et al. |
| 8,439,939 | B2 | 5/2013 | Deville et al. |
| 8,444,637 | B2 | 5/2013 | Podmore et al. |

(56) References Cited

U.S. PATENT DOCUMENTS

| | | | |
|---|---|---|---|
| 8,444,662 | B2 | 5/2013 | Palmer et al. |
| 8,444,663 | B2 | 5/2013 | Houser et al. |
| 8,444,664 | B2 | 5/2013 | Balanev et al. |
| 8,453,906 | B2 | 6/2013 | Huang et al. |
| 8,454,599 | B2 | 6/2013 | Inagaki et al. |
| 8,454,639 | B2 | 6/2013 | Du et al. |
| 8,460,288 | B2 | 6/2013 | Tamal et al. |
| 8,460,292 | B2 | 6/2013 | Truckai et al. |
| 8,460,326 | B2 | 6/2013 | Houser et al. |
| 8,461,744 | B2 | 6/2013 | Wiener et al. |
| 8,469,981 | B2 | 6/2013 | Robertson et al. |
| 8,479,969 | B2 | 7/2013 | Shelton, IV |
| 8,480,703 | B2 | 7/2013 | Nicholas et al. |
| 8,484,833 | B2 | 7/2013 | Cunningham et al. |
| 8,485,413 | B2 | 7/2013 | Scheib et al. |
| 8,485,970 | B2 | 7/2013 | Widenhouse et al. |
| 8,486,057 | B2 | 7/2013 | Behnke, II |
| 8,486,096 | B2 | 7/2013 | Robertson et al. |
| 8,491,578 | B2 | 7/2013 | Manwaring et al. |
| 8,491,625 | B2 | 7/2013 | Homer |
| 8,496,682 | B2 | 7/2013 | Guerra et al. |
| D687,549 | S | 8/2013 | Johnson et al. |
| 8,506,555 | B2 | 8/2013 | Ruiz Morales |
| 8,509,318 | B2 | 8/2013 | Tailliet |
| 8,512,336 | B2 | 8/2013 | Couture |
| 8,512,359 | B2 | 8/2013 | Whitman et al. |
| 8,512,364 | B2 | 8/2013 | Kowalski et al. |
| 8,512,365 | B2 | 8/2013 | Wiener et al. |
| 8,518,067 | B2 | 8/2013 | Masuda et al. |
| 8,523,889 | B2 | 9/2013 | Stulen et al. |
| 8,528,563 | B2 | 9/2013 | Gruber |
| 8,529,437 | B2 | 9/2013 | Taylor et al. |
| 8,529,565 | B2 | 9/2013 | Masuda et al. |
| 8,531,064 | B2 | 9/2013 | Robertson et al. |
| 8,535,311 | B2 | 9/2013 | Schall |
| 8,535,340 | B2 | 9/2013 | Allen |
| 8,535,341 | B2 | 9/2013 | Allen |
| 8,540,128 | B2 | 9/2013 | Shelton, IV et al. |
| 8,546,996 | B2 | 10/2013 | Messerly et al. |
| 8,546,999 | B2 | 10/2013 | Houser et al. |
| 8,551,077 | B2 | 10/2013 | Main et al. |
| 8,551,086 | B2 | 10/2013 | Kimura et al. |
| 8,562,592 | B2 | 10/2013 | Conlon et al. |
| 8,562,598 | B2 | 10/2013 | Falkenstein et al. |
| 8,562,604 | B2 | 10/2013 | Nishimura |
| 8,568,390 | B2 | 10/2013 | Mueller |
| 8,568,400 | B2 | 10/2013 | Gilbert |
| 8,568,412 | B2 | 10/2013 | Brandt et al. |
| 8,569,997 | B2 | 10/2013 | Lee |
| 8,573,461 | B2 | 11/2013 | Shelton, IV et al. |
| 8,573,465 | B2 | 11/2013 | Shelton, IV |
| 8,574,231 | B2 | 11/2013 | Boudreaux et al. |
| 8,574,253 | B2 | 11/2013 | Gruber et al. |
| 8,579,176 | B2 | 11/2013 | Smith et al. |
| 8,579,897 | B2 | 11/2013 | Vakharia et al. |
| 8,579,928 | B2 | 11/2013 | Robertson et al. |
| 8,579,937 | B2 | 11/2013 | Gresham |
| 8,591,459 | B2 | 11/2013 | Clymer et al. |
| 8,591,506 | B2 | 11/2013 | Wham et al. |
| 8,591,536 | B2 | 11/2013 | Robertson |
| D695,407 | S | 12/2013 | Price et al. |
| D696,631 | S | 12/2013 | Price et al. |
| 8,597,193 | B2 | 12/2013 | Grunwald et al. |
| 8,602,031 | B2 | 12/2013 | Reis et al. |
| 8,602,288 | B2 | 12/2013 | Shelton, IV et al. |
| 8,608,745 | B2 | 12/2013 | Guzman et al. |
| 8,610,334 | B2 | 12/2013 | Bromfield |
| 8,613,383 | B2 | 12/2013 | Beckman et al. |
| 8,616,431 | B2 | 12/2013 | Timm et al. |
| 8,622,274 | B2 | 1/2014 | Yates et al. |
| 8,623,011 | B2 | 1/2014 | Spivey |
| 8,623,016 | B2 | 1/2014 | Fischer |
| 8,623,027 | B2 | 1/2014 | Price et al. |
| 8,623,044 | B2 | 1/2014 | Timm et al. |
| 8,628,529 | B2 | 1/2014 | Aldridge et al. |
| 8,628,534 | B2 | 1/2014 | Jones et al. |
| 8,632,461 | B2 | 1/2014 | Glossop |
| 8,636,736 | B2 | 1/2014 | Yates et al. |
| 8,638,428 | B2 | 1/2014 | Brown |
| 8,640,788 | B2 | 2/2014 | Dachs, II et al. |
| 8,641,663 | B2 | 2/2014 | Kirschenman et al. |
| 8,647,350 | B2 | 2/2014 | Mohan et al. |
| 8,650,728 | B2 | 2/2014 | Wan et al. |
| 8,651,230 | B2 | 2/2014 | Peshkovsky et al. |
| 8,652,120 | B2 | 2/2014 | Giordano et al. |
| 8,652,132 | B2 | 2/2014 | Tsuchiya et al. |
| 8,652,155 | B2 | 2/2014 | Houser et al. |
| 8,659,208 | B1 | 2/2014 | Rose et al. |
| 8,663,220 | B2 | 3/2014 | Wiener et al. |
| 8,663,222 | B2 | 3/2014 | Anderson et al. |
| 8,663,262 | B2 | 3/2014 | Smith et al. |
| 8,668,691 | B2 | 3/2014 | Heard |
| 8,668,710 | B2 | 3/2014 | Slipszenko et al. |
| 8,684,253 | B2 | 4/2014 | Giordano et al. |
| 8,685,016 | B2 | 4/2014 | Wham et al. |
| 8,685,020 | B2 | 4/2014 | Weizman et al. |
| 8,690,582 | B2 | 4/2014 | Rohrbach et al. |
| 8,691,268 | B2 | 4/2014 | Weimann |
| 8,695,866 | B2 | 4/2014 | Leimbach et al. |
| 8,696,366 | B2 | 4/2014 | Chen et al. |
| 8,696,665 | B2 | 4/2014 | Hunt et al. |
| 8,702,609 | B2 | 4/2014 | Hadjicostis |
| 8,702,704 | B2 | 4/2014 | Shelton, IV et al. |
| 8,704,425 | B2 | 4/2014 | Giordano et al. |
| 8,708,213 | B2 | 4/2014 | Shelton, IV et al. |
| 8,709,031 | B2 | 4/2014 | Stulen |
| 8,709,035 | B2 | 4/2014 | Johnson et al. |
| 8,715,270 | B2 | 5/2014 | Weitzner et al. |
| 8,715,277 | B2 | 5/2014 | Weizman |
| 8,715,306 | B2 | 5/2014 | Faller et al. |
| 8,721,640 | B2 | 5/2014 | Taylor et al. |
| 8,721,657 | B2 | 5/2014 | Kondoh et al. |
| 8,734,443 | B2 | 5/2014 | Hixson et al. |
| 8,734,476 | B2 | 5/2014 | Rhee et al. |
| 8,747,238 | B2 | 6/2014 | Shelton, IV et al. |
| 8,747,351 | B2 | 6/2014 | Schultz |
| 8,747,404 | B2 | 6/2014 | Boudreaux et al. |
| 8,749,116 | B2 | 6/2014 | Messerly et al. |
| 8,752,264 | B2 | 6/2014 | Ackley et al. |
| 8,752,749 | B2 | 6/2014 | Moore et al. |
| 8,753,338 | B2 | 6/2014 | Widenhouse et al. |
| 8,754,570 | B2 | 6/2014 | Voegele et al. |
| 8,758,342 | B2 | 6/2014 | Bales et al. |
| 8,758,352 | B2 | 6/2014 | Cooper et al. |
| 8,764,735 | B2 | 7/2014 | Coe et al. |
| 8,764,747 | B2 | 7/2014 | Cummings et al. |
| 8,767,970 | B2 | 7/2014 | Eppolito |
| 8,770,459 | B2 | 7/2014 | Racenet et al. |
| 8,771,269 | B2 | 7/2014 | Sherman et al. |
| 8,771,270 | B2 | 7/2014 | Burbank |
| 8,773,001 | B2 | 7/2014 | Wiener et al. |
| 8,777,944 | B2 | 7/2014 | Frankhouser et al. |
| 8,779,648 | B2 | 7/2014 | Giordano et al. |
| 8,783,541 | B2 | 7/2014 | Shelton, IV et al. |
| 8,784,415 | B2 | 7/2014 | Malackowski et al. |
| 8,784,418 | B2 | 7/2014 | Romero |
| 8,790,342 | B2 | 7/2014 | Stulen et al. |
| 8,795,276 | B2 | 8/2014 | Dietz et al. |
| 8,795,327 | B2 | 8/2014 | Dietz et al. |
| 8,800,838 | B2 | 8/2014 | Shelton, IV |
| 8,801,710 | B2 | 8/2014 | Ullrich et al. |
| 8,801,752 | B2 | 8/2014 | Fortier et al. |
| 8,808,319 | B2 | 8/2014 | Houser et al. |
| 8,814,856 | B2 | 8/2014 | Elmouelhi et al. |
| 8,814,870 | B2 | 8/2014 | Paraschiv et al. |
| 8,820,605 | B2 | 9/2014 | Shelton, IV |
| 8,821,388 | B2 | 9/2014 | Naito et al. |
| 8,827,992 | B2 | 9/2014 | Koss et al. |
| 8,827,995 | B2 | 9/2014 | Schaller et al. |
| 8,834,466 | B2 | 9/2014 | Cummings et al. |
| 8,834,518 | B2 | 9/2014 | Faller et al. |
| 8,844,789 | B2 | 9/2014 | Shelton, IV et al. |
| 8,845,537 | B2 | 9/2014 | Tanaka et al. |
| 8,845,630 | B2 | 9/2014 | Mehta et al. |

(56)  References Cited

U.S. PATENT DOCUMENTS

| | | | |
|---|---|---|---|
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,709 B2 | 10/2014 | Akagane et al. |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,870,867 B2 | 10/2014 | Walberg et al. |
| 8,882,766 B2 | 11/2014 | Couture et al. |
| 8,882,791 B2 | 11/2014 | Stulen |
| 8,882,792 B2 | 11/2014 | Dietz et al. |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rloux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,931,682 B2 | 1/2015 | Timm et al. |
| 8,936,614 B2 | 1/2015 | Allen, IV |
| 8,939,974 B2 | 1/2015 | Boudreaux et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,961,515 B2 | 2/2015 | Twomey et al. |
| 8,961,547 B2 | 2/2015 | Dietz et al. |
| 8,968,283 B2 | 3/2015 | Kharin |
| 8,968,294 B2 | 3/2015 | Maass et al. |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DINardo et al. |
| 9,017,355 B2 | 4/2015 | Smith et al. |
| 9,017,372 B2 | 4/2015 | Artale et al. |
| 9,023,071 B2 | 5/2015 | Miller et al. |
| 9,023,072 B2 | 5/2015 | Young et al. |
| 9,028,397 B2 | 5/2015 | Naito |
| 9,028,476 B2 | 5/2015 | Bonn |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,039,690 B2 | 5/2015 | Kersten et al. |
| 9,039,695 B2 | 5/2015 | Giordano et al. |
| 9,039,705 B2 | 5/2015 | Takashino |
| 9,043,018 B2 | 5/2015 | Mohr |
| 9,044,227 B2 | 6/2015 | Shelton, IV et al. |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,093 B2 | 6/2015 | Aldridge et al. |
| 9,050,098 B2 | 6/2015 | Deville et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,063,049 B2 | 6/2015 | Beach et al. |
| 9,066,723 B2 | 6/2015 | Beller et al. |
| 9,066,747 B2 | 6/2015 | Robertson |
| 9,072,535 B2 | 7/2015 | Shelton, IV et al. |
| 9,072,536 B2 | 7/2015 | Shelton, IV et al. |
| 9,072,539 B2 | 7/2015 | Messerly et al. |
| 9,084,624 B2 | 7/2015 | Larkin et al. |
| 9,084,878 B2 | 7/2015 | Kawaguchi et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,940 B2 | 8/2015 | Twomey |
| 9,114,245 B2 | 8/2015 | Dietz et al. |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,125,722 B2 | 9/2015 | Schwartz |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,168,054 B2 | 10/2015 | Turner et al. |
| 9,168,055 B2 | 10/2015 | Houser et al. |
| 9,168,085 B2 | 10/2015 | Juzkiw et al. |
| 9,168,089 B2 | 10/2015 | Buysse et al. |
| 9,168,090 B2 | 10/2015 | Strobl et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,192,380 B2 | 11/2015 | (Tarinelli) Racenet et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,237,923 B2 | 1/2016 | Worrell et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,254,171 B2 | 2/2016 | Trees et al. |
| 9,259,234 B2 | 2/2016 | Robertson et al. |
| 9,259,265 B2 | 2/2016 | Harris et al. |
| 9,265,567 B2 | 2/2016 | Orban, III et al. |

(56) References Cited

U.S. PATENT DOCUMENTS

| | | | |
|---|---|---|---|
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,301,772 B2 | 4/2016 | Kimball et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,787 B2 | 5/2016 | Sanal et al. |
| 9,326,788 B2 | 5/2016 | Batross et al. |
| 9,333,025 B2 | 5/2016 | Monson et al. |
| 9,339,289 B2 | 5/2016 | Robertson |
| 9,339,323 B2 | 5/2016 | Eder et al. |
| 9,339,326 B2 | 5/2016 | McCullagh et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,754 B2 | 5/2016 | Vakharia et al. |
| 9,352,173 B2 | 5/2016 | Yamada et al. |
| 9,358,065 B2 | 6/2016 | Ladtkow et al. |
| 9,358,407 B2 | 6/2016 | Akagane |
| 9,364,230 B2 | 6/2016 | Shelton, IV et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,267 B2 | 6/2016 | Kerr et al. |
| 9,381,058 B2 | 7/2016 | Houser et al. |
| 9,386,983 B2 | 7/2016 | Swensgard et al. |
| 9,393,037 B2 | 7/2016 | Olson et al. |
| D763,442 S | 8/2016 | Price et al. |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,060 B2 | 8/2016 | Monson et al. |
| 9,427,249 B2 | 8/2016 | Robertson et al. |
| 9,439,668 B2 | 9/2016 | Timm et al. |
| 9,439,669 B2 | 9/2016 | Wiener et al. |
| 9,439,671 B2 | 9/2016 | Akagane |
| 9,445,784 B2 | 9/2016 | O'Keeffe |
| 9,445,832 B2 | 9/2016 | Wiener et al. |
| 9,445,833 B2 | 9/2016 | Akagane |
| 9,451,967 B2 | 9/2016 | Jordan et al. |
| 9,456,863 B2 | 10/2016 | Moua |
| 9,456,864 B2 | 10/2016 | Witt et al. |
| 9,468,498 B2 | 10/2016 | Sigmon, Jr. |
| 9,474,542 B2 | 10/2016 | Slipszenko et al. |
| 9,486,235 B2 | 11/2016 | Harrington et al. |
| 9,486,236 B2 | 11/2016 | Price et al. |
| 9,492,187 B2 | 11/2016 | Ravikumar et al. |
| 9,492,224 B2 | 11/2016 | Boudreaux et al. |
| 9,498,245 B2 | 11/2016 | Voegele et al. |
| 9,504,483 B2 | 11/2016 | Houser et al. |
| 9,504,524 B2 | 11/2016 | Behnke, I |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,846 B2 | 1/2017 | Boudreaux |
| 9,554,854 B2 | 1/2017 | Yates et al. |
| 9,561,038 B2 | 2/2017 | Shelton, IV et al. |
| 9,574,644 B2 | 2/2017 | Parihar |
| 9,592,072 B2 | 3/2017 | Akagane |
| 9,597,143 B2 | 3/2017 | Madan et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,622,729 B2 | 4/2017 | Dewaele et al. |
| 9,623,237 B2 | 4/2017 | Turner et al. |
| 9,636,135 B2 | 5/2017 | Stulen |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,111 B2 | 5/2017 | Shelton, IV et al. |
| 9,649,126 B2 | 5/2017 | Robertson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,675,374 B2 | 6/2017 | Stulen et al. |
| 9,675,375 B2 | 6/2017 | Houser et al. |
| 9,687,290 B2 | 6/2017 | Keller |
| 9,700,339 B2 | 7/2017 | Nield |
| 9,700,343 B2 | 7/2017 | Messerly et al. |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,724,118 B2 | 8/2017 | Schulte et al. |
| 9,724,152 B2 | 8/2017 | Horlle et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,737,735 B2 | 8/2017 | Dietz et al. |
| 9,743,947 B2 | 8/2017 | Price et al. |
| 9,757,142 B2 | 9/2017 | Shimizu |
| 9,757,186 B2 | 9/2017 | Boudreaux et al. |
| 9,764,164 B2 | 9/2017 | Wiener et al. |
| 9,782,214 B2 | 10/2017 | Houser et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,648 B2 | 10/2017 | Houser et al. |
| 9,801,675 B2 | 10/2017 | Sanal et al. |
| 9,808,308 B2 | 11/2017 | Faller et al. |
| 9,814,514 B2 | 11/2017 | Shelton, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,839,443 B2 | 12/2017 | Brockman et al. |
| 9,839,796 B2 | 12/2017 | Sawada |
| 9,848,901 B2 | 12/2017 | Robertson et al. |
| 9,848,902 B2 | 12/2017 | Price et al. |
| 9,848,937 B2 | 12/2017 | Trees et al. |
| 9,861,428 B2 | 1/2018 | Trees et al. |
| 9,872,725 B2 | 1/2018 | Worrell et al. |
| 9,877,720 B2 | 1/2018 | Worrell et al. |
| 9,877,776 B2 | 1/2018 | Boudreaux |
| 9,883,884 B2 | 2/2018 | Neurohr et al. |
| 9,888,958 B2 | 2/2018 | Evans et al. |
| 9,901,339 B2 | 2/2018 | Farascioni |
| 9,901,359 B2 | 2/2018 | Faller et al. |
| 9,907,563 B2 | 3/2018 | Germain et al. |
| 9,913,655 B2 | 3/2018 | Scheib et al. |
| 9,913,656 B2 | 3/2018 | Stulen |
| 9,913,680 B2 | 3/2018 | Voegele et al. |
| 9,918,736 B2 | 3/2018 | Van Tol et al. |
| 9,925,003 B2 | 3/2018 | Parihar et al. |
| 9,943,325 B2 | 4/2018 | Faller et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,987,033 B2 | 6/2018 | Neurohr et al. |
| 10,010,339 B2 | 7/2018 | Witt et al. |
| 10,010,341 B2 | 7/2018 | Houser et al. |

(56) References Cited

U.S. PATENT DOCUMENTS

| | | |
|---|---|---|
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,765 B2 | 7/2018 | Hibner et al. |
| 10,028,786 B2 | 7/2018 | Mucilli et al. |
| 10,034,684 B2 | 7/2018 | Weisenburgh, II et al. |
| 10,034,685 B2 | 7/2018 | Boudreaux et al. |
| 10,034,704 B2 | 7/2018 | Asher et al. |
| 10,039,588 B2 | 8/2018 | Harper et al. |
| 10,045,794 B2 | 8/2018 | Witt et al. |
| 10,045,819 B2 | 8/2018 | Jensen et al. |
| 10,070,916 B2 | 9/2018 | Artale |
| 10,085,762 B2 | 10/2018 | Timm et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweller et al. |
| 10,111,699 B2 | 10/2018 | Boudreaux |
| 10,117,667 B2 | 11/2018 | Robertson et al. |
| 10,117,702 B2 | 11/2018 | Danziger et al. |
| 10,130,410 B2 | 11/2018 | Strobl et al. |
| 10,154,852 B2 | 12/2018 | Conlon et al. |
| 10,159,524 B2 | 12/2018 | Yates et al. |
| 10,166,060 B2 | 1/2019 | Johnson et al. |
| 10,172,669 B2 | 1/2019 | Felder et al. |
| 10,179,022 B2 | 1/2019 | Yates et al. |
| 10,182,837 B2 | 1/2019 | Isola et al. |
| 10,188,385 B2 | 1/2019 | Kerr et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,201,365 B2 | 2/2019 | Boudreaux et al. |
| 10,201,382 B2 | 2/2019 | Wiener et al. |
| 10,226,273 B2 | 3/2019 | Messerly et al. |
| 10,231,747 B2 | 3/2019 | Stulen et al. |
| 10,245,064 B2 | 4/2019 | Rhee et al. |
| 10,245,065 B2 | 4/2019 | Witt et al. |
| 10,245,095 B2 | 4/2019 | Boudreaux |
| 10,251,664 B2 | 4/2019 | Shelton, IV et al. |
| 10,263,171 B2 | 4/2019 | Wiener et al. |
| 10,265,094 B2 | 4/2019 | Witt et al. |
| 10,265,117 B2 | 4/2019 | Wiener et al. |
| 10,265,118 B2 | 4/2019 | Gerhardt |
| D847,990 S | 5/2019 | Kimball |
| 10,278,721 B2 | 5/2019 | Dietz et al. |
| 10,285,723 B2 | 5/2019 | Conlon et al. |
| 10,285,724 B2 | 5/2019 | Faller et al. |
| 10,299,810 B2 | 5/2019 | Robertson et al. |
| 10,299,821 B2 | 5/2019 | Shelton, IV et al. |
| 10,314,638 B2 | 6/2019 | Gee et al. |
| 10,321,950 B2 | 6/2019 | Yates et al. |
| 10,335,182 B2 | 7/2019 | Stulen et al. |
| 10,335,614 B2 | 7/2019 | Messerly et al. |
| 10,342,602 B2 | 7/2019 | Strobl et al. |
| 10,357,303 B2 | 7/2019 | Conlon et al. |
| 10,363,058 B2 | 7/2019 | Roberson et al. |
| 10,368,892 B2 | 8/2019 | Stulen et al. |
| 10,368,894 B2 | 8/2019 | Madan et al. |
| 10,368,957 B2 | 8/2019 | Denzinger et al. |
| 10,398,466 B2 | 9/2019 | Stulen et al. |
| 10,398,497 B2 | 9/2019 | Batross et al. |
| 10,413,352 B2 | 9/2019 | Thomas et al. |
| 10,420,579 B2 | 9/2019 | Wiener et al. |
| 10,420,580 B2 | 9/2019 | Messerly et al. |
| 10,420,607 B2 | 9/2019 | Woloszko et al. |
| 10,426,507 B2 | 10/2019 | Wiener et al. |
| 10,426,978 B2 | 10/2019 | Akagane |
| 10,433,865 B2 | 10/2019 | Witt et al. |
| 10,433,866 B2 | 10/2019 | Witt et al. |
| 10,433,900 B2 | 10/2019 | Harris et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,463,421 B2 | 11/2019 | Boudreaux et al. |
| 10,463,887 B2 | 11/2019 | Witt et al. |
| 10,470,788 B2 | 11/2019 | Sinelnikov |
| 10,512,795 B2 | 12/2019 | Voegele et al. |
| 10,517,627 B2 | 12/2019 | Timm et al. |
| 10,524,854 B2 | 1/2020 | Woodruff et al. |
| 10,531,910 B2 | 1/2020 | Houser et al. |
| 10,537,351 B2 | 1/2020 | Shelton, IV et al. |
| 10,537,352 B2 | 1/2020 | Faller et al. |
| 10,537,667 B2 | 1/2020 | Anim |
| 10,543,008 B2 | 1/2020 | Vakharia et al. |
| 10,555,750 B2 | 2/2020 | Conlon et al. |
| 10,555,769 B2 | 2/2020 | Worrell et al. |
| 10,561,436 B2 | 2/2020 | Asher et al. |
| 10,575,892 B2 | 3/2020 | Danziger et al. |
| 10,595,929 B2 | 3/2020 | Boudreaux et al. |
| 10,595,930 B2 | 3/2020 | Scheib et al. |
| 10,603,064 B2 | 3/2020 | Zhang |
| 10,610,286 B2 | 4/2020 | Wiener et al. |
| 10,624,665 B2 | 4/2020 | Noul et al. |
| 10,624,691 B2 | 4/2020 | Wiener et al. |
| 10,639,092 B2 | 5/2020 | Corbett et al. |
| 10,677,764 B2 | 6/2020 | Ross et al. |
| 10,687,884 B2 | 6/2020 | Wiener et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,261 B2 | 7/2020 | Houser et al. |
| 10,729,458 B2 | 8/2020 | Stoddard et al. |
| 10,736,649 B2 | 8/2020 | Messerly et al. |
| 10,736,685 B2 | 8/2020 | Wiener et al. |
| 10,751,108 B2 | 8/2020 | Yates et al. |
| 10,758,294 B2 | 9/2020 | Jones |
| 10,779,845 B2 | 9/2020 | Timm et al. |
| 10,779,847 B2 | 9/2020 | Messerly et al. |
| 10,779,848 B2 | 9/2020 | Houser |
| 10,779,849 B2 | 9/2020 | Shelton, IV et al. |
| 10,779,879 B2 | 9/2020 | Yates et al. |
| 10,820,920 B2 | 11/2020 | Scoggins et al. |
| 10,820,938 B2 | 11/2020 | Fischer et al. |
| 10,828,056 B2 | 11/2020 | Messerly et al. |
| 10,828,057 B2 | 11/2020 | Neurohr et al. |
| 10,828,058 B2 | 11/2020 | Shelton, IV et al. |
| 10,828,059 B2 | 11/2020 | Price et al. |
| 10,835,307 B2 | 11/2020 | Shelton, IV et al. |
| 10,835,768 B2 | 11/2020 | Robertson et al. |
| 10,842,522 B2 | 11/2020 | Messerly et al. |
| 10,842,523 B2 | 11/2020 | Shelton, IV et al. |
| 10,842,580 B2 | 11/2020 | Gee et al. |
| 10,856,896 B2 | 12/2020 | Eichmann et al. |
| 10,874,418 B2 | 12/2020 | Houser et al. |
| 10,881,449 B2 | 1/2021 | Boudreaux et al. |
| 10,881,451 B2 | 1/2021 | Worrell et al. |
| 10,888,347 B2 | 1/2021 | Witt et al. |
| 10,893,883 B2 | 1/2021 | Dannaher |
| 10,912,603 B2 | 2/2021 | Boudreaux et al. |
| 10,952,759 B2 | 3/2021 | Messerly et al. |
| 10,959,769 B2 | 3/2021 | Mumaw et al. |
| 10,966,744 B2 | 4/2021 | Rhee et al. |
| 10,987,123 B2 | 4/2021 | Weir et al. |
| 11,000,707 B2 | 5/2021 | Voegele et al. |
| 11,006,971 B2 | 5/2021 | Faller et al. |
| 11,020,140 B2 | 6/2021 | Gee et al. |
| 11,033,292 B2 | 6/2021 | Green et al. |
| 11,033,322 B2 | 6/2021 | Wiener et al. |
| D924,400 S | 7/2021 | Kimball |
| 11,051,840 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,129,670 B2 | 9/2021 | Shelton, IV et al. |
| 11,134,978 B2 | 10/2021 | Shelton, IV et al. |
| 11,141,213 B2 | 10/2021 | Yates et al. |
| 2001/0011176 A1 | 8/2001 | Boukhny |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0032002 A1 | 10/2001 | McClurken et al. |

(56)  References Cited

U.S. PATENT DOCUMENTS

| | | |
|---|---|---|
| 2001/0039419 A1 | 11/2001 | Francischelli et al. |
| 2002/0002377 A1 | 1/2002 | Cimino |
| 2002/0002378 A1 | 1/2002 | Messerly |
| 2002/0016603 A1 | 2/2002 | Wells |
| 2002/0019649 A1 | 2/2002 | Sikora et al. |
| 2002/0022836 A1 | 2/2002 | Goble et al. |
| 2002/0029055 A1 | 3/2002 | Bonutti |
| 2002/0049551 A1 | 4/2002 | Friedman et al. |
| 2002/0052595 A1 | 5/2002 | Witt et al. |
| 2002/0052617 A1 | 5/2002 | Anis et al. |
| 2002/0077550 A1 | 6/2002 | Rabiner et al. |
| 2002/0099373 A1 | 7/2002 | Schulze et al. |
| 2002/0107446 A1 | 8/2002 | Rabiner et al. |
| 2002/0107517 A1 | 8/2002 | Witt et al. |
| 2002/0120266 A1 | 8/2002 | Truckal et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0183774 A1 | 12/2002 | Witt et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0093113 A1 | 5/2003 | Fogarty et al. |
| 2003/0109875 A1 | 6/2003 | Tetzlaff et al. |
| 2003/0114851 A1 | 6/2003 | Truckal et al. |
| 2003/0114874 A1 | 6/2003 | Craig et al. |
| 2003/0120306 A1 | 6/2003 | Burbank et al. |
| 2003/0130675 A1 | 7/2003 | Kasahara et al. |
| 2003/0130693 A1 | 7/2003 | Levin et al. |
| 2003/0139741 A1 | 7/2003 | Goble et al. |
| 2003/0144652 A1 | 7/2003 | Baker et al. |
| 2003/0144680 A1 | 7/2003 | Kellogg et al. |
| 2003/0149360 A1 | 8/2003 | Tardy et al. |
| 2003/0158548 A1 | 8/2003 | Phan et al. |
| 2003/0160698 A1 | 8/2003 | Andreasson et al. |
| 2003/0171747 A1 | 9/2003 | Kanehira et al. |
| 2003/0195496 A1 | 10/2003 | Maguire et al. |
| 2003/0199794 A1 | 10/2003 | Sakurai et al. |
| 2003/0204199 A1 | 10/2003 | Novak et al. |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0039242 A1 | 2/2004 | Tolkoff et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0121159 A1 | 6/2004 | Cloud et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0147934 A1 | 7/2004 | Kiester |
| 2004/0147945 A1 | 7/2004 | Fritzsch |
| 2004/0147946 A1 | 7/2004 | Mastri et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0199193 A1 | 10/2004 | Hayashi et al. |
| 2004/0199194 A1 | 10/2004 | Witt et al. |
| 2004/0204728 A1 | 10/2004 | Haefner |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267298 A1 | 12/2004 | Cimino |
| 2004/0267333 A1 | 12/2004 | Kronberg |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0049546 A1 | 3/2005 | Messerly et al. |
| 2005/0070800 A1 | 3/2005 | Takahashi |
| 2005/0085728 A1 | 4/2005 | Fukuda |
| 2005/0090817 A1 | 4/2005 | Phan |
| 2005/0096683 A1 | 5/2005 | Elins et al. |
| 2005/0099824 A1 | 5/2005 | Dowling et al. |
| 2005/0103819 A1 | 5/2005 | Racenet et al. |
| 2005/0131390 A1 | 6/2005 | Heinrich et al. |
| 2005/0143759 A1 | 6/2005 | Kelly |
| 2005/0143769 A1 | 6/2005 | White et al. |
| 2005/0149108 A1 | 7/2005 | Cox |
| 2005/0165345 A1 | 7/2005 | Laufer et al. |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0209620 A1 | 9/2005 | Du et al. |
| 2005/0222598 A1 | 10/2005 | Ho et al. |
| 2005/0228425 A1 | 10/2005 | Boukhny et al. |
| 2005/0234484 A1 | 10/2005 | Houser et al. |
| 2005/0249667 A1 | 11/2005 | Tuszynski et al. |
| 2005/0256405 A1 | 11/2005 | Makin et al. |
| 2005/0261581 A1 | 11/2005 | Hughes et al. |
| 2005/0261588 A1 | 11/2005 | Makin et al. |
| 2005/0267464 A1 | 12/2005 | Truckal et al. |
| 2005/0273090 A1 | 12/2005 | Nieman et al. |
| 2005/0288659 A1 | 12/2005 | Kimura et al. |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079877 A1 | 4/2006 | Houser et al. |
| 2006/0079878 A1 | 4/2006 | Houser |
| 2006/0079879 A1 | 4/2006 | Faller et al. |
| 2006/0084963 A1 | 4/2006 | Messerly |
| 2006/0095046 A1 | 5/2006 | Trieu et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0235306 A1 | 10/2006 | Cotter et al. |
| 2006/0241580 A1 | 10/2006 | Mittelstein et al. |
| 2006/0247558 A1 | 11/2006 | Yamada |
| 2006/0253050 A1 | 11/2006 | Yoshimine et al. |
| 2006/0257819 A1 | 11/2006 | Johnson |
| 2006/0264809 A1 | 11/2006 | Hansmann et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0032704 A1 | 2/2007 | Gandini et al. |
| 2007/0055228 A1 | 3/2007 | Berg et al. |
| 2007/0056596 A1 | 3/2007 | Fanney et al. |

(56)　　　　References Cited

U.S. PATENT DOCUMENTS

| | | |
|---|---|---|
| 2007/0060915 A1 | 3/2007 | Kucklick |
| 2007/0060935 A1 | 3/2007 | Schwardt et al. |
| 2007/0063618 A1 | 3/2007 | Bromfield |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0129716 A1 | 6/2007 | Daw et al. |
| 2007/0130771 A1 | 6/2007 | Ehlert et al. |
| 2007/0131034 A1 | 6/2007 | Ehlert et al. |
| 2007/0149881 A1 | 6/2007 | Rabin |
| 2007/0156119 A1 | 7/2007 | Wallace et al. |
| 2007/0156163 A1 | 7/2007 | Davison et al. |
| 2007/0162050 A1 | 7/2007 | Sartor |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175949 A1 | 8/2007 | Shelton, IV et al. |
| 2007/0185380 A1 | 8/2007 | Kucklick |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239028 A1 | 10/2007 | Houser et al. |
| 2007/0239101 A1 | 10/2007 | Kellogg |
| 2007/0249941 A1 | 10/2007 | Salehi et al. |
| 2007/0260234 A1 | 11/2007 | McCullagh et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0275348 A1 | 11/2007 | Lemon |
| 2007/0276419 A1 | 11/2007 | Rosenthal |
| 2007/0282333 A1 | 12/2007 | Fortson et al. |
| 2007/0282335 A1 | 12/2007 | Young et al. |
| 2007/0287933 A1 | 12/2007 | Phan et al. |
| 2007/0288055 A1 | 12/2007 | Lee |
| 2008/0009848 A1 | 1/2008 | Paraschiv et al. |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058585 A1 | 3/2008 | Novak et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097281 A1 | 4/2008 | Zusman et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0125768 A1 | 5/2008 | Tahara et al. |
| 2008/0140158 A1 | 6/2008 | Hamel et al. |
| 2008/0147058 A1 | 6/2008 | Horrell et al. |
| 2008/0147062 A1 | 6/2008 | Truckal et al. |
| 2008/0147092 A1 | 6/2008 | Rogge et al. |
| 2008/0171938 A1 | 7/2008 | Masuda et al. |
| 2008/0172051 A1 | 7/2008 | Masuda et al. |
| 2008/0177268 A1 | 7/2008 | Daum et al. |
| 2008/0188755 A1 | 8/2008 | Hart |
| 2008/0188878 A1 | 8/2008 | Young |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234708 A1 | 9/2008 | Houser et al. |
| 2008/0234709 A1 | 9/2008 | Houser |
| 2008/0234710 A1 | 9/2008 | Neurohr et al. |
| 2008/0234711 A1 | 9/2008 | Houser et al. |
| 2008/0243106 A1 | 10/2008 | Coe et al. |
| 2008/0243162 A1 | 10/2008 | Shibata et al. |
| 2008/0245371 A1 | 10/2008 | Gruber |
| 2008/0249553 A1 | 10/2008 | Gruber et al. |
| 2008/0255423 A1 | 10/2008 | Kondo et al. |
| 2008/0262490 A1 | 10/2008 | Williams |
| 2008/0281200 A1 | 11/2008 | Voic et al. |
| 2008/0281315 A1 | 11/2008 | Gines |
| 2008/0281322 A1 | 11/2008 | Sherman et al. |
| 2008/0287948 A1 | 11/2008 | Newton et al. |
| 2008/0294051 A1 | 11/2008 | Koshigoe et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0030311 A1 | 1/2009 | Stulen et al. |
| 2009/0030351 A1 | 1/2009 | Wiener et al. |
| 2009/0030437 A1 | 1/2009 | Houser et al. |
| 2009/0030438 A1 | 1/2009 | Stulen |
| 2009/0030439 A1 | 1/2009 | Stulen |
| 2009/0036911 A1 | 2/2009 | Stulen |
| 2009/0036912 A1 | 2/2009 | Wiener et al. |
| 2009/0036914 A1 | 2/2009 | Houser |
| 2009/0043228 A1 | 2/2009 | Northrop et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0069830 A1 | 3/2009 | Mulvihill et al. |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0105750 A1 | 4/2009 | Price et al. |
| 2009/0112229 A1 | 4/2009 | Omori et al. |
| 2009/0118751 A1 | 5/2009 | Wiener et al. |
| 2009/0118802 A1 | 5/2009 | Mioduski et al. |
| 2009/0138006 A1 | 5/2009 | Bales et al. |
| 2009/0143678 A1 | 6/2009 | Keast et al. |
| 2009/0143795 A1 | 6/2009 | Robertson |
| 2009/0143796 A1 | 6/2009 | Stulen et al. |
| 2009/0143797 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0143806 A1 | 6/2009 | Witt et al. |
| 2009/0149801 A1 | 6/2009 | Crandall et al. |
| 2009/0163807 A1 | 6/2009 | Sliwa |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0207923 A1 | 8/2009 | Dress |
| 2009/0216157 A1 | 8/2009 | Yamada |
| 2009/0223033 A1 | 9/2009 | Houser |
| 2009/0248021 A1 | 10/2009 | McKenna |
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0275940 A1 | 11/2009 | Malackowski et al. |
| 2009/0287205 A1 | 11/2009 | Ingle |
| 2009/0299141 A1 | 12/2009 | Downey et al. |
| 2009/0318945 A1 | 12/2009 | Yoshimine et al. |
| 2009/0327715 A1 | 12/2009 | Smith et al. |
| 2010/0004508 A1 | 1/2010 | Naito et al. |

(56) References Cited

U.S. PATENT DOCUMENTS

| | | |
|---|---|---|
| 2010/0004668 A1 | 1/2010 | Smith et al. |
| 2010/0004669 A1 | 1/2010 | Smith et al. |
| 2010/0016785 A1 | 1/2010 | Takuma |
| 2010/0016852 A1 | 1/2010 | Manzo et al. |
| 2010/0022825 A1 | 1/2010 | Yoshie |
| 2010/0030233 A1 | 2/2010 | Whitman et al. |
| 2010/0030248 A1 | 2/2010 | Palmer et al. |
| 2010/0034605 A1 | 2/2010 | Huckins et al. |
| 2010/0036370 A1 | 2/2010 | Mirel et al. |
| 2010/0042077 A1 | 2/2010 | Okada |
| 2010/0042126 A1 | 2/2010 | Houser et al. |
| 2010/0049180 A1 | 2/2010 | Wells et al. |
| 2010/0057118 A1 | 3/2010 | Dietz et al. |
| 2010/0063525 A1 | 3/2010 | Beaupre et al. |
| 2010/0063528 A1 | 3/2010 | Beaupre |
| 2010/0069940 A1 | 3/2010 | Miller et al. |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanal et al. |
| 2010/0179577 A1 | 7/2010 | Houser |
| 2010/0181966 A1 | 7/2010 | Sakakibara |
| 2010/0187283 A1 | 7/2010 | Crainich et al. |
| 2010/0193567 A1 | 8/2010 | Scheib et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228191 A1 | 9/2010 | Alvarez et al. |
| 2010/0228264 A1 | 9/2010 | Robinson et al. |
| 2010/0234906 A1 | 9/2010 | Koh |
| 2010/0262134 A1 | 10/2010 | Jensen et al. |
| 2010/0268211 A1 | 10/2010 | Manwaring et al. |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0280407 A1 | 11/2010 | Polster |
| 2010/0292691 A1 | 11/2010 | Brogna |
| 2010/0298743 A1 | 11/2010 | Nield et al. |
| 2010/0298851 A1 | 11/2010 | Nleld |
| 2010/0312186 A1 | 12/2010 | Suchdev et al. |
| 2010/0331742 A1 | 12/2010 | Masuda |
| 2010/0331869 A1 | 12/2010 | Voegele et al. |
| 2010/0331870 A1 | 12/2010 | Wan et al. |
| 2010/0331871 A1 | 12/2010 | Nield et al. |
| 2010/0331872 A1 | 12/2010 | Houser et al. |
| 2010/0331873 A1 | 12/2010 | Dannaher et al. |
| 2011/0004233 A1 | 1/2011 | Muir et al. |
| 2011/0009850 A1 | 1/2011 | Main |
| 2011/0015627 A1 | 1/2011 | DiNardo et al. |
| 2011/0015631 A1 | 1/2011 | Wiener et al. |
| 2011/0015660 A1 | 1/2011 | Wiener et al. |
| 2011/0028964 A1 | 2/2011 | Edwards |
| 2011/0077648 A1 | 3/2011 | Lee et al. |
| 2011/0082486 A1 | 4/2011 | Messerly et al. |
| 2011/0087212 A1 | 4/2011 | Aldridge et al. |
| 2011/0087213 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087218 A1 | 4/2011 | Boudreaux et al. |
| 2011/0087220 A1 | 4/2011 | Felder et al. |
| 2011/0087256 A1 | 4/2011 | Wiener et al. |
| 2011/0106141 A1 | 5/2011 | Nakamura |
| 2011/0112526 A1 | 5/2011 | Fritz et al. |
| 2011/0125151 A1 | 5/2011 | Strauss et al. |
| 2011/0144806 A1 | 6/2011 | Sandhu et al. |
| 2011/0196286 A1 | 8/2011 | Robertson et al. |
| 2011/0196287 A1 | 8/2011 | Robertson et al. |
| 2011/0196398 A1 | 8/2011 | Robertson et al. |
| 2011/0196399 A1 | 8/2011 | Robertson et al. |
| 2011/0196400 A1 | 8/2011 | Robertson et al. |
| 2011/0196401 A1 | 8/2011 | Robertson et al. |
| 2011/0196402 A1 | 8/2011 | Robertson et al. |
| 2011/0196403 A1 | 8/2011 | Robertson et al. |
| 2011/0196404 A1 | 8/2011 | Dietz et al. |
| 2011/0196405 A1 | 8/2011 | Dietz |
| 2011/0224689 A1 | 9/2011 | Larkin et al. |
| 2011/0238065 A1 | 9/2011 | Hunt et al. |
| 2011/0257650 A1 | 10/2011 | Deville et al. |
| 2011/0270126 A1 | 11/2011 | Gunday et al. |
| 2011/0276049 A1 | 11/2011 | Gerhardt |
| 2011/0278343 A1 | 11/2011 | Knodel et al. |
| 2011/0284014 A1 | 11/2011 | Cadeddu et al. |
| 2011/0288452 A1 | 11/2011 | Houser et al. |
| 2011/0290853 A1 | 12/2011 | Shelton, IV et al. |
| 2011/0290856 A1 | 12/2011 | Shelton, IV et al. |
| 2011/0291526 A1 | 12/2011 | Abramovich et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022525 A1 | 1/2012 | Dietz et al. |
| 2012/0022526 A1 | 1/2012 | Aldridge et al. |
| 2012/0022530 A1 | 1/2012 | Woodruff et al. |
| 2012/0022583 A1 | 1/2012 | Sugalski et al. |
| 2012/0029546 A1 | 2/2012 | Robertson |
| 2012/0041358 A1 | 2/2012 | Mann et al. |
| 2012/0059289 A1 | 3/2012 | Nield et al. |
| 2012/0065628 A1 | 3/2012 | Naito |
| 2012/0071863 A1 | 3/2012 | Lee et al. |
| 2012/0078139 A1 | 3/2012 | Aldridge et al. |
| 2012/0078243 A1 | 3/2012 | Worrell et al. |
| 2012/0078244 A1 | 3/2012 | Worrell et al. |
| 2012/0078247 A1 | 3/2012 | Worrell et al. |
| 2012/0078249 A1 | 3/2012 | Eichmann et al. |
| 2012/0078278 A1 | 3/2012 | Bales, Jr. et al. |
| 2012/0080332 A1 | 4/2012 | Shelton, IV et al. |
| 2012/0083783 A1 | 4/2012 | Davison et al. |
| 2012/0083784 A1 | 4/2012 | Davison et al. |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116379 A1 | 5/2012 | Yates et al. |
| 2012/0116391 A1 | 5/2012 | Houser et al. |
| 2012/0116394 A1 | 5/2012 | Timm et al. |
| 2012/0116395 A1 | 5/2012 | Madan et al. |
| 2012/0130256 A1 | 5/2012 | Buysse et al. |
| 2012/0130365 A1 | 5/2012 | McLawhorn |
| 2012/0132450 A1 | 5/2012 | Timm et al. |
| 2012/0136279 A1 | 5/2012 | Tanaka et al. |
| 2012/0136354 A1 | 5/2012 | Rupp |
| 2012/0138660 A1 | 6/2012 | Shelton, IV |
| 2012/0143211 A1 | 6/2012 | Kishi |
| 2012/0143233 A1 | 6/2012 | Sinelnikov |
| 2012/0150170 A1 | 6/2012 | Buysse et al. |
| 2012/0165816 A1 | 6/2012 | Kersten et al. |
| 2012/0172873 A1 | 7/2012 | Artale et al. |
| 2012/0172904 A1 | 7/2012 | Muir et al. |
| 2012/0177005 A1 | 7/2012 | Liang et al. |
| 2012/0184946 A1 | 7/2012 | Price et al. |
| 2012/0199630 A1 | 8/2012 | Shelton, IV |
| 2012/0199631 A1 | 8/2012 | Shelton, IV et al. |
| 2012/0199632 A1 | 8/2012 | Spivey et al. |
| 2012/0199633 A1 | 8/2012 | Shelton, IV et al. |
| 2012/0203247 A1 | 8/2012 | Shelton, IV et al. |
| 2012/0203257 A1 | 8/2012 | Stulen et al. |
| 2012/0205421 A1 | 8/2012 | Shelton, IV |
| 2012/0209289 A1 | 8/2012 | Duque et al. |
| 2012/0209303 A1 | 8/2012 | Frankhouser et al. |
| 2012/0210223 A1 | 8/2012 | Eppolito |
| 2012/0211546 A1 | 8/2012 | Shelton, IV |
| 2012/0245582 A1 | 9/2012 | Kimball et al. |
| 2012/0259353 A1 | 10/2012 | Houser et al. |
| 2012/0265196 A1 | 10/2012 | Turner et al. |
| 2012/0265241 A1 | 10/2012 | Hart et al. |
| 2012/0269676 A1 | 10/2012 | Houser et al. |

(56)         References Cited

U.S. PATENT DOCUMENTS

| | | |
|---|---|---|
| 2012/0289984 A1 | 11/2012 | Houser et al. |
| 2012/0296371 A1 | 11/2012 | Kappus et al. |
| 2012/0310262 A1 | 12/2012 | Messerly et al. |
| 2012/0310263 A1 | 12/2012 | Messerly et al. |
| 2012/0310264 A1 | 12/2012 | Messerly et al. |
| 2012/0323265 A1 | 12/2012 | Stulen |
| 2012/0330307 A1 | 12/2012 | Ladtkaw et al. |
| 2012/0330338 A1 | 12/2012 | Messerly |
| 2013/0012957 A1 | 1/2013 | Shelton, IV et al. |
| 2013/0012970 A1 | 1/2013 | Houser |
| 2013/0023925 A1 | 1/2013 | Mueller |
| 2013/0030433 A1 | 1/2013 | Heard |
| 2013/0035680 A1 | 2/2013 | Ben-Haim et al. |
| 2013/0035685 A1 | 2/2013 | Fischer et al. |
| 2013/0053840 A1 | 2/2013 | Krapohl et al. |
| 2013/0072856 A1 | 3/2013 | Frankhouser et al. |
| 2013/0072857 A1 | 3/2013 | Frankhouser et al. |
| 2013/0079762 A1 | 3/2013 | Twomey et al. |
| 2013/0090576 A1 | 4/2013 | Stulen et al. |
| 2013/0103023 A1 | 4/2013 | Monson et al. |
| 2013/0103024 A1 | 4/2013 | Monson et al. |
| 2013/0110145 A1 | 5/2013 | Weitzman |
| 2013/0116717 A1 | 5/2013 | Balek et al. |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0123822 A1 | 5/2013 | Wellman et al. |
| 2013/0131660 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0211397 A1 | 8/2013 | Parihar et al. |
| 2013/0217967 A1 | 8/2013 | Mohr et al. |
| 2013/0226207 A1 | 8/2013 | Stulen et al. |
| 2013/0226208 A1 | 8/2013 | Wiener et al. |
| 2013/0231691 A1 | 9/2013 | Houser |
| 2013/0245659 A1 | 9/2013 | Robertson et al. |
| 2013/0253256 A1 | 9/2013 | Griffith et al. |
| 2013/0267975 A1 | 10/2013 | Timm et al. |
| 2013/0274734 A1 | 10/2013 | Maass et al. |
| 2013/0277410 A1 | 10/2013 | Fernandez et al. |
| 2013/0282003 A1 | 10/2013 | Messerly et al. |
| 2013/0285758 A1 | 10/2013 | Aldridge et al. |
| 2013/0289591 A1 | 10/2013 | Boudreaux et al. |
| 2013/0296843 A1 | 11/2013 | Boudreaux et al. |
| 2013/0296908 A1 | 11/2013 | Shulte et al. |
| 2013/0331873 A1 | 12/2013 | Ross et al. |
| 2013/0338661 A1 | 12/2013 | Behnke, II |
| 2013/0345689 A1 | 12/2013 | Ruddenklau et al. |
| 2013/0345733 A1 | 12/2013 | Robertson et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005654 A1 | 1/2014 | Batross et al. |
| 2014/0005656 A1 | 1/2014 | Mucilli et al. |
| 2014/0005661 A1 | 1/2014 | Shelton, IV et al. |
| 2014/0005662 A1 | 1/2014 | Shelton, IV et al. |
| 2014/0005667 A1 | 1/2014 | Stulen et al. |
| 2014/0005668 A1 | 1/2014 | Rhee et al. |
| 2014/0005676 A1 | 1/2014 | Shelton, IV et al. |
| 2014/0005678 A1 | 1/2014 | Shelton, IV et al. |
| 2014/0005680 A1 | 1/2014 | Shelton, IV et al. |
| 2014/0005681 A1 | 1/2014 | Gee et al. |
| 2014/0005682 A1 | 1/2014 | Worrell et al. |
| 2014/0005701 A1 | 1/2014 | Olson et al. |
| 2014/0005702 A1 | 1/2014 | Timm et al. |
| 2014/0005703 A1 | 1/2014 | Stulen et al. |
| 2014/0005704 A1 | 1/2014 | Vakharia et al. |
| 2014/0005705 A1 | 1/2014 | Weir et al. |
| 2014/0005708 A1 | 1/2014 | Shelton, IV et al. |
| 2014/0005718 A1 | 1/2014 | Shelton, IV et al. |
| 2014/0012299 A1 | 1/2014 | Stoddard et al. |
| 2014/0014544 A1 | 1/2014 | Bugnard et al. |
| 2014/0058427 A1 | 2/2014 | Robertson |
| 2014/0066962 A1 | 3/2014 | Robertson et al. |
| 2014/0081299 A1 | 3/2014 | Dietz et al. |
| 2014/0087569 A1 | 3/2014 | Lee |
| 2014/0107538 A1 | 4/2014 | Wiener et al. |
| 2014/0114327 A1 | 4/2014 | Boudreaux et al. |
| 2014/0114334 A1 | 4/2014 | Olson et al. |
| 2014/0121569 A1 | 5/2014 | Schafer et al. |
| 2014/0135663 A1 | 5/2014 | Funakubo et al. |
| 2014/0135804 A1 | 5/2014 | Weisenburgh, II et al. |
| 2014/0155921 A1 | 6/2014 | Price et al. |
| 2014/0180280 A1 | 6/2014 | Sigmon, Jr. |
| 2014/0194874 A1 | 7/2014 | Dietz et al. |
| 2014/0194875 A1 | 7/2014 | Reschke et al. |
| 2014/0207135 A1 | 7/2014 | Winter |
| 2014/0207163 A1 | 7/2014 | Eichmann et al. |
| 2014/0243864 A1 | 8/2014 | Voegele et al. |
| 2014/0276738 A1 | 9/2014 | Price et al. |
| 2014/0276970 A1 | 9/2014 | Messerly et al. |
| 2014/0323926 A1 | 10/2014 | Akagane |
| 2014/0330271 A1 | 11/2014 | Dietz et al. |
| 2014/0371735 A1 | 12/2014 | Long |
| 2015/0011889 A1 | 1/2015 | Lef |
| 2015/0080876 A1 | 3/2015 | Worrell et al. |
| 2015/0083774 A1 | 3/2015 | Measamer et al. |
| 2015/0088178 A1 | 3/2015 | Stulen et al. |
| 2015/0112335 A1 | 4/2015 | Boudreaux et al. |
| 2015/0148830 A1 | 5/2015 | Stulen et al. |
| 2015/0157356 A1 | 6/2015 | Gee |
| 2015/0164533 A1 | 6/2015 | Felder et al. |
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0164538 A1 | 6/2015 | Aldridge et al. |
| 2015/0182276 A1 | 7/2015 | Wiener et al. |
| 2015/0182277 A1 | 7/2015 | Wiener et al. |
| 2015/0230853 A1 | 8/2015 | Johnson et al. |
| 2015/0230861 A1 | 8/2015 | Woloszko et al. |
| 2015/0250495 A1 | 9/2015 | Robertson et al. |
| 2015/0257780 A1 | 9/2015 | Houser |
| 2015/0272659 A1 | 10/2015 | Boudreaux et al. |
| 2015/0272660 A1 | 10/2015 | Boudreaux et al. |
| 2015/0289854 A1 | 10/2015 | Cho et al. |
| 2015/0340586 A1 | 11/2015 | Wiener et al. |
| 2016/0045248 A1 | 2/2016 | Unger et al. |
| 2016/0051316 A1 | 2/2016 | Boudreaux |
| 2016/0051317 A1 | 2/2016 | Boudreaux |
| 2016/0058492 A1 | 3/2016 | Yates et al. |
| 2016/0074108 A1 | 3/2016 | Woodruff et al. |
| 2016/0114355 A1 | 4/2016 | Sakai et al. |
| 2016/0121143 A1 | 5/2016 | Mumaw et al. |
| 2016/0128762 A1 | 5/2016 | Harris et al. |
| 2016/0128769 A1 | 5/2016 | Rontal et al. |
| 2016/0144204 A1 | 5/2016 | Akagane |
| 2016/0157927 A1 | 6/2016 | Corbett et al. |
| 2016/0175024 A1 | 6/2016 | Yates et al. |
| 2016/0175029 A1 | 6/2016 | Witt et al. |
| 2016/0175031 A1 | 6/2016 | Boudreaux |
| 2016/0175032 A1 | 6/2016 | Yang |
| 2016/0199123 A1 | 7/2016 | Thomas et al. |
| 2016/0199125 A1 | 7/2016 | Jones |
| 2016/0206342 A1 | 7/2016 | Robertson et al. |
| 2016/0213395 A1 | 7/2016 | Anim |
| 2016/0228171 A1 | 8/2016 | Boudreaux |
| 2016/0240768 A1 | 8/2016 | Fujii et al. |
| 2016/0262786 A1 | 9/2016 | Madan et al. |
| 2016/0270840 A1 | 9/2016 | Yates et al. |
| 2016/0270841 A1 | 9/2016 | Strobl et al. |
| 2016/0270842 A1 | 9/2016 | Strobl et al. |
| 2016/0270843 A1 | 9/2016 | Boudreaux et al. |
| 2016/0278848 A1 | 9/2016 | Boudreaux et al. |
| 2016/0296249 A1 | 10/2016 | Robertson |
| 2016/0296250 A1 | 10/2016 | Olson et al. |
| 2016/0296251 A1 | 10/2016 | Olson et al. |
| 2016/0296252 A1 | 10/2016 | Olson et al. |
| 2016/0296268 A1 | 10/2016 | Gee et al. |
| 2016/0296270 A1 | 10/2016 | Strobl et al. |
| 2016/0296271 A1 | 10/2016 | Danziger et al. |
| 2016/0302844 A1 | 10/2016 | Strobl et al. |

(56) References Cited

U.S. PATENT DOCUMENTS

| | | |
|---|---|---|
| 2016/0317217 A1 | 11/2016 | Batross et al. |
| 2016/0338726 A1 | 11/2016 | Stulen et al. |
| 2016/0346001 A1 | 12/2016 | Vakharia et al. |
| 2016/0367273 A1 | 12/2016 | Robertson et al. |
| 2016/0367281 A1 | 12/2016 | Gee et al. |
| 2016/0374708 A1 | 12/2016 | Wiener et al. |
| 2016/0374709 A1 | 12/2016 | Timm et al. |
| 2016/0374712 A1 | 12/2016 | Stulen et al. |
| 2017/0000512 A1 | 1/2017 | Conlon et al. |
| 2017/0000513 A1 | 1/2017 | Conlon et al. |
| 2017/0000541 A1 | 1/2017 | Yates et al. |
| 2017/0027624 A1 | 2/2017 | Wilson et al. |
| 2017/0036044 A1 | 2/2017 | Ito |
| 2017/0056058 A1 | 3/2017 | Voegele et al. |
| 2017/0086876 A1 | 3/2017 | Wiener et al. |
| 2017/0086908 A1 | 3/2017 | Wiener et al. |
| 2017/0086909 A1 | 3/2017 | Yates et al. |
| 2017/0086910 A1 | 3/2017 | Wiener et al. |
| 2017/0086911 A1 | 3/2017 | Wiener et al. |
| 2017/0086912 A1 | 3/2017 | Wiener et al. |
| 2017/0086913 A1 | 3/2017 | Yates et al. |
| 2017/0086914 A1 | 3/2017 | Wiener et al. |
| 2017/0090507 A1 | 3/2017 | Wiener et al. |
| 2017/0095267 A1 | 4/2017 | Messerly et al. |
| 2017/0105757 A1 | 4/2017 | Weir et al. |
| 2017/0105786 A1 | 4/2017 | Scheib et al. |
| 2017/0105791 A1 | 4/2017 | Yates et al. |
| 2017/0119426 A1 | 5/2017 | Akagane |
| 2017/0135751 A1 | 5/2017 | Rothweller et al. |
| 2017/0143371 A1 | 5/2017 | Witt et al. |
| 2017/0143877 A1 | 5/2017 | Witt et al. |
| 2017/0164972 A1 | 6/2017 | Johnson et al. |
| 2017/0172700 A1 | 6/2017 | Denzinger et al. |
| 2017/0189095 A1 | 7/2017 | Danziger et al. |
| 2017/0189096 A1 | 7/2017 | Danziger et al. |
| 2017/0189101 A1 | 7/2017 | Yates et al. |
| 2017/0196586 A1 | 7/2017 | Witt et al. |
| 2017/0196587 A1 | 7/2017 | Witt et al. |
| 2017/0202570 A1 | 7/2017 | Shelton, IV et al. |
| 2017/0202571 A1 | 7/2017 | Shelton, IV et al. |
| 2017/0202572 A1 | 7/2017 | Shelton, IV et al. |
| 2017/0202591 A1 | 7/2017 | Shelton, IV et al. |
| 2017/0202592 A1 | 7/2017 | Shelton, IV et al. |
| 2017/0202593 A1 | 7/2017 | Shelton, IV et al. |
| 2017/0202594 A1 | 7/2017 | Shelton, IV et al. |
| 2017/0202595 A1 | 7/2017 | Shelton, IV |
| 2017/0202596 A1 | 7/2017 | Shelton, IV et al. |
| 2017/0202597 A1 | 7/2017 | Shelton, IV et al. |
| 2017/0202598 A1 | 7/2017 | Shelton, IV et al. |
| 2017/0202599 A1 | 7/2017 | Shelton, IV et al. |
| 2017/0202605 A1 | 7/2017 | Shelton, IV et al. |
| 2017/0202607 A1 | 7/2017 | Shelton, IV et al. |
| 2017/0202608 A1 | 7/2017 | Shelton, IV et al. |
| 2017/0202609 A1 | 7/2017 | Shelton, IV et al. |
| 2017/0207467 A1 | 7/2017 | Shelton, IV et al. |
| 2017/0209167 A1 | 7/2017 | Nield |
| 2017/0238991 A1 | 8/2017 | Worrell et al. |
| 2017/0245875 A1 | 8/2017 | Timm et al. |
| 2018/0014845 A1 | 1/2018 | Dannaher |
| 2018/0014846 A1 | 1/2018 | Rhee et al. |
| 2018/0014848 A1 | 1/2018 | Messerly et al. |
| 2018/0042634 A1 | 2/2018 | Conlon et al. |
| 2018/0049767 A1 | 2/2018 | Gee et al. |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0056095 A1 | 3/2018 | Messerly et al. |
| 2018/0078268 A1 | 3/2018 | Messerly et al. |
| 2018/0092660 A1 | 4/2018 | Houser et al. |
| 2018/0125523 A1 | 5/2018 | Johnson |
| 2018/0146975 A1 | 5/2018 | Zhang |
| 2018/0168680 A1 | 6/2018 | Houser et al. |
| 2018/0199957 A1 | 7/2018 | Robertson et al. |
| 2018/0206881 A1 | 7/2018 | Price et al. |
| 2018/0221049 A1 | 8/2018 | Faller et al. |
| 2018/0263653 A1 | 9/2018 | Witt et al. |
| 2019/0053822 A1 | 2/2019 | Robertson et al. |
| 2019/0239919 A1 | 8/2019 | Witt et al. |
| 2019/0262029 A1 | 8/2019 | Messerly et al. |
| 2019/0350615 A1 | 11/2019 | Messerly et al. |
| 2019/0380733 A1 | 12/2019 | Stulen et al. |
| 2019/0381340 A1 | 12/2019 | Voegele et al. |
| 2020/0008857 A1 | 1/2020 | Conlon et al. |
| 2020/0015798 A1 | 1/2020 | Wiener et al. |
| 2020/0015838 A1 | 1/2020 | Robertson |
| 2020/0046401 A1 | 2/2020 | Witt et al. |
| 2020/0054386 A1 | 2/2020 | Houser et al. |
| 2020/0085462 A1 | 3/2020 | Robertson |
| 2020/0085466 A1 | 3/2020 | Faller et al. |
| 2020/0323551 A1 | 10/2020 | Faller et al. |
| 2021/0038248 A1 | 2/2021 | Houser |
| 2021/0121197 A1 | 4/2021 | Houser et al. |
| 2021/0128191 A1 | 5/2021 | Messerly et al. |
| 2021/0145531 A1 | 5/2021 | Gee et al. |
| 2021/0236157 A1 | 8/2021 | Rhee et al. |
| 2021/0315605 A1 | 10/2021 | Gee et al. |
| 2021/0378700 A1 | 12/2021 | Houser |

FOREIGN PATENT DOCUMENTS

| | | | |
|---|---|---|---|
| CA | 2535467 | A1 | 4/1993 |
| CA | 2214413 | A1 | 9/1996 |
| CN | 1233944 | A | 11/1999 |
| CN | 1253485 | A | 5/2000 |
| CN | 2460047 | Y | 11/2001 |
| CN | 1634601 | A | 7/2005 |
| CN | 1640365 | A | 7/2005 |
| CN | 1694649 | A | 11/2005 |
| CN | 1775323 | A | 5/2006 |
| CN | 1922563 | A | 2/2007 |
| CN | 2868227 | Y | 2/2007 |
| CN | 1951333 | A | 4/2007 |
| CN | 101035482 | A | 9/2007 |
| CN | 101040799 | A | 9/2007 |
| CN | 101396300 | A | 4/2009 |
| CN | 101467917 | A | 7/2009 |
| CN | 101674782 | A | 3/2010 |
| CN | 101883531 | A | 11/2010 |
| CN | 102160045 | A | 8/2011 |
| CN | 202027624 | U | 11/2011 |
| CN | 102335778 | A | 2/2012 |
| CN | 102834069 | A | 12/2012 |
| CN | 101313865 | B | 1/2013 |
| CN | 103668171 | A | 3/2014 |
| CN | 103921215 | A | 7/2014 |
| CN | 106077718 | A | 11/2016 |
| DE | 2065681 | A1 | 3/1975 |
| DE | 3904558 | A1 | 8/1990 |
| DE | 9210327 | U1 | 11/1992 |
| DE | 4300307 | A1 | 7/1994 |
| DE | 4323585 | A1 | 1/1995 |
| DE | 4434938 | C1 | 2/1996 |
| DE | 19608716 | C1 | 4/1997 |
| DE | 29623113-01 | | 10/1997 |
| DE | 20004812 | U1 | 9/2000 |
| DE | 20021619 | U1 | 3/2001 |
| DE | 10042606 | A1 | 8/2001 |
| DE | 10201569 | A1 | 7/2003 |
| EP | 0171967 | A2 | 2/1986 |
| EP | 0336742 | A2 | 10/1989 |
| EP | 0136855-81 | | 11/1989 |
| EP | 0342448 | A1 | 11/1989 |
| EP | 0443256 | A1 | 8/1991 |
| EP | 0456470 | A1 | 11/1991 |
| EP | 0482195 | B1 | 4/1992 |
| EP | 0238667 | B1 | 2/1993 |
| EP | 0340803 | B1 | 8/1993 |
| EP | 0598976 | A2 | 6/1994 |
| EP | 0630612 | A1 | 12/1994 |
| EP | 0424685 | B1 | 5/1995 |
| EP | 0677275 | A2 | 10/1995 |
| EP | 0695535 | A1 | 2/1996 |
| EP | 0705571 | A1 | 4/1996 |

(56)　　　　　References Cited

FOREIGN PATENT DOCUMENTS

| | | | |
|---|---|---|---|
| EP | 0741996 | B1 | 11/1996 |
| EP | 0612570 | B1 | 6/1997 |
| EP | 0557806 | B1 | 5/1998 |
| EP | 0640317 | B1 | 9/1999 |
| EP | 1108394 | A2 | 6/2001 |
| EP | 1502551 | B1 | 7/2001 |
| EP | 1138264 | A1 | 10/2001 |
| EP | 0908148 | B1 | 1/2002 |
| EP | 1229515 | A2 | 8/2002 |
| EP | 0722696 | B1 | 12/2002 |
| EP | 1285634 | A1 | 2/2003 |
| EP | 0908155 | B1 | 6/2003 |
| EP | 0705570 | B1 | 4/2004 |
| EP | 0765637 | B1 | 7/2004 |
| EP | 1543854 | A1 | 6/2005 |
| EP | 0870473 | B1 | 9/2005 |
| EP | 0624346 | B1 | 11/2005 |
| EP | 1594209 | A1 | 11/2005 |
| EP | 1199044 | B1 | 12/2005 |
| EP | 1609428 | A1 | 12/2005 |
| EP | 1199043 | B1 | 3/2006 |
| EP | 1293172 | B1 | 4/2006 |
| EP | 0875209 | B1 | 5/2006 |
| EP | 1433425 | B1 | 6/2006 |
| EP | 1256323 | B1 | 8/2006 |
| EP | 1698289 | A2 | 9/2006 |
| EP | 1704824 | A1 | 9/2006 |
| EP | 1749479 | A1 | 2/2007 |
| EP | 1767157 | A1 | 3/2007 |
| EP | 1254637 | B1 | 8/2007 |
| EP | 1815950 | A1 | 8/2007 |
| EP | 1839599 | A1 | 10/2007 |
| EP | 1844720 | A1 | 10/2007 |
| EP | 1862133 | A1 | 12/2007 |
| EP | 1875875 | A1 | 1/2008 |
| EP | 1878399 | A1 | 1/2008 |
| EP | 1915953 | A1 | 4/2008 |
| EP | 1532933 | B1 | 5/2008 |
| EP | 1199045 | B1 | 6/2008 |
| EP | 1707143 | B1 | 6/2008 |
| EP | 1943957 | A2 | 7/2008 |
| EP | 1964530 | A1 | 9/2008 |
| EP | 1972264 | A1 | 9/2008 |
| EP | 1974771 | A1 | 10/2008 |
| EP | 1435852 | B1 | 12/2008 |
| EP | 1498082 | B1 | 12/2008 |
| EP | 1707131 | B1 | 12/2008 |
| EP | 1477104 | B1 | 1/2009 |
| EP | 2014218 | A2 | 1/2009 |
| EP | 1849424 | B1 | 4/2009 |
| EP | 2042112 | A2 | 4/2009 |
| EP | 2042117 | A1 | 4/2009 |
| EP | 2060238 | A1 | 5/2009 |
| EP | 1832259 | B1 | 6/2009 |
| EP | 2074959 | A1 | 7/2009 |
| EP | 1810625 | B1 | 8/2009 |
| EP | 2090256 | A2 | 8/2009 |
| EP | 2092905 | A1 | 8/2009 |
| EP | 2105104 | A2 | 9/2009 |
| EP | 1747761 | B1 | 10/2009 |
| EP | 2106758 | A1 | 10/2009 |
| EP | 2111813 | A1 | 10/2009 |
| EP | 2131760 | A1 | 12/2009 |
| EP | 1769766 | B1 | 2/2010 |
| EP | 2151204 | A1 | 2/2010 |
| EP | 2153791 | A1 | 2/2010 |
| EP | 2200145 | A1 | 6/2010 |
| EP | 1214913 | B1 | 7/2010 |
| EP | 2238938 | A1 | 10/2010 |
| EP | 2243439 | A1 | 10/2010 |
| EP | 2298154 | A2 | 3/2011 |
| EP | 2305144 | A1 | 4/2011 |
| EP | 1510178 | B1 | 6/2011 |
| EP | 1946708 | B1 | 6/2011 |
| EP | 2335630 | A1 | 6/2011 |
| EP | 1728475 | B1 | 8/2011 |
| EP | 2353518 | A1 | 8/2011 |
| EP | 2361562 | A1 | 8/2011 |
| EP | 2365608 | A2 | 9/2011 |
| EP | 2420197 | A2 | 2/2012 |
| EP | 2422721 | A2 | 2/2012 |
| EP | 1927321 | B1 | 4/2012 |
| EP | 2529681 | A1 | 12/2012 |
| EP | 1767164 | B1 | 1/2013 |
| EP | 2316359 | B1 | 3/2013 |
| EP | 2090238 | B1 | 4/2013 |
| EP | 2578172 | A2 | 4/2013 |
| EP | 1586275 | B1 | 5/2013 |
| EP | 1616529 | B1 | 9/2013 |
| EP | 1997438 | B1 | 11/2013 |
| EP | 2508143 | B1 | 2/2014 |
| EP | 2583633 | B1 | 10/2014 |
| EP | 2113210 | B1 | 3/2016 |
| EP | 2510891 | B1 | 6/2016 |
| EP | 2227155 | B1 | 7/2016 |
| EP | 2859858 | B1 | 12/2016 |
| ES | 2115068 | T3 | 6/1998 |
| FR | 2454351 | A1 | 11/1980 |
| FR | 2964554 | A1 | 3/2012 |
| GB | 1482943 | A | 8/1977 |
| GB | 2032221 | A | 4/1980 |
| GB | 2317566 | A | 4/1998 |
| GB | 2318298 | A | 4/1998 |
| GB | 2379878 | B | 11/2004 |
| GB | 2425480 | A | 11/2006 |
| GB | 2472216 | A | 2/2011 |
| GB | 2447767 | B | 8/2011 |
| JP | S50100891 | A | 8/1975 |
| JP | S5968513 | U | 5/1984 |
| JP | S59141938 | A | 8/1984 |
| JP | S62221343 | A | 9/1987 |
| JP | S62227343 | A | 10/1987 |
| JP | S62292153 | A | 12/1987 |
| JP | S62292154 | A | 12/1987 |
| JP | S63109386 | A | 5/1988 |
| JP | S63315049 | A | 12/1988 |
| JP | H01151452 | A | 6/1989 |
| JP | H01198540 | A | 8/1989 |
| JP | H0271510 | U | 5/1990 |
| JP | H02286149 | A | 11/1990 |
| JP | H02292193 | A | 12/1990 |
| JP | H0337061 | A | 2/1991 |
| JP | H0425707 | U | 2/1992 |
| JP | H0464351 | A | 2/1992 |
| JP | H0430508 | U | 3/1992 |
| JP | H04150847 | A | 5/1992 |
| JP | H04152942 | A | 5/1992 |
| JP | H04161078 | A | 6/1992 |
| JP | H0595955 | A | 4/1993 |
| JP | H05115490 | A | 5/1993 |
| JP | H0647048 | A | 2/1994 |
| JP | H0670938 | A | 3/1994 |
| JP | H06104503 | A | 4/1994 |
| JP | H06217988 | A | 8/1994 |
| JP | H06507081 | A | 8/1994 |
| JP | H 07500514 | A | 1/1995 |
| JP | H07185457 | A | 7/1995 |
| JP | 7-508910 | A | 10/1995 |
| JP | H07508910 | A | 10/1995 |
| JP | H07299415 | A | 11/1995 |
| JP | H07308323 | A | 11/1995 |
| JP | H0824266 | A | 1/1996 |
| JP | H08229050 | A | 9/1996 |
| JP | H08275950 | A | 10/1996 |
| JP | H08275951 | A | 10/1996 |
| JP | H08299351 | A | 11/1996 |
| JP | H08336544 | A | 12/1996 |
| JP | H08336545 | A | 12/1996 |
| JP | H09503146 | A | 3/1997 |
| JP | H09135553 | A | 5/1997 |
| JP | H09140722 | A | 6/1997 |
| JP | H105236 | A | 1/1998 |
| JP | H105237 | A | 1/1998 |
| JP | H10295700 | A | 11/1998 |

(56)                    References Cited

FOREIGN PATENT DOCUMENTS

| | | | |
|---|---|---|---|
| JP | H11501543 | A | 2/1999 |
| JP | H11128238 | A | 5/1999 |
| JP | H11192235 | A | 7/1999 |
| JP | H11253451 | A | 9/1999 |
| JP | H11318918 | A | 11/1999 |
| JP | 2000041991 | A | 2/2000 |
| JP | 2000070279 | A | 3/2000 |
| JP | 2000139943 | A | 5/2000 |
| JP | 2000210296 | A | 8/2000 |
| JP | 2000210299 | A | 8/2000 |
| JP | 2000271145 | A | 10/2000 |
| JP | 2000287987 | A | 10/2000 |
| JP | 2000312682 | A | 11/2000 |
| JP | 2001029353 | A | 2/2001 |
| JP | 2001502216 | A | 2/2001 |
| JP | 2001057985 | A | 3/2001 |
| JP | 2001170066 | A | 6/2001 |
| JP | 2001198137 | A | 7/2001 |
| JP | 2001309925 | A | 11/2001 |
| JP | 2002177295 | A | 6/2002 |
| JP | 2002186901 | A | 7/2002 |
| JP | 2002204808 | A | 7/2002 |
| JP | 2002233533 | A | 8/2002 |
| JP | 2002238919 | A | 8/2002 |
| JP | 2002263579 | A | 9/2002 |
| JP | 2002301086 | A | 10/2002 |
| JP | 2002306504 | A | 10/2002 |
| JP | 2002330977 | A | 11/2002 |
| JP | 2002542690 | A | 12/2002 |
| JP | 2003000612 | A | 1/2003 |
| JP | 2003010201 | A | 1/2003 |
| JP | 2003510158 | A | 3/2003 |
| JP | 2003116870 | A | 4/2003 |
| JP | 2003126104 | A | 5/2003 |
| JP | 2003126110 | A | 5/2003 |
| JP | 2003153919 | A | 5/2003 |
| JP | 2003230567 | A | 8/2003 |
| JP | 2003530921 | A | 10/2003 |
| JP | 2003310627 | A | 11/2003 |
| JP | 2003339730 | A | 12/2003 |
| JP | 2004129871 | A | 4/2004 |
| JP | 2004147701 | A | 5/2004 |
| JP | 2004209043 | A | 7/2004 |
| JP | 2005027026 | A | 1/2005 |
| JP | 2005040222 | A | 2/2005 |
| JP | 2005066316 | A | 3/2005 |
| JP | 2005074088 | A | 3/2005 |
| JP | 2005507679 | A | 3/2005 |
| JP | 2005094552 | A | 4/2005 |
| JP | 2005253674 | A | 9/2005 |
| JP | 2005534451 | A | 11/2005 |
| JP | 2006006410 | A | 1/2006 |
| JP | 2006512159 | A | 4/2006 |
| JP | 2006116194 | A | 5/2006 |
| JP | 2006158525 | A | 6/2006 |
| JP | 2006217716 | A | 8/2006 |
| JP | 2006218296 | A | 8/2006 |
| JP | 2006288431 | A | 10/2006 |
| JP | 3841627 | B2 | 11/2006 |
| JP | 2007050181 | A | 3/2007 |
| JP | 2007524459 | A | 8/2007 |
| JP | 2007229454 | A | 9/2007 |
| JP | 2007527747 | A | 10/2007 |
| JP | 2007296369 | A | 11/2007 |
| JP | 2008018226 | A | 1/2008 |
| JP | 2008036390 | A | 2/2008 |
| JP | 2008508065 | A | 3/2008 |
| JP | 2008119250 | A | 5/2008 |
| JP | 2008515562 | A | 5/2008 |
| JP | 2008521503 | A | 6/2008 |
| JP | D1339835 | S | 8/2008 |
| JP | 2008212679 | A | 9/2008 |
| JP | 2008536562 | A | 9/2008 |
| JP | 2008284374 | A | 11/2008 |
| JP | 2009511206 | A | 3/2009 |
| JP | 2009082711 | A | 4/2009 |
| JP | 2009517181 | A | 4/2009 |
| JP | 4262923 | B2 | 5/2009 |
| JP | 2009523567 | A | 6/2009 |
| JP | 2009148557 | A | 7/2009 |
| JP | 2009236177 | A | 10/2009 |
| JP | 2009254819 | A | 11/2009 |
| JP | 2009297352 | A | 12/2009 |
| JP | 2010000336 | A | 1/2010 |
| JP | 2010009686 | A | 1/2010 |
| JP | 2010514923 | A | 5/2010 |
| JP | 2010121865 | A | 6/2010 |
| JP | 2010534522 | A | 11/2010 |
| JP | 2010540186 | A | 12/2010 |
| JP | 2011505198 | A | 2/2011 |
| JP | 2011160586 | A | 8/2011 |
| JP | 2012075899 | A | 4/2012 |
| JP | 2012235658 | A | 11/2012 |
| JP | 5208761 | B2 | 6/2013 |
| JP | 5714508 | B2 | 5/2015 |
| JP | 2015515339 | A | 5/2015 |
| JP | 5836543 | B1 | 12/2015 |
| KR | 100789356 | B1 | 12/2007 |
| RU | 2154437 | C1 | 8/2000 |
| RU | 22035 | U1 | 3/2002 |
| RU | 2201169 | C2 | 3/2003 |
| RU | 2304934 | C2 | 8/2007 |
| RU | 2405603 | C1 | 12/2010 |
| SU | 850068 | A1 | 7/1981 |
| WO | WO-8103272 | A1 | 11/1981 |
| WO | 9222259 | A2 | 12/1992 |
| WO | 9307817 | A1 | 4/1993 |
| WO | WO-9308757 | A1 | 5/1993 |
| WO | WO-9314708 | A1 | 8/1993 |
| WO | 9316646 | A1 | 9/1993 |
| WO | 9320877 | A1 | 10/1993 |
| WO | 9322973 | A1 | 11/1993 |
| WO | 9400059 | A1 | 1/1994 |
| WO | WO-9421183 | A1 | 9/1994 |
| WO | WO-9424949 | A1 | 11/1994 |
| WO | 9509572 | A1 | 4/1995 |
| WO | 9510978 | A1 | 4/1995 |
| WO | 9534259 | A1 | 12/1995 |
| WO | 9630885 | A1 | 10/1996 |
| WO | 9635382 | A1 | 11/1996 |
| WO | WO-9639086 | A1 | 12/1996 |
| WO | 9710764 | A1 | 3/1997 |
| WO | WO-9800069 | A1 | 1/1998 |
| WO | WO-9805437 | A1 | 2/1998 |
| WO | 9816156 | A1 | 4/1998 |
| WO | WO-9816157 | A1 | 4/1998 |
| WO | 9826739 | A1 | 6/1998 |
| WO | 9835621 | A1 | 8/1998 |
| WO | 9837815 | A1 | 9/1998 |
| WO | 9840020 | A1 | 9/1998 |
| WO | 9847436 | A1 | 10/1998 |
| WO | 9857588 | A1 | 12/1998 |
| WO | 09902096 | A1 | 1/1999 |
| WO | WO-9920213 | A1 | 4/1999 |
| WO | WO-9923960 | A1 | 5/1999 |
| WO | 9940857 | A1 | 8/1999 |
| WO | 9940861 | A1 | 8/1999 |
| WO | 9952489 | A1 | 10/1999 |
| WO | 0024331 | A1 | 5/2000 |
| WO | 0025691 | A1 | 5/2000 |
| WO | WO-0024322 | A1 | 5/2000 |
| WO | WO-0024330 | A1 | 5/2000 |
| WO | WO-0064358 | A2 | 11/2000 |
| WO | 0074585 | A2 | 12/2000 |
| WO | 0124713 | A1 | 4/2001 |
| WO | WO-0128444 | A1 | 4/2001 |
| WO | WO-0132087 | A1 | 5/2001 |
| WO | 0154590 | A1 | 8/2001 |
| WO | WO-0167970 | A1 | 9/2001 |
| WO | WO-0195810 | A2 | 12/2001 |
| WO | 0224080 | A2 | 3/2002 |
| WO | 0238057 | A1 | 5/2002 |
| WO | 02062241 | A1 | 8/2002 |
| WO | 02080797 | A1 | 10/2002 |

(56) References Cited

FOREIGN PATENT DOCUMENTS

| WO | WO-02076685 A1 | 10/2002 |
| WO | WO-02080799 A1 | 10/2002 |
| WO | 03001986 A2 | 1/2003 |
| WO | 03013374 A1 | 2/2003 |
| WO | 03020339 A2 | 3/2003 |
| WO | 03028541 A2 | 4/2003 |
| WO | 03030708 A2 | 4/2003 |
| WO | 03068046 A2 | 8/2003 |
| WO | 03082133 A1 | 10/2003 |
| WO | 2004011037 A2 | 2/2004 |
| WO | 2004012615 A1 | 2/2004 |
| WO | 2004026104 A2 | 4/2004 |
| WO | 2004032754 A2 | 4/2004 |
| WO | 2004032762 A1 | 4/2004 |
| WO | 2004032763 A2 | 4/2004 |
| WO | WO-2004037095 A2 | 5/2004 |
| WO | 2004060141 A2 | 7/2004 |
| WO | WO-2004078051 A2 | 9/2004 |
| WO | WO-2004098426 A1 | 11/2004 |
| WO | 2004112618 A2 | 12/2004 |
| WO | 2005052959 A2 | 6/2005 |
| WO | WO-2005084250 A2 | 9/2005 |
| WO | 2005117735 A1 | 12/2005 |
| WO | 2005122917 A1 | 12/2005 |
| WO | 2006012797 A1 | 2/2006 |
| WO | 2006021269 A1 | 3/2006 |
| WO | 2006036706 A1 | 4/2006 |
| WO | 2006042210 A2 | 4/2006 |
| WO | 2006055166 A2 | 5/2006 |
| WO | 2006058223 A2 | 6/2006 |
| WO | 2006063199 A2 | 6/2006 |
| WO | 2006083988 A1 | 8/2006 |
| WO | 2006101661 A2 | 9/2006 |
| WO | 2006119139 A2 | 11/2006 |
| WO | 2006119376 A2 | 11/2006 |
| WO | 2006129465 A1 | 12/2006 |
| WO | 2007008703 A2 | 1/2007 |
| WO | WO-2007008710 A2 | 1/2007 |
| WO | 2007038538 A1 | 4/2007 |
| WO | 2007040818 A1 | 4/2007 |
| WO | 2007047380 A2 | 4/2007 |
| WO | 2007047531 A2 | 4/2007 |
| WO | 2007056590 A1 | 5/2007 |
| WO | 2007087272 A2 | 8/2007 |
| WO | 2007089724 A2 | 8/2007 |
| WO | 2007143665 A2 | 12/2007 |
| WO | 2008016886 A2 | 2/2008 |
| WO | 2008020964 A2 | 2/2008 |
| WO | 2008042021 A1 | 4/2008 |
| WO | 2008045348 A2 | 4/2008 |
| WO | 2008049084 A2 | 4/2008 |
| WO | 2008051764 A2 | 5/2008 |
| WO | 2008089174 A2 | 7/2008 |
| WO | 2008099529 A1 | 8/2008 |
| WO | 2008101356 A1 | 8/2008 |
| WO | WO-2008118709 A1 | 10/2008 |
| WO | WO-2008130793 A1 | 10/2008 |
| WO | 2009010565 A1 | 1/2009 |
| WO | 2009018067 A1 | 2/2009 |
| WO | 2009018406 A2 | 2/2009 |
| WO | 2009022614 A1 | 2/2009 |
| WO | 2009027065 A1 | 3/2009 |
| WO | 2009036818 A1 | 3/2009 |
| WO | 2009039179 A1 | 3/2009 |
| WO | 2009046234 A2 | 4/2009 |
| WO | 2009059741 A1 | 5/2009 |
| WO | 2009073402 A2 | 6/2009 |
| WO | 2009082477 A2 | 7/2009 |
| WO | 2009088550 A2 | 7/2009 |
| WO | 2009120992 A2 | 10/2009 |
| WO | 2009141616 A1 | 11/2009 |
| WO | 2009149234 A1 | 12/2009 |
| WO | 2010017149 A1 | 2/2010 |
| WO | 2010017266 A1 | 2/2010 |
| WO | 2010068783 A1 | 6/2010 |
| WO | WO-2010104755 A1 | 9/2010 |
| WO | WO-2011008672 A2 | 1/2011 |
| WO | 2011044338 A2 | 4/2011 |
| WO | WO-2011052939 A2 | 5/2011 |
| WO | WO-2011060031 A1 | 5/2011 |
| WO | 2011084768 A1 | 7/2011 |
| WO | 2011089717 A1 | 7/2011 |
| WO | 2011100321 A2 | 8/2011 |
| WO | 2011144911 A1 | 11/2011 |
| WO | 2012044597 A1 | 4/2012 |
| WO | WO-2012044606 A2 | 4/2012 |
| WO | 2012061722 A2 | 5/2012 |
| WO | WO-2012066983 A1 | 5/2012 |
| WO | 2012128362 A1 | 9/2012 |
| WO | 2012135705 A1 | 10/2012 |
| WO | 2012135721 A1 | 10/2012 |
| WO | 2012166510 A1 | 12/2012 |
| WO | 2013018934 A1 | 2/2013 |
| WO | 2013034629 A1 | 3/2013 |
| WO | WO-2013048963 A2 | 4/2013 |
| WO | 2013062978 A2 | 5/2013 |
| WO | 2013102602 A2 | 7/2013 |
| WO | 2013154157 A1 | 10/2013 |
| WO | 2014092108 A1 | 6/2014 |
| WO | 2015197395 A8 | 12/2015 |
| WO | 2016009921 A1 | 1/2016 |

OTHER PUBLICATIONS

Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Lim et al., "A Review of Mechanism Used in Laparoscopic Surgical Instruments," Mechanism and Machine Theory, vol. 38, pp. 1133-1147, (2003).
Gooch et al., "Recommended Infection-Control Practices for Dentistry, 1993," Published: May 28, 1993; [retrieved on Aug. 23, 2008]. Retrieved from the internet: URL: http//wonder.cdc.gov/wonder/prevguid/p0000191/p0000191.asp (15 pages).
Covidien Brochure, The LigaSure Precise™ Instrument, dated Mar. 2011 (2 pages).
AST Products, Inc., "Principles of Video Contact Angle Analysis," 20 pages, (2006).
Mitsui Chemicals Names DuPont™ Vespel® Business as Exclusive U.S., European Distributor of AUTUM® Thermoplastic Polyimide Resin, Feb. 24, 2003; http://www2.dupont.com/Vespel/en_US/news events/article20030224.html.
Sadiq Muhammad et al: "High-performance planar ultrasonic tool based on d31-mode piezocrystal", IEEE Transactions on Ultrasonics, Ferroelectrics and Frequency Control, IEEE, US, vol. 62, No. 3, Mar. 30, 2015 (Mar. 30, 2015), pp. 428-438, XP011574640, ISSN: 0885-3010, DOI: 10.1109/TUFFC.2014.006437.
Leonard I. Malis, M.D., "The Value of Irrigation During Bipolar Coagulation," 1989.
http:/www.ethicon.com/na/epc/code/gen11?lang=en-default.
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Incropera et al., Fundamentals of Heat and Mass Transfer, Wiley, New York (1990). (Book—not attached).
F. A. Duck, "Optical Properties of Tissue Including Ultraviolet and Infrared Radiation," pp. 43-71 in Physical Properties of Tissue (1990).
Campbell et al, "Thermal Imaging in Surgery," p. 19-3, in Medical Infrared Imaging, N. A. Diakides and J. D. Bronzino, Eds. (2008).
http://www.dotmed.com/listing/electrosurical-unit/ethicon/ultracision-g110-/1466724.
http://www.jnj.com/media-center/press-releases/ethical-endo-surgery-highlights-commitment-to . . .

(56)　　　　　References Cited

OTHER PUBLICATIONS

Gerhard, Glen C., "Surgical Electrotechnology: Quo Vadis?," IEEE Transactions on Biomedical Engineering, vol. BME-31, No. 12, pp. 787-792, Dec. 1984.

Fowler, K.R., "A Programmable, Arbitrary Waveform Electrosurgical Device," IEEE Engineering in Medicine and Biology Society 10th Annual International Conference, pp. 1324, 1325 (1988).

Sullivan, "Cost-Constrained Selection of Strand Diameter and Number in a Litz-Wire Transformer Winding," IEEE Transactions on Power Electronics, vol. 16, No. 2, Mar. 2001, pp. 281-288.

Graff, K.F., "Elastic Wave Propagation in a Curved Sonic Transmission Line," IEEE Transactions on Sonics and Ultrasonics, SU-17(1), 1-6 (1970).

Makarov, S. N., Ochmann, M., Desinger, K., "The longitudinal vibration response of a curved fiber used for laser ultrasound surgical therapy," Journal of the Acoustical Society of America 102, 1191-1199 (1997).

Morley, L. S. D., "Elastic Waves in a Naturally Curved Rod," Quarterly Journal of Mechanics and Applied Mathematics, 14: 155-172 (1961).

Walsh, S. J., White, R. G., "Vibrational Power Transmission in Curved Beams," Journal of Sound and Vibration, 233(3), 455-488 (2000).

Covidien Brochure, [Value Analysis Brief], LigaSure Advance™ Pistol Grip, dated Rev. Apr. 2010 (7 pages).

Wright, et al., "Time-Temperature Equivalence of Heat-Induced Changes in Cells and Proteins," Feb. 1998. ASME Journal of Biomechanical Engineering, vol. 120, pp. 22-26.

Covidien Brochure, LigaSure Impact™ Instrument LF4318, dated Feb. 2013 (3 pages).

Covidien Brochure, LigaSure Atlas™ Hand Switching Instruments, dated Dec. 2008 (2 pages).

Covidien Brochure, The LigaSure™ 5 mm Blunt Tip Sealer/Divider Family, dated Apr. 2013 (2 pages).

Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.

Jang, J. et al. "Neuro-fuzzy and Soft Computing." Prentice Hall, 1997, pp. 13-89, 199-293, 335-393, 453-496, 535-549.

Sullivan, "Optimal Choice for Number of Strands in a Litz-Wire Transformer Winding," IEEE Transactions on Power Electronics, vol. 14, No. 2, Mar. 1999, pp. 283-291.

Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).

Henriques. F.C., "Studies in thermal injury V. The predictability and the significance of thermally induced rate processes leading to irreversible epidermal injury." Archives of Pathology, 434, pp. 489-502 (1947).

Wall et al., "Thermal modification of collagen," J Shoulder Elbow Surg, No. 8, pp. 339-344 (Jul./Aug. 1999).

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Harris et al., "Kinetics of Thermal Damage to a Collagenous Membrane Under Blaxial Isotonic Loading," IEEE Transactions on Biomedical Engineering, vol. 51, No. 2, pp. 371-379 (Feb. 2004).

Harris et al., "Altered Mechanical Behavior of Epicardium Due to Isothermal Heating Under Blaxial isotonic Loads," Journal of Biomechanical Engineering, vol. 125, pp. 381-388 (Jun. 2003).

Lee et al., "A multi-sample denaturation temperature tester for collagenous biomaterials," Med. Eng. Phy., vol. 17, No. 2, pp. 115-121 (Mar. 1995).

Moran et al., "Thermally Induced Shrinkage of Joint Capsule," Clinical Orthopaedics and Related Research, No. 281, pp. 248-255 (Dec. 2000).

Wells et al., "Altered Mechanical Behavior of Epicardium Under Isothermal Biaxial Loading," Transactions of the ASME, Journal of Biomedical Engineering, vol. 126, pp. 492-497 (Aug. 2004).

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Humphrey, J.D., "Continuum Thermomechanics and the Clinical Treatment of Disease and Injury," Appl. Mech. Rev., vol. 56, No. 2 pp. 231-260 (Mar. 2003).

National Semiconductors Temperature Sensor Handbook—http://www.national.com/appinfo/tempsensors/files/temphb.pdf; accessed online: Apr. 1, 2011.

Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . ., accessed Aug. 25, 2009.

Douglas, S.C. "Introduction to Adaptive Filter". Digital Signal Processing Handbook. Ed. Vijay K. Madisetti and Douglas B. Williams. Boca Raton: CRC Press LLC, 1999.

Chen et al., "Heat-induced changes in the mechanics of a collagenous tissue: pseudoelastic behavior at 37° C.," Journal of Biomechanics, 31, pp. 211-216 (1998).

Kurt Gieck & Reiner Gleck, Engineering Formulas § Z.7 (7th ed. 1997).

Glaser and Subak-Sharpe, Integrated Circuit Engineering, Addison-Wesley Publishing, Reading, MA (1979). (book—not attached).

Covidien 501(k) Summary Sonicision, dated Feb. 24, 2011 (7 pages).

http://www.megadyne.com/es_generator.php.

LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.

https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.

http://www.apicalinstr.com/generators.htm.

http://www.medicalexpo.com/medical-manufacturer/electrosurgical-generator-6951.html.

http://www.valleylab.com/product/es/generators/index.html.

Emam, Tarek A. et al., "How Safe is High-Power Ultrasonic Dissection?," Annals of Surgery, (2003), pp. 186-191, vol. 237, No. 2, Lippincott Williams & Wilkins, Inc., Philadelphia, PA.

Feil, Wolfgang, M.D., et al., "Ultrasonic Energy for Cutting, Coagulating, and Dissecting," (2005), pp. IV, 17, 21, and 23; ISBN 3-13-127521-9 (New York, NY, Thieme, New York).

McCarus, Steven D. M.D., "Physiologic Mechanism of the Ultrasonically Activated Scalpel," The Journal of the American Association of Gynecologic Laparoscopists; (Aug. 1996), vol. 3, No. 4., pp. 601-606 and 608.

U.S. Appl. No. 29/404,676, filed Oct. 24, 2011.

U.S. Appl. No. 13/151,181, filed Jun. 2, 2011.

U.S. Appl. No. 13/369,561, filed Feb. 9, 2012.

U.S. Appl. No. 13/369,569, filed Feb. 9, 2012.

U.S. Appl. No. 13/369,578, filed Feb. 9, 2012.

U.S. Appl. No. 13/369,584, filed Feb. 9, 2012.

U.S. Appl. No. 13/369,588, filed Feb. 9, 2012.

U.S. Appl. No. 13/369,594, filed Feb. 9, 2012.

U.S. Appl. No. 13/369,601, filed Feb. 9, 2012.

U.S. Appl. No. 13/369,609, filed Feb. 9, 2012.

U.S. Appl. No. 13/369,629, filed Feb. 9, 2012.

U.S. Appl. No. 13/369,666, filed Feb. 9, 2012.

(56)        References Cited

OTHER PUBLICATIONS

U.S. Appl. No. 13/545,292, filed Jul. 10, 2012.
U.S. Appl. No. 13/584,020, filed Aug. 13, 2012.
U.S. Appl. No. 13/584,445, filed Aug. 13, 2012.
U.S. Appl. No. 13/584,878, filed Aug. 14, 2012.
U.S. Appl. No. 13/585,124, filed Aug. 14, 2012.
U.S. Appl. No. 13/585,292, filed Aug. 14, 2012.
European Search Report for 11175923.9, dated Oct. 7, 2013 (5 pages).
European Search Report for 11175923.9, dated Nov. 30, 2012 (6 pages).
International Preliminary Report on Patentability for PCT/US2008/071706, dated Feb. 2, 2010 (12 pages).
Partial International Search Report for PCT/US2008/071706, Feb. 25, 2009 (2 pages).
International Search Report for PCT/US2008/071706, May 19, 2009 (9 pages).
U.S. Appl. No. 12/469,293, filed May 20, 2009.
U.S. Appl. No. 12/469,308, filed May 20, 2009.
U.S. Appl. No. 12/503,775, filed Jul. 15, 2009.
U.S. Appl. No. 12/503,769, filed Jul. 15, 2009.
U.S. Appl. No. 12/503,770, filed Jul. 15, 2009.
U.S. Appl. No. 12/503,766, filed Jul. 15, 2009.
U.S. Appl. No. 12/490,906, filed Jun. 24, 2009.
U.S. Appl. No. 12/490,922, filed Jun. 24, 2009.
U.S. Appl. No. 12/490,933, filed Jun. 24, 2009.
U.S. Appl. No. 12/490,948, filed Jun. 24, 2009.
U.S. Appl. No. 11/998,758, filed Nov. 30, 2007.
U.S. Appl. No. 12/245,158, filed Oct. 3, 2008.
U.S. Appl. No. 29/292,295, filed Oct. 5, 2007.
U.S. Appl. No. 11/998,543, filed Nov. 30, 2007.
U.S. Appl. No. 29/327,737, filed Nov. 12, 2008.
U.S. Appl. No. 12/274,884, filed Nov. 20, 2008.
U.S. Appl. No. 12/703,860, filed Feb. 11, 2010.
U.S. Appl. No. 12/703,864, filed Feb. 11, 2010.
U.S. Appl. No. 12/703,866, filed Feb. 11, 2010.
U.S. Appl. No. 12/703,870, filed Feb. 11, 2010.
U.S. Appl. No. 12/703,875, filed Feb. 11, 2010.
U.S. Appl. No. 12/703,877, filed Feb. 11, 2010.
U.S. Appl. No. 12/703,879, filed Feb. 11, 2010.
U.S. Appl. No. 12/703,885, filed Feb. 11, 2010.
U.S. Appl. No. 12/703,893, filed Feb. 11, 2010.
U.S. Appl. No. 12/703,899, filed Feb. 11, 2010.
U.S. Appl. No. 29/361,917, filed May 17, 2010.
U.S. Appl. No. 12/896,351, filed Oct. 1, 2010.
U.S. Appl. No. 12/896,479, filed Oct. 1, 2010.
U.S. Appl. No. 12/896,360, filed Oct. 1, 2010.
U.S. Appl. No. 12/896,345, filed Oct. 1, 2010.
U.S. Appl. No. 12/896,384, filed Oct. 1, 2010.
U.S. Appl. No. 12/896,467, filed Oct. 1, 2010.
U.S. Appl. No. 12/896,451, filed Oct. 1, 2010.
U.S. Appl. No. 12/896,470, filed Oct. 1, 2010.
U.S. Appl. No. 12/896,411, filed Oct. 1, 2010.
U.S. Appl. No. 12/896,420, filed Oct. 1, 2010.

SURGICAL INSTRUMENTS

This application is a continuation application claiming priority under 35 U.S.C. § 120 to U.S. patent application Ser. No. 16/539,122, now U.S. Pat. No. 11,666,784, filed Aug. 13, 2019, which is a continuation application of U.S. patent application Ser. No. 15/257,385, now U.S. Pat. No. 10,420, 579, filed Sep. 6, 2016, which is a continuation application of U.S. patent application Ser. No. 13/923,954, now U.S. Pat. No. 9,445,832, filed Jun. 21, 2013, which is a continuation application U.S. patent application Ser. No. 11/888, 222, now U.S. Pat. No. 8,512,365, which issued on Aug. 20, 2013; the entire disclosures of each of which are hereby incorporated by reference herein.

BACKGROUND

Ultrasonic instruments, including both hollow core and solid core instruments, are used for the safe and effective treatment of many medical conditions. Ultrasonic instruments are advantageous because they may be used to cut and/or coagulate organic tissue using energy in the form of mechanical vibrations transmitted to a surgical end effector at ultrasonic frequencies. Ultrasonic vibrations, when transmitted to organic tissue at suitable energy levels and using a suitable end effector, may be used to cut, dissect, elevate or cauterize tissue or to separate muscle tissue off bone. Such instruments may be used for open procedures or minimally invasive procedures, such as endoscopic or laparoscopic procedures, wherein the end effector is passed through a trocar to reach the surgical site.

Activating or exciting the end effector (e.g., cutting blade) of such instruments at ultrasonic frequencies induces longitudinal vibratory movement that generates localized heat within adjacent tissue, facilitating both cutting and coagulation. Because of the nature of ultrasonic instruments, a particular ultrasonically actuated end effector may be designed to perform numerous functions, including, for example, cutting and coagulation.

Ultrasonic vibration is induced in the surgical end effector by electrically exciting a transducer, for example. The transducer may be constructed of one or more piezoelectric or magnetostrictive elements in the instrument hand piece. Vibrations generated by the transducer section are transmitted to the surgical end effector via an ultrasonic waveguide extending from the transducer section to the surgical end effector. The waveguides and end effectors are designed to resonate at the same frequency as the transducer. Therefore, when an end effector is attached to a transducer the overall system frequency is the same frequency as the transducer itself.

The zero to peak amplitude of the longitudinal ultrasonic vibration at the tip, d, of the end effector behaves as a simple sinusoid at the resonant frequency as given by:

$$d = A \sin(\omega t)$$

where:

$\omega$=the radian frequency which equals 2n times the cyclic frequency, f; and A=the zero-to-peak amplitude.

The longitudinal excursion is defined as the peak-to-peak (p-t-p) amplitude, which is just twice the amplitude of the sine wave or 2A.

Ultrasonic surgical instruments may be divided into two types, single element end effector devices and multiple-element end effector devices. Single element end effector devices include instruments such as scalpels and ball coagulators. Single-element end effector instruments have limited ability to apply blade-to-tissue pressure when the tissue is soft and loosely supported. Sometimes, substantial pressure may be necessary to effectively couple ultrasonic energy to the tissue. This inability to grasp the tissue results in a further inability to fully coapt tissue surfaces while applying ultrasonic energy, leading to less-than-desired hemostasis and tissue joining. In these cases, multiple-element end effectors may be used. Multiple-element end effector devices, such as clamping coagulators, include a mechanism to press tissue against an ultrasonic blade that can overcome these deficiencies.

Although ultrasonic surgical instruments are widely used in many surgical applications, their utility is limited by their inability to react to tissue and end effector conditions. For example, as the end effector of an ultrasonic instrument is used to coagulate and/or cut tissue, it often heats up. This may cause inconsistencies in the performance of the instrument. Also, there is no way for a clinician using the instrument to know when the instrument has begun to coagulate tissue, when the instrument has begun to cut tissue, or any other information about the tissue.

Another set of drawbacks of ultrasonic instruments stems from existing end effector designs. In the existing designs, only the tip of the end effector (e.g., the blade) is ultrasonically active. Accordingly, tissue contacting the blade more than a fraction of a wavelength from the tip may not be affected at all. Further, because waves must propogate from the transducer to the tip of the end effector, existing end effectors are not very flexible, limiting their ability to articulate and consequently limiting their usefulness in laparoscopic and endoscopic surgical applications.

SUMMARY

In one general aspect, the various embodiments are directed to a surgical device. The surgical device may comprise a transducer, an end effector, a generator and a control circuit. The transducer may be configured to provide vibrations. The end effector may be coupled to the transducer and may extend from the transducer along the longitudinal axis. The generator may provide an electrical signal to the transducer. Also, the control circuit may modify a current amplitude of the electrical signal in response to a change in a vibration frequency of the end effector. Accordingly to various embodiments, the control circuit may detect a first contribution to a vibration frequency of the end effector, the first contribution originating from tissue in contact with the end effector. Also, according to various embodiments, the control circuit may indicate a change in a vibration frequency of the end effector.

In another general aspect, the various embodiments are directed to a surgical instrument comprising a transducer, a clamping mechanism and a control circuit. The transducer may be configured to provide vibrations. The end effector may be coupled to the transducer and may extend from the transducer along the longitudinal axis. The clamping mechanism may be translatable toward the end effector. The control circuit may calculate a curve representing a coefficient of collagen denaturation over time. The coefficient of collagen denaturation may be calculated considering: a power delivered by the end effector to a portion of tissue; a clamp force applied to the portion of tissue between the end effector and the clamping mechanism; a displacement of the end effector; and a vibration frequency of the end effector. According to various embodiments, the control circuit also may identify a first change in a slope of the curve from a substantially negative slope to a substantially neutral slope and indicate a beginning of tissue coagulation in response to the first change. Also, according to various embodiments, the control circuit may identify a first region of the curve having a substantially constant slope. The control circuit also may calculate a region property describing the first region and derive a tissue property of the portion of tissue in contact with the end effector.

In yet another general aspect, the various embodiments are directed to a surgical device comprising an end effector. The end effector may comprise a central member extending longitudinally through the end effector and a plurality of radial mode transducers. The radial mode transducers may be positioned around the central member, and may be configured to respond to an electrical signal by vibrating in a direction perpendicular to the longitudinal axis. The standing waves may be ultrasonic.

FIGURES

The novel features of the various embodiments are set forth with particularity in the appended claims. The various embodiments, however, both as to organization and methods of operation, together with further objects and advantages thereof, may best be understood by reference to the following description, taken in conjunction with the accompanying drawings as follows.

DESCRIPTION

Figures 1, 4:
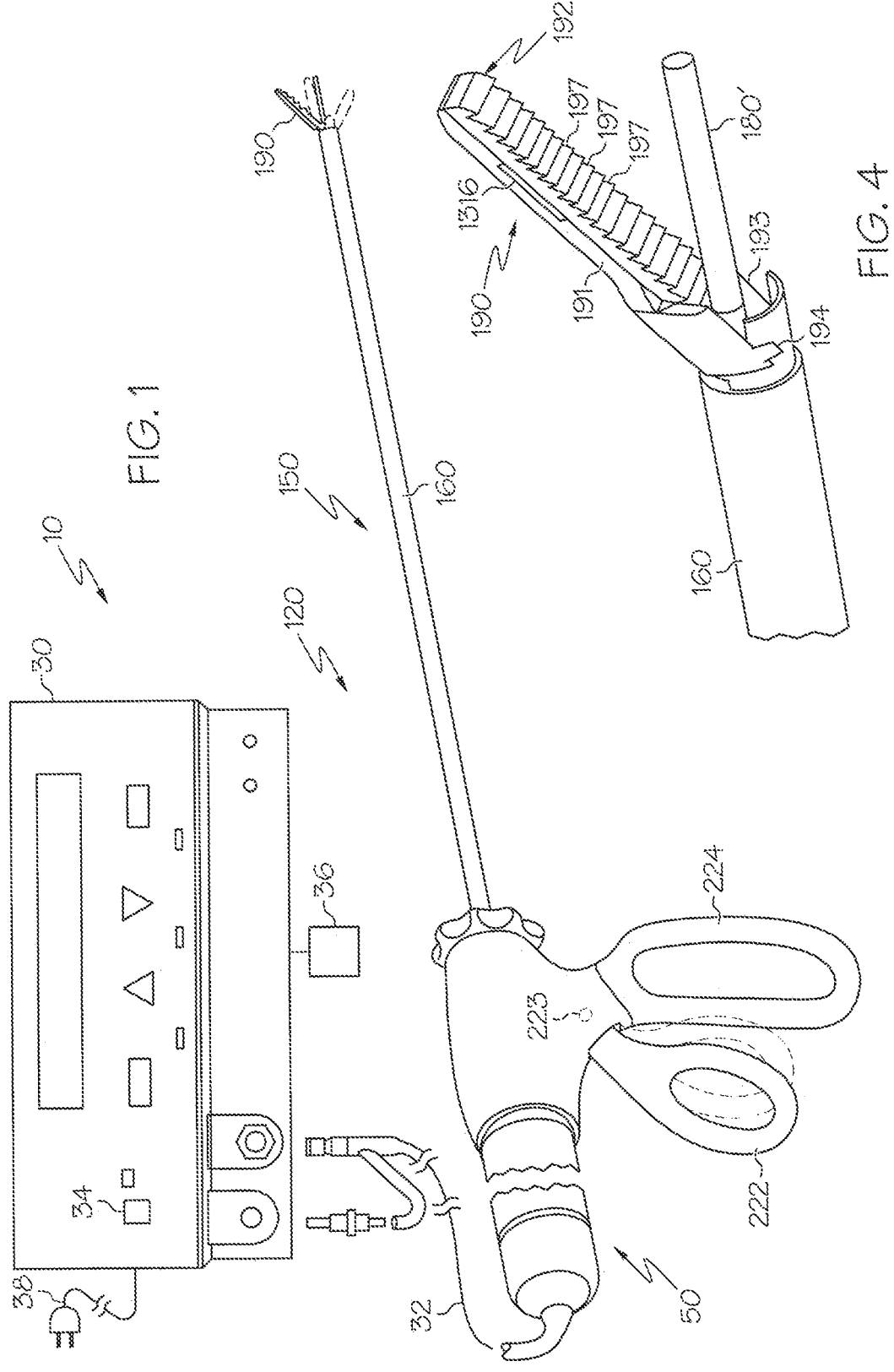
FIG. 1 illustrates one embodiment of a surgical system including a surgical instrument and an ultrasonic generator.
FIG. 4 illustrates one embodiment of a clamping mechanism that may be used with the surgical instrument shown in FIG. 1.

Before explaining the various embodiments in detail, it should be noted that the embodiments are not limited in application or use to the details of construction and arrangement of parts illustrated in the accompanying drawings and description. The illustrative embodiments may be implemented or incorporated in other embodiments, variations and modifications, and may be practiced or carried out in various ways. For example, the surgical instruments and blade configurations disclosed below are illustrative only and not meant to limit the scope or application thereof. Also, the blade and end effector designs described hereinbelow may be used in conjunction with any suitable device. Furthermore, unless otherwise indicated, the terms and expressions employed herein have been chosen for the purpose of describing the illustrative embodiments for the convenience of the reader and are not to limit the scope thereof.

Examples of ultrasonic surgical instruments and blades are disclosed in U.S. Pat. Nos. 5,322,055 and 5,954,736, 6,309,400 B2, 6,278,218 B1, 6,283,981 B1, and 6,325,811 B1, which are incorporated herein by reference in their entirety. These references disclose ultrasonic surgical instrument designs and blade designs where a longitudinal mode of the blade is excited. The result is a longitudinal standing wave within the instrument. Accordingly, the instrument has nodes, where the transverse motion is equal to zero, and anti-nodes, where the transverse motion is at its maximum. The instrument's tissue end effector is often positioned at an anti-node to maximize its longitudinal motion.

Various embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting embodiments and that the scope of the various embodiments is defined solely by the claims. The features illustrated or described in connection with one embodiment may be combined with the features of other embodiments. Such modifications and variations are intended to be included within the scope of the claims.

It will be appreciated that the terms "proximal" and "distal" are used herein with reference to a clinician gripping a surgical device at its hand piece assembly, or other comparable piece. Thus, the end effector is distal with respect to the more proximal hand piece assembly. It will be further appreciated that, for convenience and clarity, spatial terms such as "top" and "bottom" also are used herein with respect to the clinician gripping the hand piece assembly, or comparable piece. However, surgical instruments are used in many orientations and positions, and these terms are not intended to be limiting and absolute.

FIG. 1 illustrates one embodiment of a surgical system including a surgical instrument and an ultrasonic generator.

Figure 2:
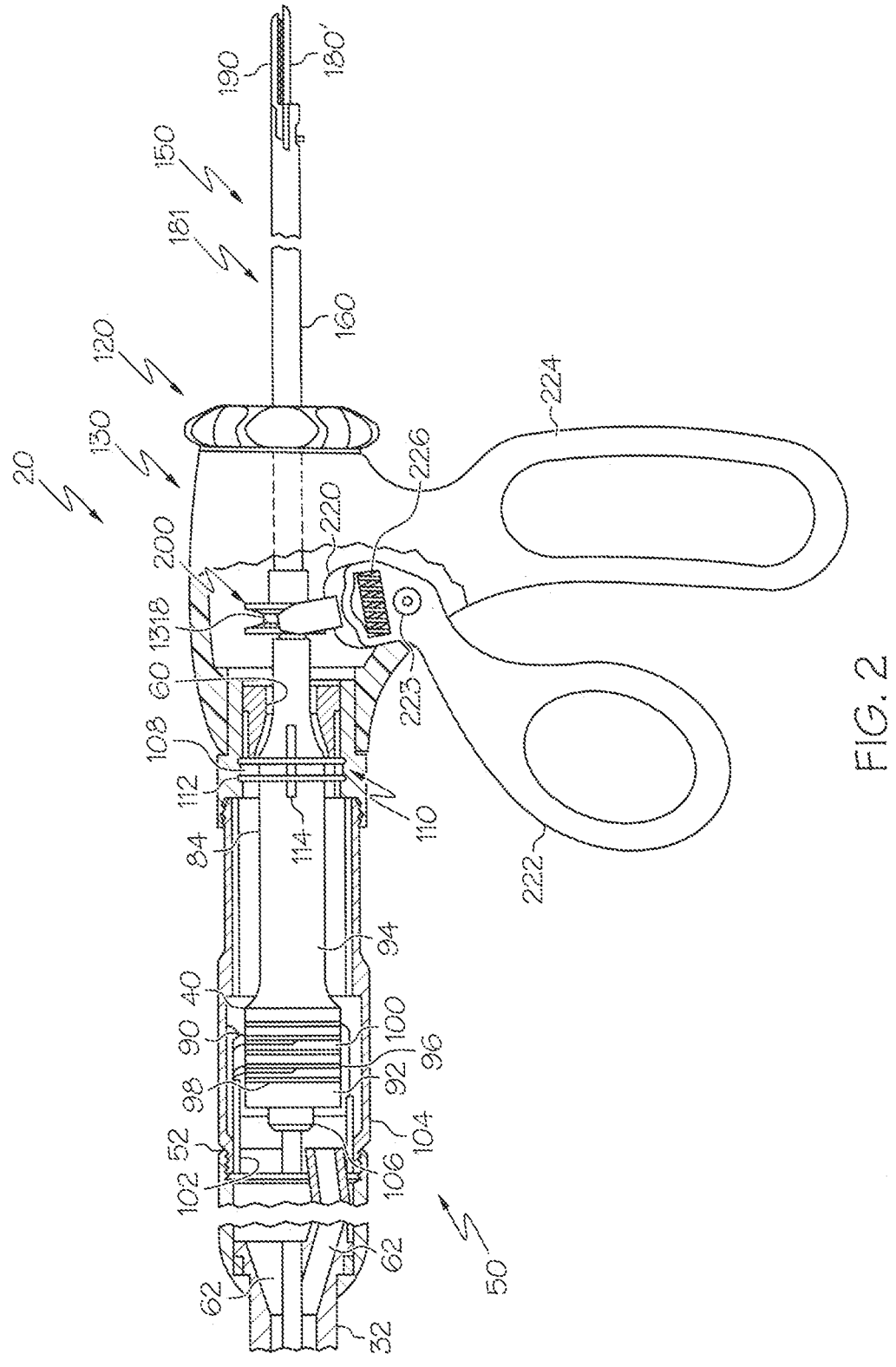
FIG. 2 illustrates one embodiment of the surgical instrument shown in FIG. 1.

FIG. 2 illustrates one embodiment of the apparatus shown in FIG. 1. In the embodiment illustrated in FIGS. 1-2, the surgical system 10 includes an ultrasonic clamp coagulator instrument 120 and an ultrasonic generator 30. The surgical instrument 120 includes an ultrasonic drive unit 50. As will be further described, an ultrasonic transducer of the drive unit 50, and an ultrasonic end effector 180 of the clamp instrument 120, together provide an acoustic assembly of the surgical system 10, with the acoustic assembly providing ultrasonic energy for surgical procedures when powered by generator 30. It will be noted that, in some applications, the ultrasonic drive unit 50 is referred to as a "hand piece assembly" because the surgical instrument 120 of the surgical system 10 is configured such that a clinician grasps and manipulates the ultrasonic drive unit 50 during various procedures and operations. The instrument 120 may include a scissors-like grip arrangement which facilitates positioning and manipulation of the instrument 120 apart from manipulation of the ultrasonic drive unit 50.

The generator 30 of the surgical system 10 sends an electrical signal through a cable 32 at a selected excursion, frequency, and phase determined by a control system of the generator 30. As will be further described, the signal causes one or more piezoelectric elements of the acoustic assembly of the surgical instrument 120 to expand and contract along a longitudinal axis, thereby converting the electrical energy into mechanical motion. The mechanical motion results in longitudinal waves of ultrasonic energy that propagate through the acoustic assembly in an acoustic standing wave to vibrate the acoustic assembly at a selected frequency and excursion. The end effector 180 is placed in contact with tissue of the patient to transfer the ultrasonic energy to the tissue. For example, a distal portion of blade 180' of the end effector may be placed in contact with the tissue. As further described below, a surgical tool, such as, a jaw or clamping mechanism, may be utilized to press the tissue against the blade 180'.

As the end effector 180 couples with the tissue, thermal energy or heat is generated as a result of friction, acoustic absorption, and viscous losses within the tissue. The heat is sufficient to break protein hydrogen bonds, causing the highly structured protein (e.g., collagen and muscle protein) to denature (e.g., become less organized). As the proteins are denatured, a sticky coagulum forms to seal or coagulate small blood vessels. Deep coagulation of larger blood vessels results when the effect is prolonged.

The transfer of the ultrasonic energy to the tissue causes other effects including mechanical tearing, cutting, cavitation, cell disruption, and emulsification. The amount of cutting as well as the degree of coagulation obtained varies with the excursion of the end effector 180, the frequency of vibration, the amount of pressure applied by the user, the sharpness of the end effector 180, and the coupling between the end effector 180 and the tissue.

In the embodiment illustrated in FIG. 1, the generator 30 includes a control system integral with the generator 30, a power switch 34, and a triggering mechanism 36. The power switch 34 controls the electrical power to the generator 30, and when activated by the triggering mechanism 36, the generator 30 provides energy to drive the acoustic assembly of the surgical system 10 frequency and to drive the end effector 180 at a predetermined excursion level. The generator 30 drives or excites the acoustic assembly at any suitable resonant frequency of the acoustic assembly.

When the generator 30 is activated via the triggering mechanism 36, electrical energy is continuously applied by the generator 30 to a transducer stack or assembly 40 of the acoustic assembly. A phase-locked loop in the control system of the generator 30 monitors feedback from the acoustic assembly. The phase lock loop adjusts the frequency of the electrical energy sent by the generator 30 to match the resonant frequency of the selected longitudinal mode of vibration of the acoustic assembly. In addition, a second feedback loop in the control system maintains the electrical current supplied to the acoustic assembly at a pre-selected constant level in order to achieve substantially constant excursion at the end effector 180 of the acoustic assembly.

The electrical signal supplied to the acoustic assembly will cause the distal end of the end effector 180, e.g., the blade 180', to vibrate longitudinally in the range of, for example, approximately 20 kHz to 250 kHz. According to various embodiments, the blade 180' may vibrate in the range of about 54 kHz to 56 kHz, for example, at about 55.5 kHz. In other embodiments, the blade 180' may vibrate at other frequencies including, for example, about 31 kHz or about 80 kHz. The excursion of the vibrations at the blade can be controlled by, for example, controlling the amplitude of the electrical signal applied to the transducer assembly 40 of the acoustic assembly by the generator 30.

As noted above, the triggering mechanism 36 of the generator 30 allows a user to activate the generator 30 so that electrical energy may be continuously supplied to the acoustic assembly. The triggering mechanism 36 may comprise a foot activating switch that is detachably coupled or attached to the generator 30 by a cable or cord. Alternatively, the triggering mechanism can be configured as a hand switch incorporated in the ultrasonic drive unit 50 to allow the generator 30 to be activated by a user.

The generator 30 also has a power line 38 for insertion in an electro-surgical unit or conventional electrical outlet. It is contemplated that the generator 30 can also be powered by a direct current (DC) source, such as a battery. The generator 30 can comprise any suitable generator, such as Model No. GEN04, available from Ethicon Endo Surgery, Inc.

Figure 3:
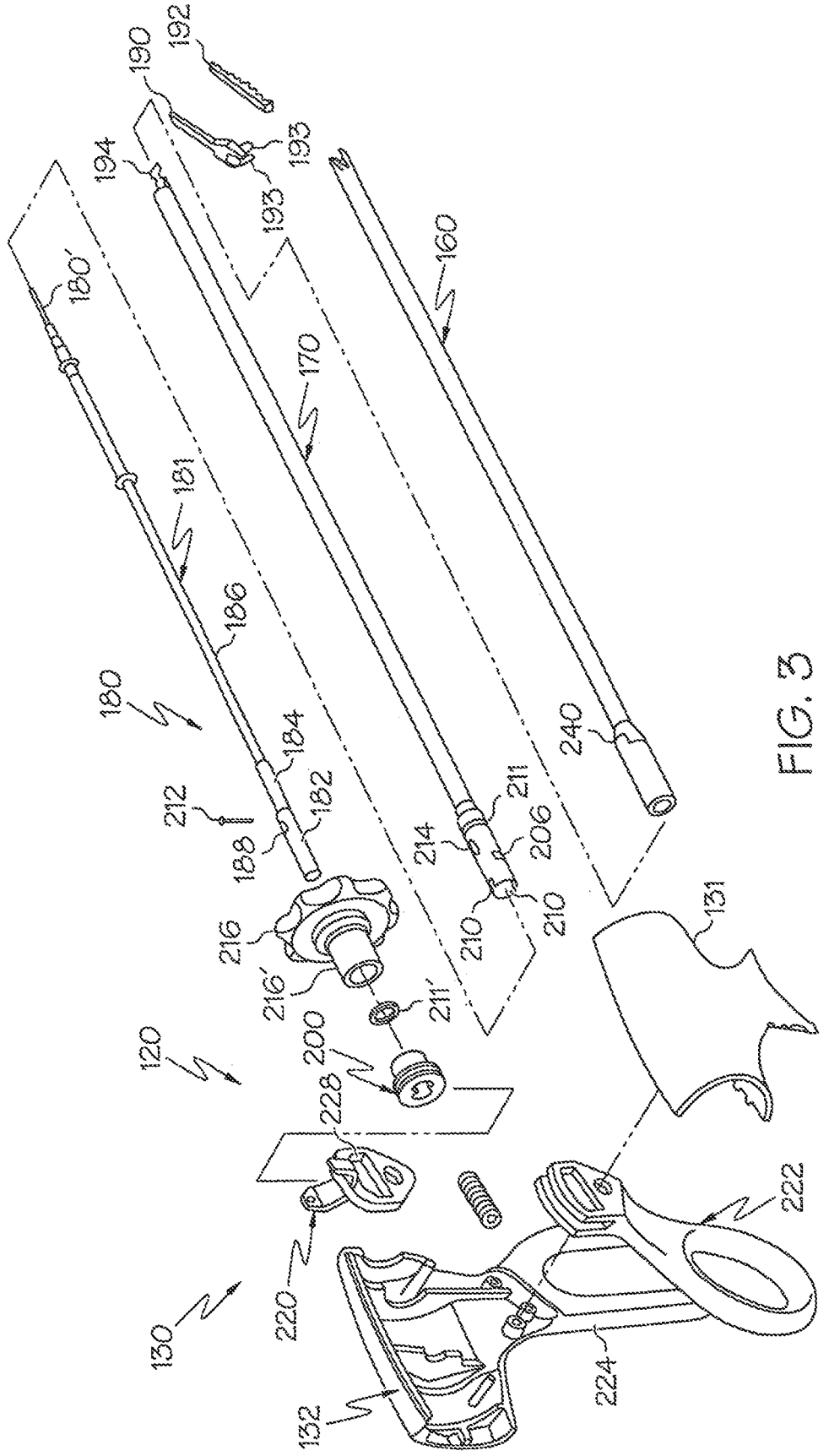
FIG. 3 illustrates an exploded view of one embodiment the surgical instrument shown in FIG. 1.

In the embodiment illustrated in FIGS. 1 and 3, the ultrasonic drive unit 50 of the surgical instrument includes a multi-piece housing 52 adapted to isolate the operator from the vibrations of the acoustic assembly. The drive unit housing 52 can be shaped to be held by a user in a conventional manner, but it is contemplated that the present clamp coagulator instrument 120 principally be grasped and manipulated by a scissors-like arrangement provided by a housing of the apparatus, as will be described. While the multi-piece housing 52 is illustrated, the housing 52 may comprise a single or unitary component.

The housing 52 of the ultrasonic drive unit 50 generally includes a proximal end, a distal end, and a cavity extending longitudinally therein. The distal end of the housing 52 includes an opening 60 configured to allow the acoustic assembly of the surgical system 10 to extend therethrough, and the proximal end of the housing 52 is coupled to the generator 30 by the cable 32. The cable 32 may include ducts or vents 62 to allow air or other fluids to be introduced into the housing 52 of the ultrasonic drive unit 50 to cool the transducer assembly 40 of the acoustic assembly.

The housing 52 of the ultrasonic drive unit 50 may be constructed from a durable plastic, such as ULTEM®. It is also contemplated that the housing 52 may alternatively be made from a variety of materials including other plastics (e.g. liquid crystal polymer (LCP), nylon, or polycarbonate) and/or metals (e.g., aluminum, steel, etc.). A suitable ultrasonic drive unit 50 is Model No. HP054, available from Ethicon Endo Surgery, Inc.

The acoustic assembly of the surgical instrument generally includes a first acoustic portion and a second acoustic portion. The first acoustic portion may be carried by the ultrasonic drive unit 50, and the second acoustic portion (in the form of an end effector 180, as will be described) is carried by the ultrasonic clamp coagulator 120. The distal end of the first acoustic portion is operatively coupled to the proximal end of the second acoustic portion, preferably by a threaded connection.

In the embodiment illustrated in FIG. 2, the first acoustic portion includes the transducer stack or assembly 40 and a mounting device 84, and the second acoustic portion includes the end effector 180. The end effector 180 may in turn comprise a transmission component, or waveguide 181 (FIG. 3), as well as a distal portion, or blade 180', for interfacing with tissue.

The components of the acoustic assembly may be acoustically tuned such that the length of each component is an integral number of one-half wavelengths ($n\lambda/2$), where the wavelength $\lambda$ is the wavelength of a pre-selected or operating longitudinal vibration frequency $f_0$ of the acoustic assembly, and n is any non-negative integer. It is also contemplated that the acoustic assembly may incorporate any suitable arrangement of acoustic elements.

The transducer assembly 40 of the acoustic assembly converts the electrical signal from the generator 30 into mechanical energy that results in longitudinal vibratory motion of the end effector 180 at ultrasonic frequencies. When the acoustic assembly is energized, a vibratory motion standing wave is generated through the acoustic assembly. The excursion of the vibratory motion at any point along the acoustic assembly depends on the location along the acoustic assembly at which the vibratory motion is measured. A minimum or zero crossing in the vibratory motion standing wave is generally referred to as a node (e.g., where motion is usually minimal), and local absolute value maximum or peak in the standing wave is generally referred to as an anti-node. The distance between an anti-node and its nearest node is one-quarter wavelength ($\lambda/4$).

In the embodiment illustrated in FIG. 2, the transducer assembly 40 of the acoustic assembly, which is also known as a "Langevin stack", generally includes a transduction portion 90, a first resonator 92, and a second resonator 94. The transducer assembly 40 may be an integral number of one-half system wavelengths ($n\lambda/2$) in length. It is to be understood that other embodiments of the transducer assembly 40 may comprise a magnetostrictive, electromagnetic or electrostatic transducer.

The distal end of the first resonator 92 is connected to the proximal end of transduction section 90, and the proximal end of the second resonator 94 is connected to the distal end of transduction portion 90. The first and second resonators 92 and 94 may be fabricated from titanium, aluminum, steel, or any other suitable material, and most preferably, the first resonator 92 is fabricated from 303 stainless steel and the second resonator 94 is fabricated from 7075-T651 Aluminum. The first and second resonators 92 and 94 have a length determined by a number of variables, including the length of the transduction section 90, the speed of sound of material used in the resonators 92 and 94, and the desired fundamental frequency $f_0$ of the transducer assembly 40. The second resonator 94 can be tapered inwardly from its proximal end to its distal end to function as a velocity transformer and amplify the ultrasonic vibration excursion.

The transduction portion 90 of the transducer assembly 40 may comprise a piezoelectric section of alternating positive electrodes 96 and negative electrodes 98, with the piezoelectric elements 100 alternating between the electrodes 96 and 98. The piezoelectric elements 100 can be fabricated from any suitable material, such as, for example, lead zirconate-titanate, lead metaniobate, lead titanate, or other piezoelectric material. Each of the positive electrodes 96, negative electrodes 98, and piezoelectric elements 100 have a bore extending through the center. The positive and negative electrodes 96 and 98 are electrically coupled to wires 102 and 104, respectfully. The wires 102 and 104 transmit the electrical signal from the generator 30 to the electrodes 96 and 98.

The piezoelectric elements 100 may be held in compression between the first and second resonators 92 and 94 by a bolt 106. The bolt 106 may have a head, a shank, and a threaded distal end. The bolt 106 may be inserted from the proximal end of the first resonator 92 through the bores of the first resonator 92, the electrodes 96 and 98, and piezoelectric elements 100. The threaded distal end of the bolt 106 is screwed into a threaded bore in the proximal end of second resonator 94. The bolt 106 may be fabricated from steel, titanium, aluminum, or other suitable material. For example, the bolt 106 may be fabricated from Ti-6Al-4V Titanium, or from 4037 low alloy steel.

The piezoelectric elements 100 may be energized in response to the electrical signal supplied from the generator 30 to produce an acoustic standing wave in the acoustic assembly. The electrical signal causes an electromagnetic field across the piezoelectric elements 100, causing the piezoelectric elements 100 to expand and contract in a continuous manner along the longitudinal axis of the voltage gradient, producing high frequency longitudinal waves of ultrasonic energy. The ultrasonic energy is transmitted through the acoustic assembly to the end effector 180.

The mounting device 84 of the acoustic assembly has a proximal end, a distal end, and may have a length substantially equal to an integral number of one-half system wavelengths ($n\lambda/2$). The proximal end of the mounting device 84 may be axially aligned and coupled to the distal end of the second resonator 94 by an internal threaded connection near an anti-node. It is also contemplated that the mounting device 84 may be attached to the second resonator 94 by any suitable means, and the second resonator 94 and mounting device 84 may be formed as a single or unitary component.

The mounting device 84 is coupled to the housing 52 of the ultrasonic drive unit 50 near a node. The mounting device 84 may include an integral mounting flange 108 disposed around its periphery. The mounting flange 108 may be disposed in an annular groove 110 formed in the housing 52 of the ultrasonic drive unit 50 to couple the mounting device 84 to the housing 52. A compliant member or material 112, such as a pair of silicone rubber O-rings attached by stand-offs, may be placed between the annular groove 110 of the housing 52 and the integral flange 108 of the mounting device 86 to reduce or prevent ultrasonic vibration from being transmitted from the mounting device 84 to the housing 52.

The mounting device 84 may be secured in a predetermined axial position by a plurality of pins 114, for example, four. The pins 114 are disposed in a longitudinal direction ninety (90) degrees apart from each other around the outer periphery of the mounting device 84. The pins 114 are coupled to the housing 52 of the ultrasonic drive unit 50 and are disposed through notches in the acoustic mounting flange 108 of the mounting device 84. The pins 114 may be fabricated from stainless steel. According to various embodiments, the pins 114 may be formed as integral components of the housing 52.

The mounting device 84 may be configured to amplify the ultrasonic vibration excursion that is transmitted through the acoustic assembly to the distal end of the end effector 180. In one embodiment, the mounting device 84 comprises a solid, tapered horn. As ultrasonic energy is transmitted through the mounting device 84, the velocity of the acoustic wave transmitted through the mounting device 84 is amplified. It is contemplated that the mounting device 84 be configured as any suitable shape, such as, for example, a stepped horn, a conical horn, an exponential horn, a unitary gain horn, or the like.

The mounting device 84 may be acoustically coupled to the second acoustic portion of the ultrasonic clamp coagulator instrument 120. The distal end of the mounting device 84 may be coupled to the proximal end of the second acoustic portion by an internal threaded connection near an anti-node, but alternative coupling arrangements can be employed.

FIG. 3 illustrates an exploded view of one embodiment of the surgical instrument shown in FIG. 1. The proximal end of the ultrasonic clamp coagulator instrument 120 preferably receives and is fitted to the distal end of the ultrasonic drive unit 50 by insertion of the drive unit 50 into the housing 52, as shown in FIG. 2. The ultrasonic clamp coagulator instrument 120 may be attached to and removed from the ultrasonic drive unit 50 as a unit. The ultrasonic clamp coagulator 120 may be disposed of after a single use.

The ultrasonic clamp coagulator instrument 120 may include a handle assembly or a housing 130, which may comprise mating housing portions 131, 132, and an elongated or endoscopic portion 150. When the present apparatus is configured for endoscopic use, the construction can be dimensioned such that portion 150 has an outside diameter of about 5.5 mm. The elongated portion 150 of the ultrasonic clamp coagulator instrument 120 may extend substantially orthogonally from the apparatus housing 130. The elongated portion 150 can be selectively rotated with respect to the housing 130 as described below. The elongated portion 150 may include an outer tubular member or sheath 160, an inner tubular actuating member 170, and the second acoustic portion of the acoustic system in the form of an end effector 180 including a blade 180'. As will be described, the outer sheath 160, the actuating member 170, and the end effector 180 may be joined together for indexed rotation as a unit (together with ultrasonic drive unit 50) relative to housing 130.

The proximal end of the end effector 180 of the second acoustic portion may be detachably coupled to the mounting device 84 of the ultrasonic drive unit 50 near an anti-node as described above. The end effector 180 may have a length substantially equal to an integer number of one-half system wavelengths ($n\lambda/2$). The end effector 180 may be fabricated from a solid core shaft constructed out of material which propagates ultrasonic energy efficiently, such as a titanium alloy (e.g., Ti-6Al-4V) or an aluminum alloy. It is contemplated that the end effector 180 can alternatively be fabricated from any other suitable material.

As described, the end effector 180 may include a waveguide 181. The waveguide 181 may be substantially semi-flexible. It will be recognized that, the waveguide 181 can alternatively be substantially rigid or may comprise a flexible wire. The waveguide 181 may be configured to amplify the mechanical vibrations transmitted through the waveguide to the blade as is well known in the art. The waveguide 181 may further have features to control the gain of the longitudinal vibration along the waveguide 181 and features to tune the waveguide to the resonant frequency of the system.

It will be recognized that the end effector 180 may have any suitable cross-sectional dimension. For example, the end effector 180 may have a substantially uniform cross-section or the end effector 180 may be tapered at various sections or may be tapered along its entire length.

Referring now to FIG. 3, the waveguide 181 portion of the end effector 180 is shown to comprise a first section 182, a second section 184, and a third section 186. The first section 182 may extend distally from the proximal end of the end effector 180, and has a substantially continuous cross-section dimension. The first section 182 may include at least one radial hole or aperture 188 extending diametrically therethrough, substantially perpendicular to the axis of the end effector 180. The aperture 188 may be positioned at a node, but may be otherwise positioned. It will be recognized that the aperture 188 may have any suitable depth and may be any suitable shape. The aperture 188 is configured to receive a connector pin member which connects the wave guide 181, the tubular actuating member 170, and the tubular outer sheath 160 together for conjoint, indexed rotation relative to apparatus housing 130.

The second section 184 of the wave guide 181 extends distally from the first section 182. The second section 184 preferably also has a substantially continuous cross-section. The diameter of the second section 184 may be smaller than the diameter of the first section 182 and larger than the diameter of the third section 186. As ultrasonic energy passes from the first section 182 of the end effector 180 into the second section 184, narrowing of the second section 184 will result in an increased amplitude of the ultrasonic energy passing therethrough.

The third section 186 extends distally from the distal end of the second section 184. The third section 186 also has a substantially continuous cross-section. The third section 186 also may include small diameter changes along its length. According to various embodiments, the transition from the second section 184 to the third section 186 may be positioned at an anti-node so that the diameter change in the third section does not bring about an increase in the amplitude of vibration.

The third section 186 may have a plurality of grooves or notches (not shown) formed in its outer circumference. The grooves may be located at nodes of the end effector 180 to act as alignment indicators for the installation of a damping sheath (not shown) and stabilizing silicone rings or compliant supports during manufacturing. A seal may be provided at the distal-most node, nearest the blade 180', to abate passage of tissue, blood, and other material in the region between the waveguide and actuating member 170.

The blade 180' of the end effector 180 may be integral therewith and formed as a single unit. The blade 180' may alternately be connected by a threaded connection, or by a welded joint. According to various embodiments, the blade 180' may be mechanically sharp or mechanically blunt. The distal end of the blade 180' is disposed near an anti-node in order to tune the acoustic assembly to a preferred resonant frequency $f_0$ when the acoustic assembly is not loaded by tissue. When the transducer assembly is energized, the distal end of the blade 180' is configured to move longitudinally in the range of, for example, approximately 10-500 microns peak-to-peak, and preferably in the range of about 10 to about 100 microns at a predetermined vibrational frequency $f_0$.

In accordance with the illustrated embodiment, the blade 180' may be cylindrical for cooperation with the associated clamping mechanism of the clamp coagulator 120. The end effector 180 may receive suitable surface treatment, as is known in the art.

FIG. 4 illustrates one embodiment of a clamping mechanism that may be used with the surgical instrument shown in FIG. 1. The clamping mechanism may be configured for cooperative action with the blade 180' of the end effector 180. The clamping mechanism includes a pivotally movable clamp arm 190, which is pivotally connected at the distal end thereof to the distal end of outer tubular sheath 160. The clamp arm 190 includes a clamp arm tissue pad 192, preferably formed from TEFLON® or other suitable low-friction material, which is mounted for cooperation with the blade 180', with pivotal movement of the clamp arm 190 positioning the clamp pad 192 in substantially parallel relationship to, and in contact with, the blade 180'. By this construction, tissue to be clamped is grasped between the tissue pad 192 and the blade 180'. The tissue pad 192 may be provided with a sawtooth-like configuration including a plurality of axially spaced, proximally extending gripping teeth 197 to enhance the gripping of tissue in cooperation with the blade 180'.

Pivotal movement of the clamp arm 190 with respect to the blade 180' is effected by the provision of at least one, and preferably a pair of lever portions 193 of the clamp arm 190 at the proximal end thereof. The lever portions 193 are positioned on respective opposite sides of the end effector 180 and blade 180', and are in operative engagement with a drive portion 194 of the reciprocal actuating member 170. Reciprocal movement of the actuating member 170, relative to the outer tubular sheath 160 and the end effector 180, thereby effects pivotal movement of the clamp arm 190 relative to the blade 180'. The lever portions 193 can be respectively positioned in a pair of openings defined by the drive portion 194, or otherwise suitably mechanically coupled therewith, whereby reciprocal movement of the actuating member 170 acts through the drive portion 194 and lever portions 193 to pivot the clamp arm 190.

Figure 5:
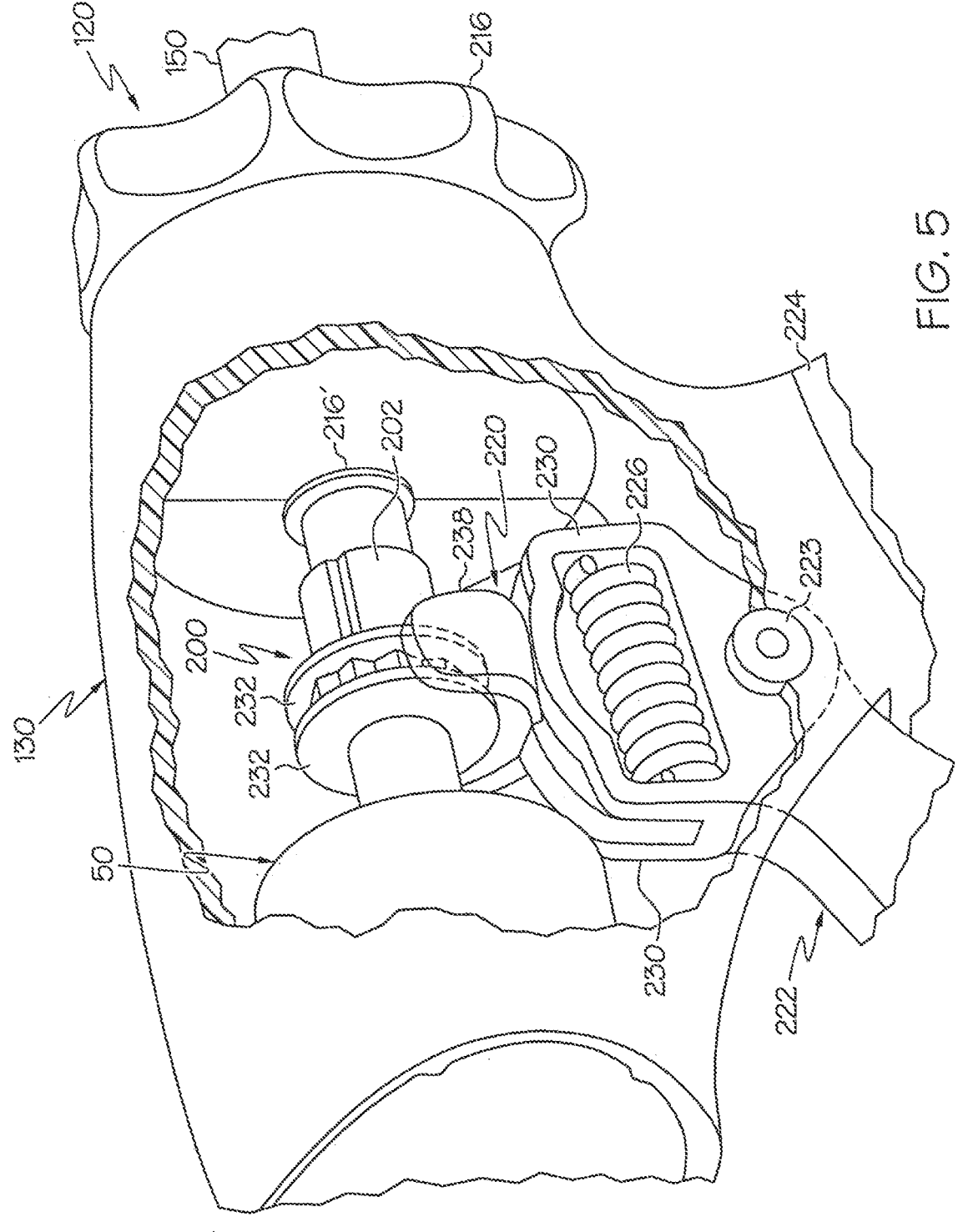
FIG. 5 illustrates a cut-away view of one embodiment of the surgical instrument shown in FIG. 1.
Figure 6:
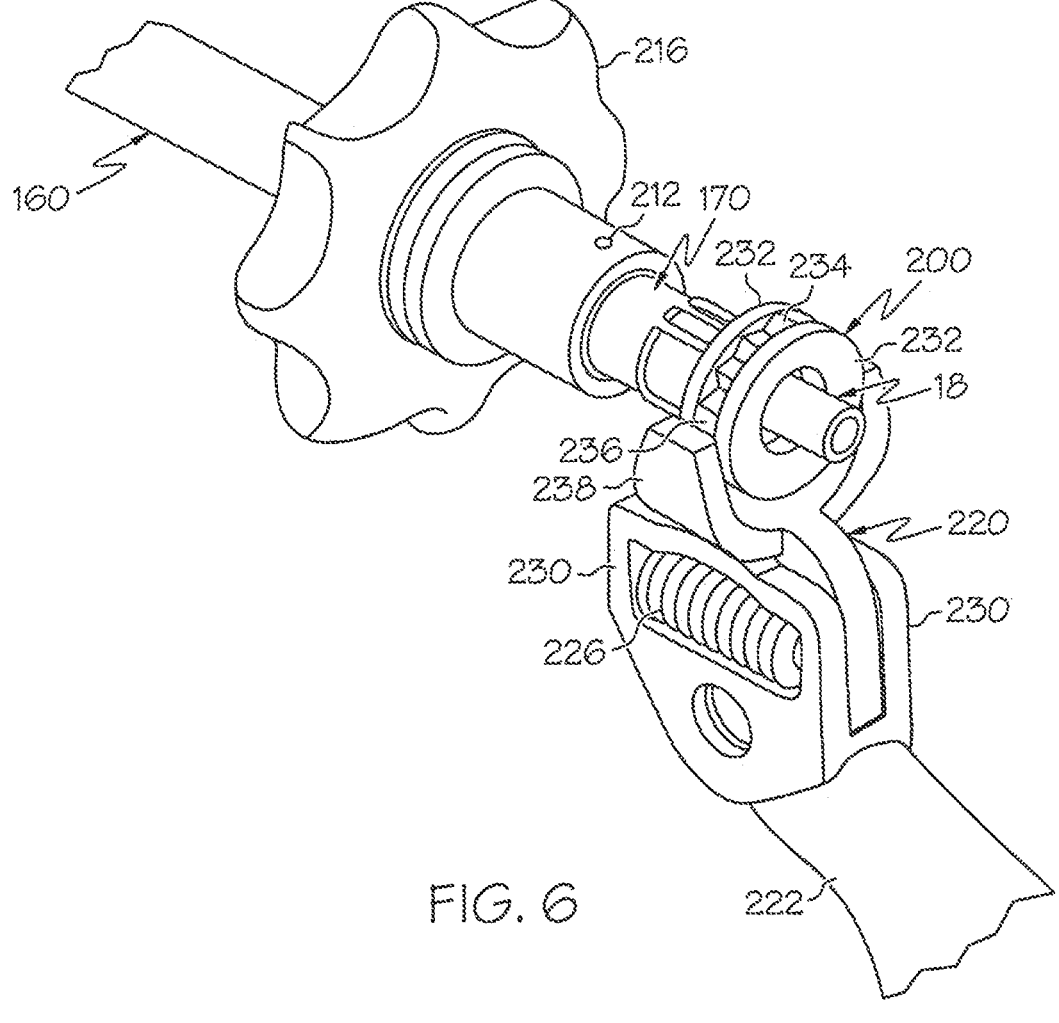
FIG. 6 illustrates various internal components of one embodiment of the surgical instrument shown in FIG. 1.
Figure 7:
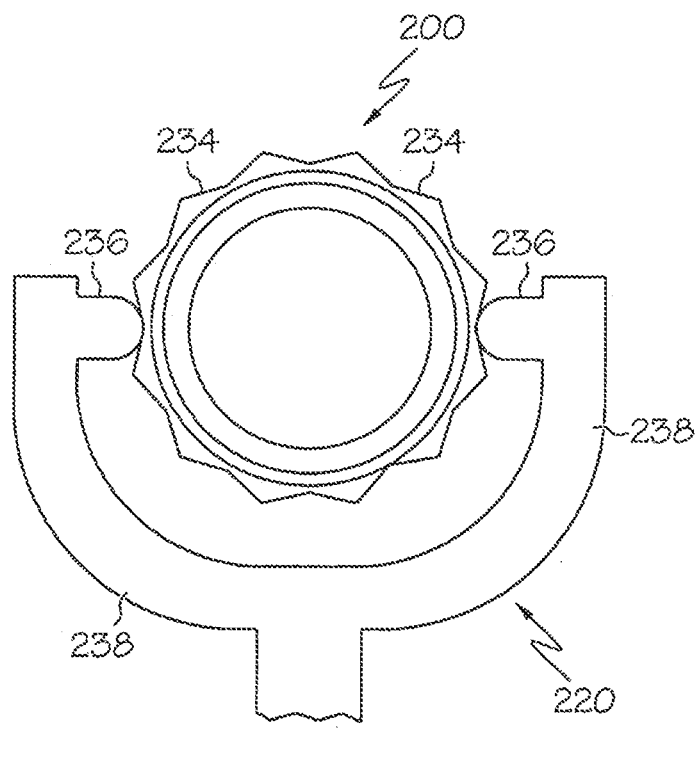
FIG. 7 illustrates one embodiment of a drive yoke of the surgical instrument shown in FIG. 1.
Figure 8:
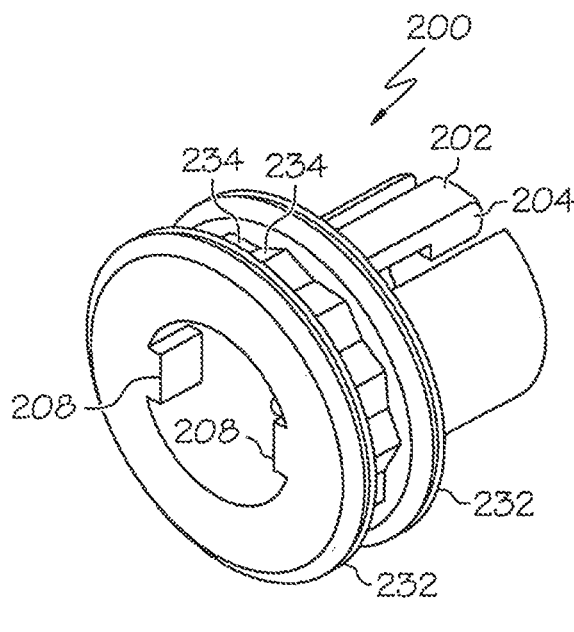
FIG. 8 illustrates one embodiment of a drive collar of the surgical instrument shown in FIG. 1.

FIG. 5 illustrates a cut-away view of one embodiment of the surgical instrument shown in FIG. 1, while FIG. 6 illustrates various internal components of one embodiment of the surgical instrument shown in FIG. 1. FIG. 7 illustrates one embodiment of a drive yoke, and FIG. 8 illustrates one embodiment of a drive collar of the surgical instrument shown in FIG. 1. In the embodiment illustrated in FIGS. 3 and 5-8, reciprocal movement of the actuating member 170 is effected by the provision of a drive collar 200 mounted on the proximal end of the actuating member 170 for conjoint rotation. The drive collar 200 may include a pair of diametrically opposed axially extending arms 202 each having a drive lug 204, with the drive lugs 204 being biased by the arms 202 into engagement with suitable openings 206 defined by the proximal portion of tubular actuating member 170. Rotation of the drive collar 200 together with the actuating member 170 is further effected by the provision of a pair of keys 208 diametrically engageable with suitable openings 210 defined by the proximal end of the actuating member 170. A circumferential groove 211 on the actuating member 170 receives an O-ring 211' (FIG. 3) for engagement with the inside surface of outer sheath 160.

Rotation of the actuating member 170 together with the tubular outer sheath 160 and inner end effector 180 is provided by a connector pin 212 extending through these components of the instrument 120. The tubular actuating member 170 defines an elongated slot 214 through which the connector pin 212 extends to accommodate reciprocal movement of the actuating member relative to the outer tubular sheath and the inner waveguide.

A rotation knob 216 mounted on the outer tubular sheath facilitates rotational positioning of the elongated portion 150 with respect to the housing 130 of the clamp coagulator instrument 120. Connector pin 212 preferably joins the knob 216 together with the sheath 160, member 170, and the end effector 180 for rotation as a unit relative to the housing 130. In the embodiment, hub portion 216' of the rotation knob 216 acts to rotatably mount the outer sheath 160, the actuating member 170, and the end effector 180 (as a unit with the knob 216), on the housing 130.

The drive collar 200 provides a portion of the clamp drive mechanism of the instrument 120, which effects pivotal movement of the clamp arm 190 by reciprocation of the actuating member 170. The clamp drive mechanism further includes a drive yoke 220 which is operatively connected with an operating lever 222, with the operating lever thus interconnected with the reciprocal actuating member 170 via drive yoke 220 and drive collar 200. The operating lever 222 is pivotally connected to the housing 130 of the apparatus (by a pivot mount 223) for cooperation in a scissors-like fashion with a handgrip portion 224 of the housing. Movement of the lever 222 toward the handgrip portion 224 translates the actuating member 170 proximally, thereby pivoting the clamp arm 190 toward the blade 180'.

Operative connection of the drive yoke 220 with the operating lever 222 is provided by a spring 226, preferably comprising a compression coil spring 226. The spring 226 fits within a spring slot 228 defined by the drive yoke 220, which in turn is positioned between a pair of spring retainer flanges 230 of the operating lever 222. The drive yoke 220 is pivotally movable with respect to the spring flanges 230 (about pivot mount 223 of housing 130) in opposition to the compression coil spring, which bears against the surfaces of the spring slots defined by each of the spring flanges 230. In this manner, the force which can be applied to the actuating member 170, by pivotal movement of the operating lever 222 acting through the drive yoke 220 and the drive collar 200, is limited by the force with which the spring 226 bears against the spring flanges 230. Application of excessive force results in pivotal displacement of the drive yoke 220 relative to the spring flanges 230 of the operating lever 222 in opposition to spring 226. Stop portions of the housing 130 limit the travel of the operating lever 222 to prevent excessive compression of spring 226. In various embodiments, the force applied to the actuating member 170 may be limited by one or more springs (not shown) operatively positioned between the drive collar 200 and the member 170. For example, one or more cylindrical springs, such as a wave springs, may be used. An example embodiment utilizing a wave spring in this manner is described in U.S. Pat. No. 6,458,142, which is incorporated herein by reference.

Indexed rotational positioning of the elongated portion 150 of the present clamp coagulator instrument 120 may be provided by the provision of a detent mechanism incorporated into the clamp drive mechanism of the instrument 120. Specifically, the drive collar 200 may include a pair of axially spaced apart drive flanges 232. A detent-receiving surface may be provided between the drive flanges 232, and may define a plurality of circumferentially spaced teeth 234. The teeth 234 may define detent-receiving depressions generally about the periphery of the drive collar 200. In the embodiment illustrated in FIG. 7, twelve (12) of the teeth 234 are provided, thereby providing indexed positioning of the elongated portion 150 of the apparatus at 30° intervals relative to the housing 130 of the apparatus.

Indexed rotational movement may be further achieved by the provision of at least one, and preferably a pair, of diametrically opposed detents 236 respectively provided on cantilevered yoke arms 238 of the drive yoke 220. By this arrangement, the yoke arms 238 are positioned between the drive flanges 232 for engagement with the confronting surfaces thereof, and bias the detents 236 into engagement with the drive collar 200. Indexed relative rotation is thus achieved, with the detents 236 of the yoke arms 238 cooperating with the drive flanges 238 for effecting reciprocation of the actuating member 170. According to various embodiments, the drive yoke 220 may be formed from suitable polymeric material, with the biasing force created by the yoke arms 238 acting on the detents 236 thereof cooperating with the radial depressions defined by the drive collar to resist relative rotational torque less than about 5 to 20 inch-ounces. Accordingly, the elongated portion 150 of the clamp coagulator instrument 120 is maintained in any of its selected indexed rotational positions, relative to the housing 130, unless a torque is applied (such as by the rotation knob 216) exceeding this predetermined torque level. A snap-like indexing action is thus provided.

Rotation of the elongated proportion 150 of the present clamp coagulator instrument 120 may be effected together with relative rotational movement of ultrasonic drive unit 50 with respect to housing 130. In order to join the elongated portion 150 to the ultrasonic drive unit 50 in ultrasonic-transmitting relationship, the proximal portion of the outer tubular sheath 160 may be provided with a pair of wrench flats 240 (FIG. 3). The wrench flats allow torque to be applied by a suitable torque wrench or the like to thereby permit the end effector 180 to be joined to the ultrasonic drive unit 50. The ultrasonic drive unit 50, as well as the elongated portion 150, are thus rotatable, as a unit, by suitable manipulation of the rotation knob 216, relative to the housing 130 of the apparatus. The interior of housing 130 is dimensioned to accommodate such relative rotation of the drive unit 50.

Figure 9:
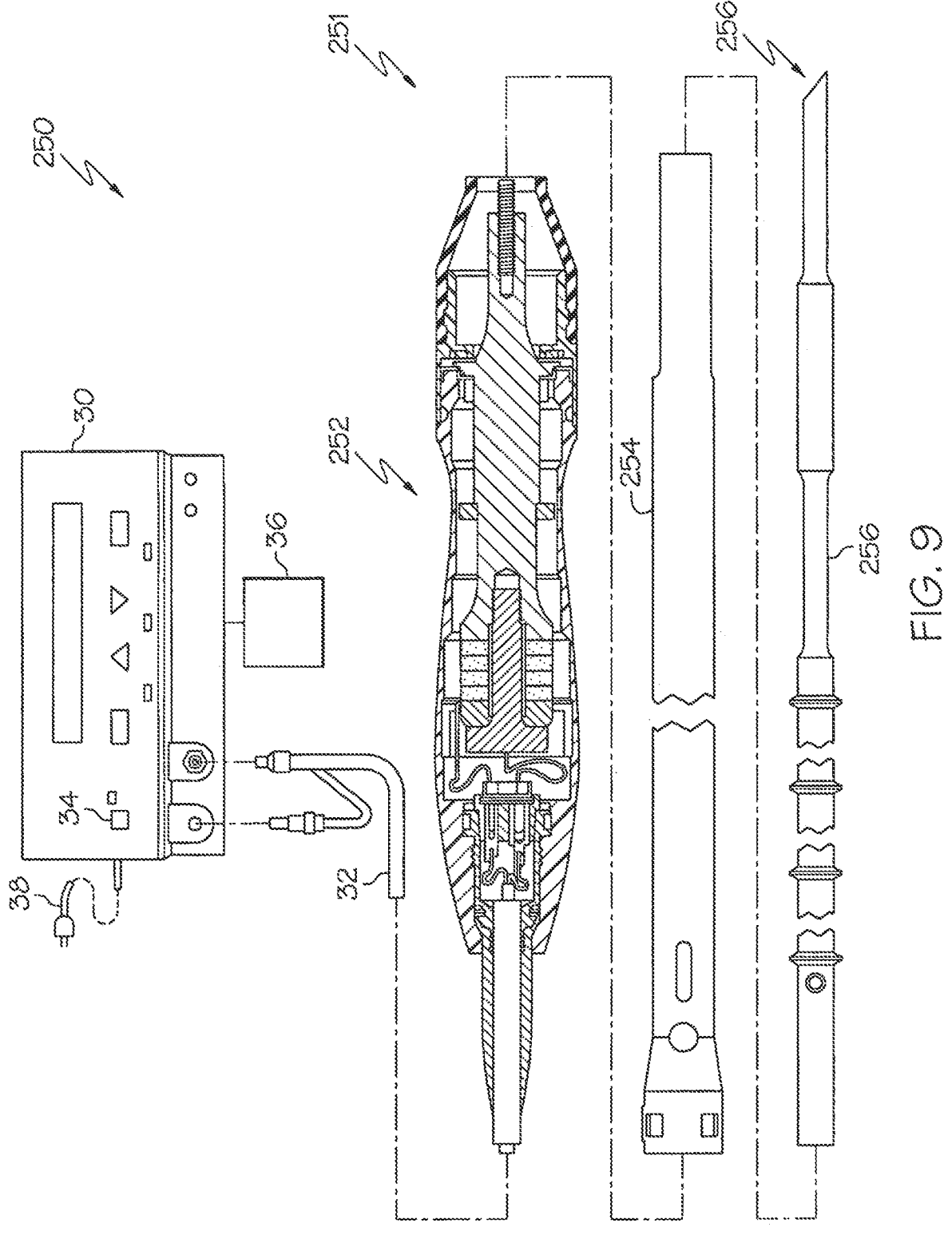
FIG. 9 illustrates one embodiment of a surgical system including a surgical instrument having single element end effector.

FIG. 9 illustrates one embodiment of a surgical system 250 including a surgical instrument 251 having single element end effector 256. The system 250 may include a transducer assembly 252 coupled to the end effector 256 and a sheath 254 positioned around the proximal portions of the end effector 256 as shown. The transducer assembly 252 and end effector 256 may operate in a manner similar to that of the transducer assembly 50 and end effector 180 described above to produce ultrasonic energy that may be transmitted to tissue via a blade 256'.

Figure 10:
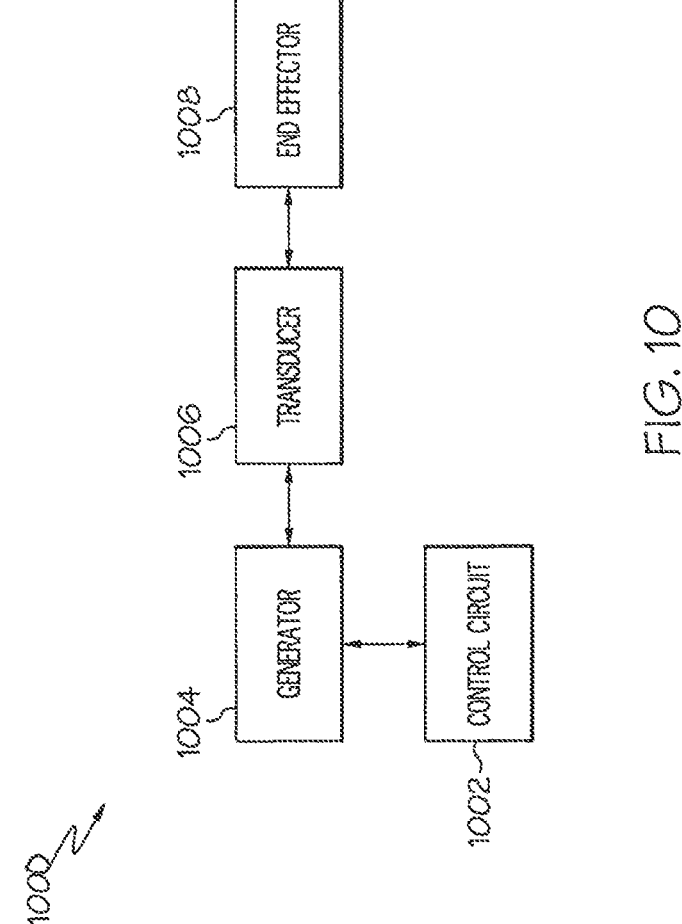
FIG. 10 illustrates a block diagram of one embodiment of a surgical device.

FIG. 10 illustrates a block diagram of one embodiment of a surgical device 1000, which may be configured with temperature feedback functionality. For example, the control circuit 1002 may adjust a current amplitude of an electrical signal provided by the generator 1004 to the transducer 1006 in response to changes in a vibration frequency of the end effector 1008. According to various embodiments, when the vibration frequency of the end effector 1008 drops, the amplitude of the electrical signal may be reduced. This may allow the surgical device 1000 to maintain the end effector 1008 at a relatively constant temperature and, thus give the device 1000 more uniform performance.

During surgical procedures, the end effector 1008 may be brought into contact with tissue and vibrated to cut and/or coagulate the tissue, as described above. When this occurs, friction between the end effector 1008 and the tissue may cause the temperature of the end effector 1008 to rise. As the temperature of the end effector 1008 rises, its material properties may change, causing changes to the device 1000 as a whole. For example, as the temperature of the end effector 1008 rises, the relationship between the displacement of the end effector 1008 and the current amplitude of the electrical signal may change such that the displacement of the end effector 1008 increases without a corresponding increase in the current amplitude. Also, as the temperature of the end effector 1008 rises, the resonant vibration frequency of the end effector 1008 may be reduced. For example, the changed material properties of the end effector 1008 may reduce the resonant frequency of the device 1000. As a result, the generator 1004 may reduce the frequency of the electrical drive signal bringing about a parallel reduction in the driven vibration frequency of the end effector 1008.

The control circuit 1002 may monitor the electrical signal provided by the generator 1004. As described, a decrease in the frequency of the electrical signal may indicate an increase in the temperature of the end effector 1008 as well as an increase in its displacement. When the control circuit 1002 senses a decrease in the frequency of the electrical signal it may command the generator 1004 to reduce the current amplitude of the electrical signal. The current amplitude of the electrical signal may be reduced by an amount suitable to keep the frequency of the end effector 1008 substantially constant resulting in a substantially constant temperature of the end effector 1008. The amount of current amplitude change necessary to compensate for a given frequency change may be determined by any suitable experimental or theoretical method.

It will be appreciated that the device 1000 may be physically embodied as any suitable ultrasonic device or system including, for example, the systems 10 and 250 described above. The control circuit 1002 may be embodied as any suitable analog or digital circuit. For example, the control circuit 1002 may comprise a processor, for example, a digital signal processor (DSP).

In addition to, or instead of the temperature feedback functionality described above, one embodiment of the device 1000 shown in FIG. 10 may be configured to detect cavitation, wherein the acoustic cavitation signal is transferred from the tissue to the end effector 1008. This may provide the clinician with information regarding the state of the tissue. For example, before the tissue is desiccated, substantially all of the water present in the tissue may be removed, either by evaporation or boiling. As water is evaporated or boiled, it may generate cavitations in the tissue. Detecting the presence of these cavitations may allow the device 1000 to give the clinician an indication that the tissue is, or is about to be, desiccated. Other tissue transitions occurring during cutting and/or coagulation may be indicated by various other cavitations.

Tissue cavitations originating from tissue in contact with the end effector 1008 (and/or from fluid included within the tissue) may affect the vibration of the end effector 1008, and accordingly the electrical signal between the generator 1004 and the transducer 1006. As described above, the piezoelectric elements (not shown) may generate motion in response to an electrical charge. Also, piezoelectric elements may work in reverse and generate and/or modify an electrical charge in response to motion. Accordingly, tissue cavitations transferred to the end effector 1008 may be, in turn, transferred to the piezoelectric elements of the transducer 1006. This may cause the piezoelectric elements to generate charges that modify the electrical signal between the generator 1004 and the transducer 1006 in a manner proportional to the tissue cavitations. Isolating the portion of the electrical signal due to the tissue cavitations may indicate the presence of tissue cavitations, as well as their dominant frequency/frequencies, and other information.

The portion of the electrical signal due to tissue cavitation may be isolated in any suitable way. For example, the control circuit 1002 may include a filter circuit (not shown) to filter the drive frequency and any harmonics thereof from the electrical signal. The remaining components of the electrical signal may be due to tissue cavitation. The filter circuit may comprise any suitable analog or digital filter.

Many tissue cavitations are of a relatively short duration, and therefore have a relatively wide frequency content. Accordingly, the tissue cavitations may not be apparent at any distinct frequencies and may instead serve to excite the end effector 1008 at its resonant frequency (e.g., the vibration frequency) and the harmonics thereof. To handle this scenario, the control circuit 1002 may include a processor or other functionality to compare the electrical signal to a comparison electrical signal measured when the end effector 1008 is unloaded, or not in contact with tissue. Differences between the measured electrical signal and the comparison electrical signal may indicate the presence of tissue cavitations. When the control circuit 1002 senses the presence of tissue cavitations, it may communicate this to the clinician any suitable method including, for example, by using a light, a display and/or an audible signal.

Figure 11:
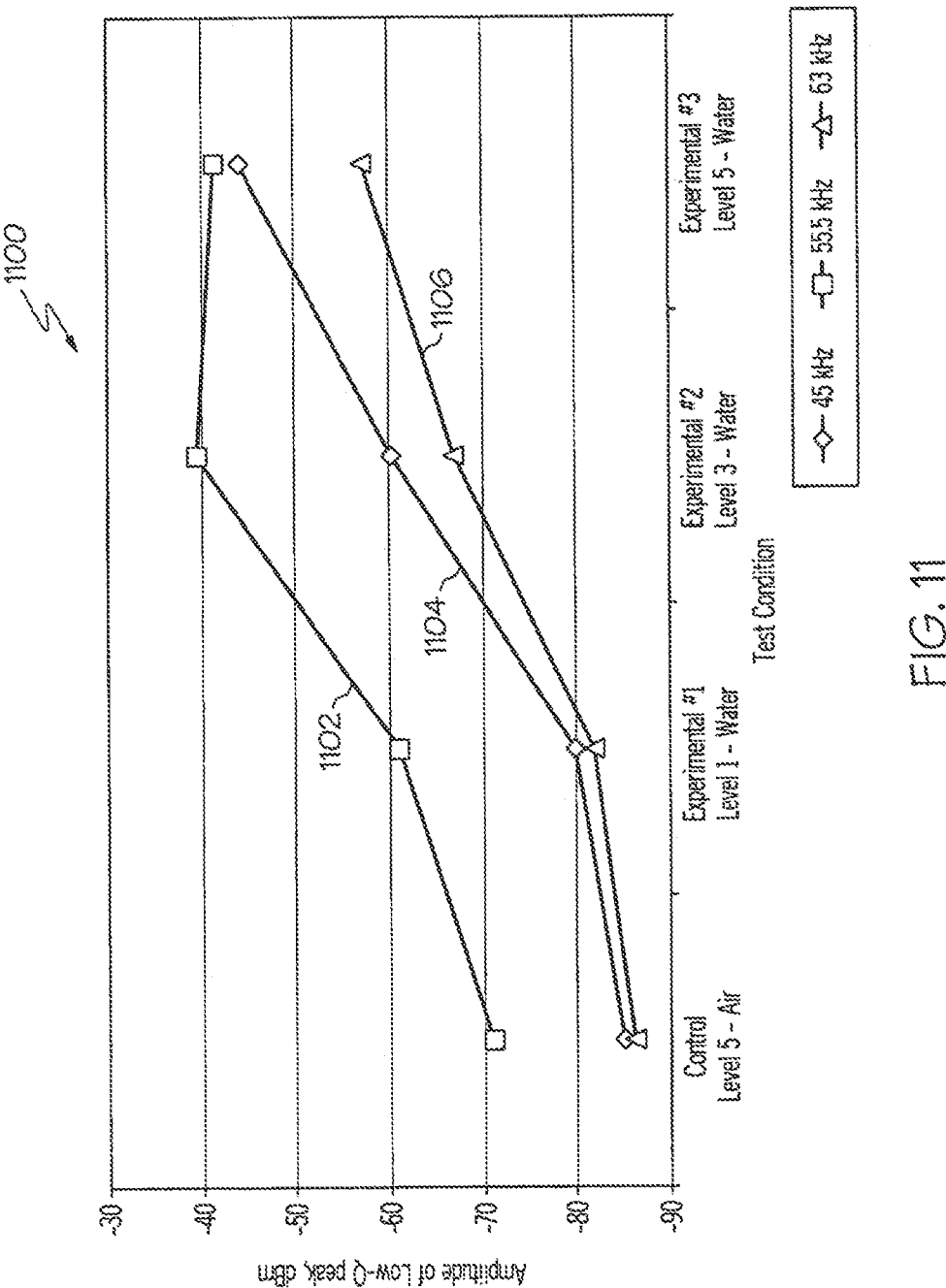
FIG. 11 shows a graph illustrating results of an example test of a surgical device.

FIG. 11 shows a graph 1100 illustrating results of an example test of one embodiment of a surgical device. In the example test, external cavitations are identified by analyzing the frequency content of an electrical signal between a transducer and an end effector. In the test, an LCS14C end effector was used in conjunction with a HP054 transducer and a GEN 300 generator operated at a nominal drive frequency of 55.5 kHz. All of these components are available from Ethicon Endo Surgery, Inc. A control trial was performed by energizing the end effector in air at a level 5 power setting for a period of 100 milliseconds. During this time, the electrical signal between the transducer and generator was monitored with an AGILENT Oscilloscope Model 5483D. For each experimental trial, the end effector was placed in a plastic beaker filled with 400 cc of fresh tap water. The end effector was then energized at a given power level for a period of 100 milliseconds while the electrical signal between the transducer and generator was monitored with the oscilloscope. Three experimental trials were run at generator settings of 1, 3 and 5 respectively.

The graph 1100 illustrates the amplitudes of low-Q peaks in the electrical signal observed during the control and experimental trials at the drive frequency and at two harmonics of the drive frequency. Line 1102 illustrates the drive frequency of 55.5 kHz, line 1104 illustrates a first harmonic at 45 kHz, and line 1106 illustrates a second harmonic at 63 kHz. It can be seen that the amplitude of the low-Q peak at the drive frequency was markedly higher during the experimental trials than during the control trial. Likewise, the amplitude of the low-Q peaks at the harmonics was higher during the experimental trials. It is believed that these increased amplitudes at the drive frequency 1102 and the harmonics 1104, 1106 were due to cavitations caused when dissolved gas in the tap water was released by the vibration of the end effector. In support of this conclusion, it is noted that when the tap water was not changed between trials, the low-Q peaks were significantly smaller, suggesting that all of the dissolved gas had been released. When the end effector encounters tissue cavitations, similar effects would be apparent in the low-Q peaks at the drive and harmonic frequencies of the device.

Figure 12:
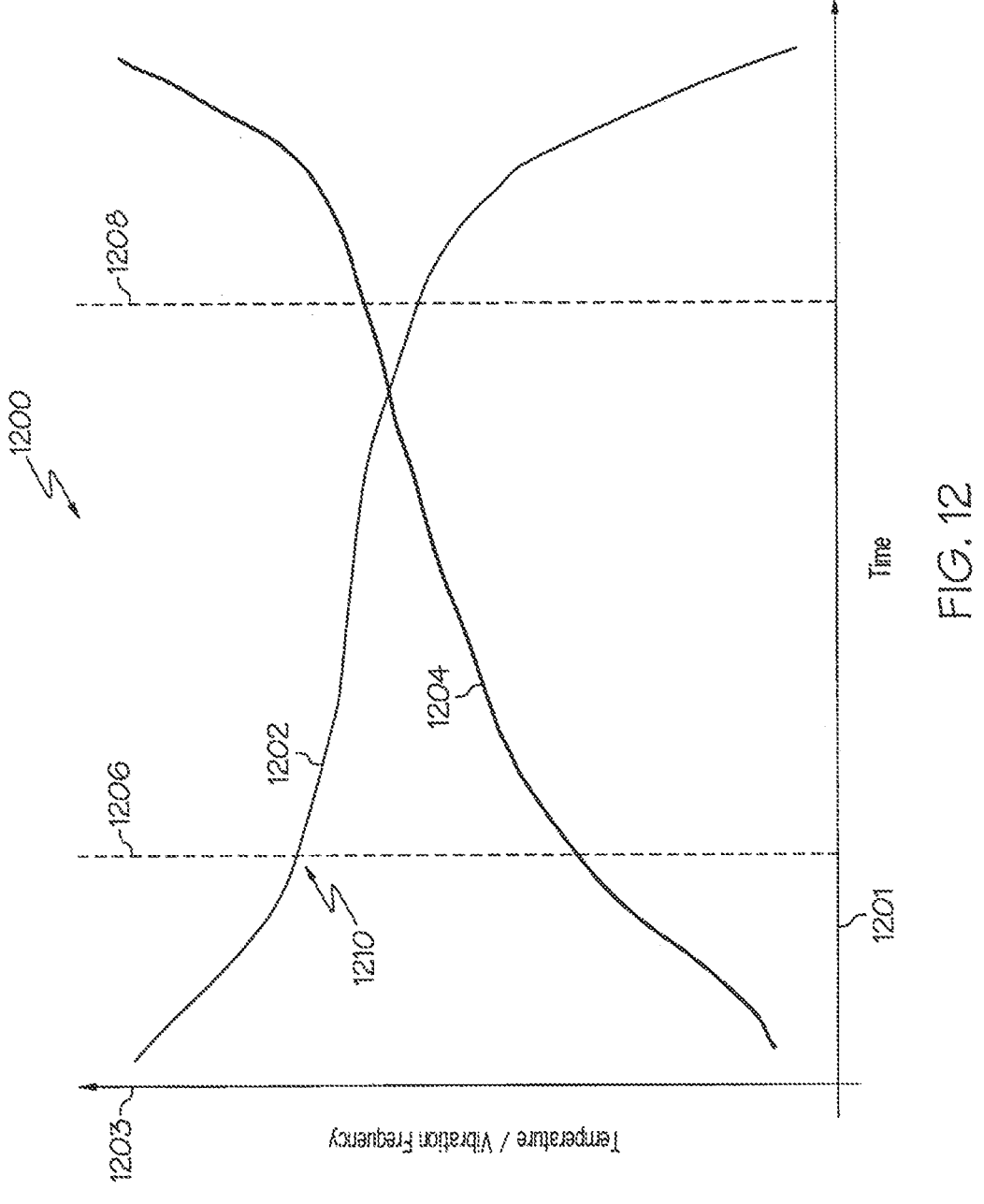
FIG. 12 shows a graph illustrating a relationship between end effector frequency and end effector temperature.

In addition to, or instead of the functionality described above, the device 1000 shown in FIG. 10 may have functionality for monitoring changes in the frequency of the end effector 1008. For example, the control circuit 1002 may monitor the vibration frequency of the end effector to detect changes. Changes in end effector frequency may indicate changes in tissue that is in contact with the end effector. FIG. 12 shows a chart 1200 illustrating a relationship between end effector frequency 1202 and end effector temperature 1204 over the coagulation and cutting process. The horizontal axis 1201 represents time while the vertical axis 1203 represents temperature with respect to the curve 1204 and end effector vibration frequency with respect to the curve 1202. The vertical line 1206 represents the approximate beginning of tissue coagulation (e.g., the denaturing of collagen described above). Vertical line 1208 represents the approximate beginning of desiccation and incipient transection.

Over the course of the cutting/coagulation process shown in chart 1200, the temperature curve 1204 increases. Prior to the beginning of coagulation 1206, the temperature curve 1204 increases sharply. Between coagulation 1206 and desiccation 1208, the increase in the slope of the temperature versus time curve 1204 is reduced. After desiccation 1208, the temperature curve 1204 again begins to increase more rapidly. The end effector frequency curve 1202 may mirror the temperature curve 1204. For example, the frequency curve 1202 may decrease rapidly prior to the beginning of coagulation 1206. At the beginning of coagulation 1206, the frequency curve 1202 continues to decrease, but does so less rapidly, demonstrating a knee feature 1210. At around the onset of desiccation 1208, the frequency curve 1208 may begin to decrease more rapidly.

According to various embodiments, the control circuit 1002 may be programmed to recognize the changes in the rate of decrease in the frequency curve 1202 to derive an indication of when tissue has begun to coagulate, and when it has begun desiccation. In one embodiment, the control circuit 1002 may monitor the vibration frequency of the end effector 1008 by monitoring the frequency of the electrical signal between the generator 1004 and transducer 1006. It will be appreciated that these two frequencies may be the same. When the control circuit 1002 senses that the rate of decrease of the end effector frequency has declined (e.g., the curve 1202 has reached the knee feature 1210), the control circuit 1002 may generate an indication that coagulation has begun. When the control circuit 1002 senses that the rate of decrease of the end effector frequency has again increased, it may indicate the beginning of desiccation. The various indications may be communicated to the clinician by the device 1000 according to any suitable method including, for example, a light, a display and an audible signal. According to various embodiments, the control circuit 1002 may de-energize the end effector 1008, or reduce its amplitude of vibration, in response to a transition to coagulation or to desiccation. This may allow the clinician to inspect the tissue before coagulation and/or desiccation to ensure that the procedure is proceeding satisfactorily.

According to various embodiments, the device 1000 of FIG. 10 may combine frequency change functionality with tissue cavitation sensing functionality to indicate the state of tissue in contact with the end effector 1008. For example, although the frequency curve 1202 shown in FIG. 12 illustrates a knee feature 1210 at the onset of coagulation 1206, its rate of frequency change may transition more gradually at the onset of desiccation 1208. Accordingly, it may be difficult to accurately identify the onset of desiccation 1208 by monitoring the end effector frequency alone. Tissue cavitations, on the other hand, are most common at about the onset of desiccation 1208. For example, as water is evacuated from the tissue, it may boil violently, causing cavitations. Accordingly, the control circuit 1002 may be configured to identify the onset of coagulation 1206 by identifying the knee 1210 in the end effector frequency curve 1202, as described above. Also, the control circuit 1002 may be configured to identify the onset of desiccation 1208 by identifying tissue cavitations, for example, in conjunction with an increase in the rate of reduction of the end effector frequency curve 1202. Again, the various indications may be communicated to the clinician by the device 1000 according to any suitable method including, for example, a light, a display and an audible signal. Also, the device 1000 may be de-energized, or the vibration frequency of the end effector 1008 reduced, upon a transition to coagulation or desiccation, as described above.

Figure 13:
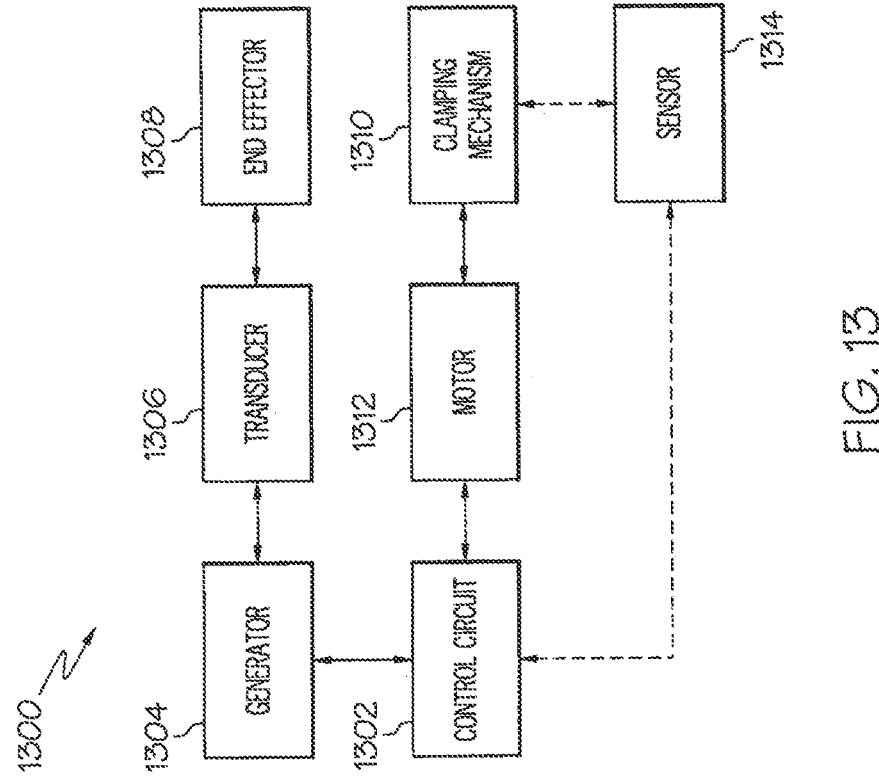
FIG. 13 illustrates a block diagram of one embodiment of a surgical device.

FIG. 13 illustrates a block diagram of one embodiment of a surgical device 1300 configured to derive end effector feedback considering a coefficient of collagen denaturation (CCD). The CCD may represent an amount of friction between the end effector 1308 and a portion of tissue (not shown). Analysis of a CCD curve taken over the course of a cutting and/or coagulation procedure may provide information about the progress of the cutting and coagulation as well as information about the tissue portion including, for example, its thickness and outside diameter.

According to various embodiments, the CCD may be calculated as a function of variables, for example, including: (i) power provided to the end effector 1308; (ii) the vibration frequency of the end effector 1308; (iii) the displacement of the end effector 1308 over a cycle; and (iv) a clamp force applied to the region of tissue between the clamping mechanism 1310 and the end effector. The clamping mechanism 1310 itself may be any suitable mechanism for clamping or otherwise exerting a force on the tissue region against the end effector. According to various embodiments, the clamping mechanism 1310 may be similar to the clamping mechanism 190 described above. Values for the above variables over time may be found by the control circuit 1302 of the device 1300. For example, the power provided to the end effector 1308 may be found by considering the electrical signal between the generator 1304 and the transducer 1306 while the end effector 1308 is under load (e.g., in contact with the region of tissue). The displacement per cycle of the end effector 1308 may be a function of the current amplitude of the electrical signal. Also, as described above, the vibration frequency of the end effector 1308 may be substantially similar to that of the electrical signal.

The clamp force of the end effector 1308 and clamping mechanism 1310 may be found according to any suitable method. For example, according to various embodiments, the clamping mechanism 1310 may be driven by an electric motor. For example, referring to the embodiment shown in FIG. 2, the reciprocal actuating member 170 may be translated distally and proximally by the motor 1312. In this embodiment, the clamping force between the clamping mechanism 1310 and the end effector 1308 may be derived from a drive electrical signal provided to the motor 1312. For example, the current amplitude of the drive electrical signal may indicate the clamping force. According to various embodiments, the clamp force may be derived from a sensor 1314 in communication with the control circuit 1302. The sensor may be placed at any suitable location in communication with the end effector 1308, clamping mechanism 1310 and/or a portion of the device handpiece (not shown in FIG. 13). The embodiment shown in FIG. 4 illustrates one example of a sensor 1316 positioned between the clamp arm tissue pad 192 and clamp arm 190. Also, the embodiment shown in FIG. 2 illustrates a sensor 1318 positioned between a portion of the operating lever 222 and drive collar 200. In one embodiment, the clamp force may be considered a constant and factored into the CCD calculations as such.

Figure 14:
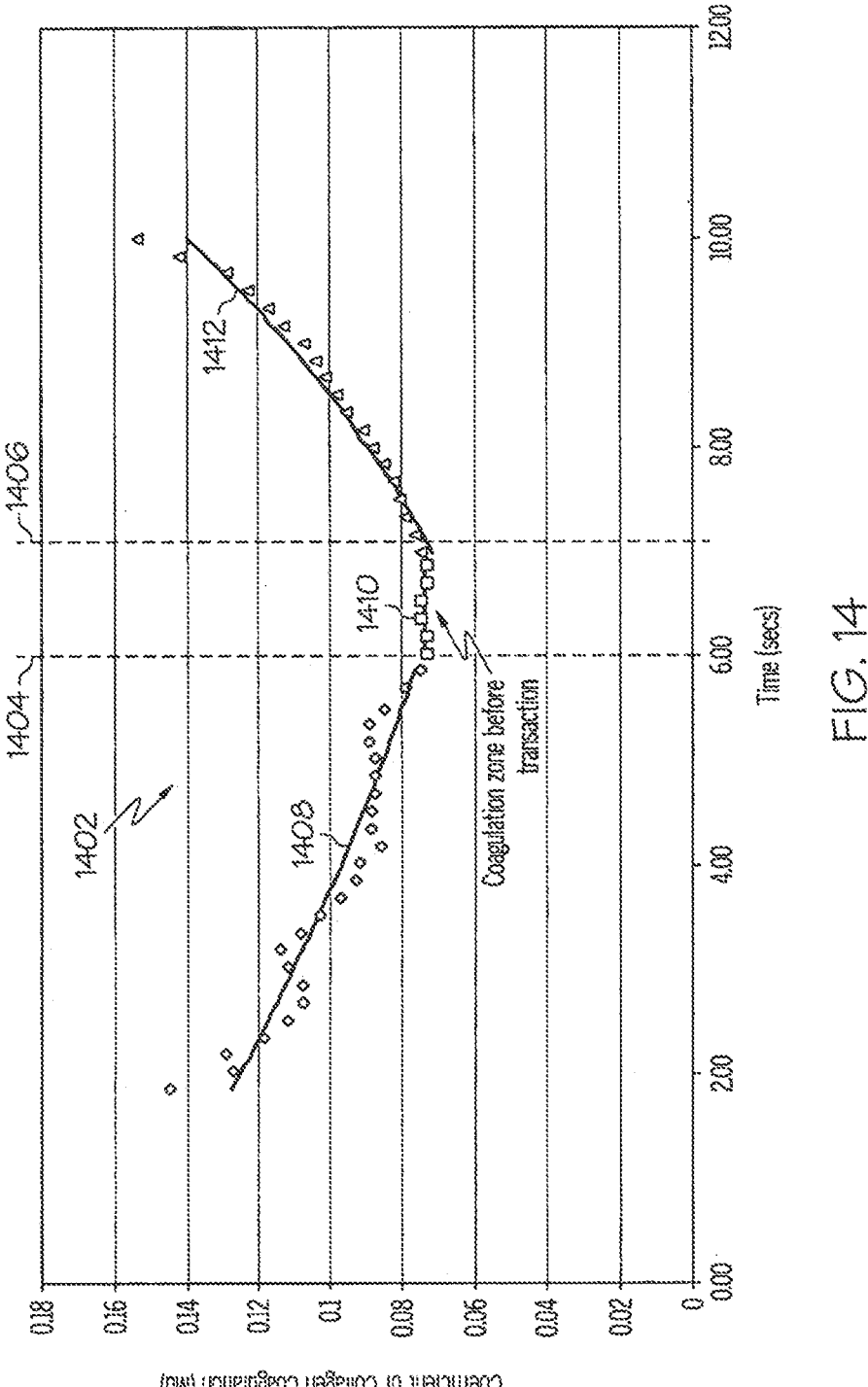
FIG. 14 shows a graph illustrating a coefficient of collagen denaturation curve.

The device 1300 may utilize the CCD curve to sense when the portion of tissue enters the coagulation and desiccation stages. FIG. 14 shows a graph illustrating a CCD curve 1402 over a full coagulating and cutting transaction. The CCD curve 1402 was derived with an ultrasonic instrument having a solid core end effector powered by a GEN03 generator device available from Ethicon Endo Surgery, Inc. The power of the generator was set to level three (3); the end effector 1408 displacement was set to 55 microns; the end effector vibration frequency was configured at 55.5 kHz; and a clamping force of 2 pounds was utilized. The curve 1402 may be divided into three regions. A first region 1408 may correspond to times before the onset of coagulation 1404 and may have a substantially negative slope. A second region 1410 may correspond to times between the onset of coagulation 1404 and the onset of desiccation 1406 and may have a substantially neutral slope. A third region 1412 may correspond to times after the onset of desiccation 1406 and may have a substantially positive slope. According to various embodiments, the control circuit may monitor the slope of the CCD curve 1402 to determine the state of the tissue portion. Transitions to coagulation or to desiccation may be indicated to the clinician according to any suitable method including, for example, a light, a display and/or an audible signal. Also, as described, the control circuit 1302 may de-energize the end effector 1308 in response to a transition to coagulation or to desiccation.

Figure 15:
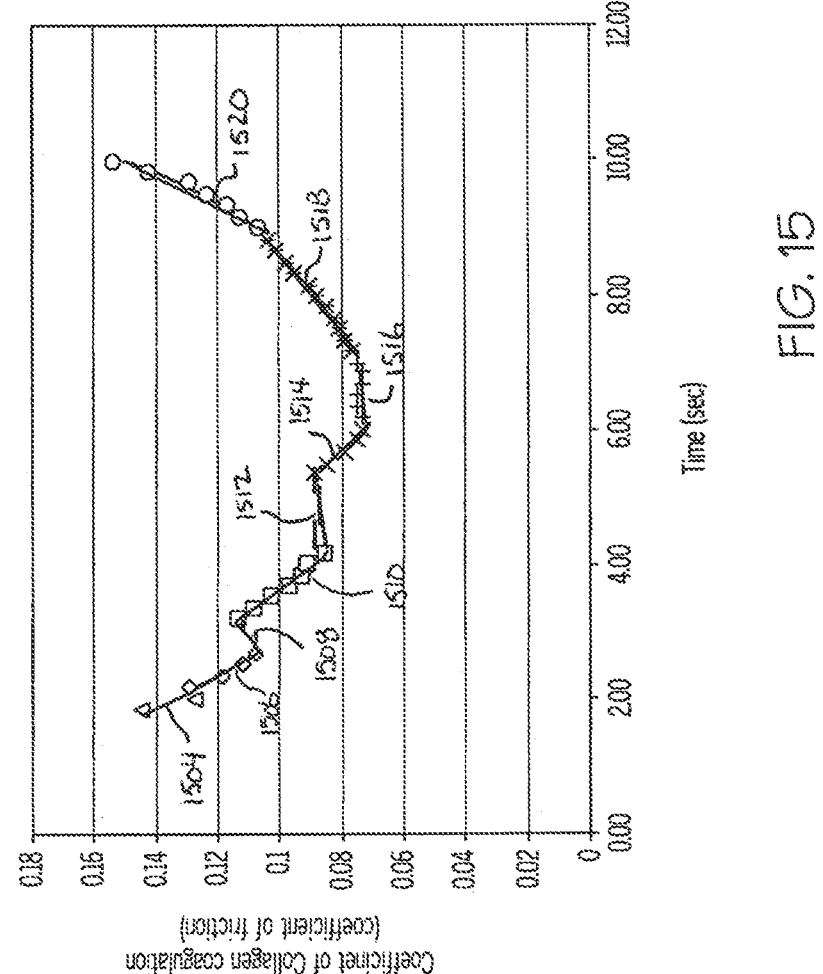
FIG. 15 shows a graph illustrating a coefficient of collagen denaturation curve.

The CCD curve 1402 also may be utilized by the control circuit 1302 to determine other features of the tissue portion including, for example, its outside diameter and thickness. It will be appreciated that the tissue portion may be a solid portion of tissue, or may define a lumen (e.g., an artery, vein or other tubular tissue time). FIG. 15 shows a graph illustrating a coefficient of collagen denaturation curve 1502. The curve 1502 was derived over the coagulation and desiccation of a Carotid artery utilizing an ultrasonic instrument having a solid core end effector powered by a GEN03 generator device. The power of the generator was set to level five (5). The end effector 1408 displacement was set to 55 microns; the end effector vibration frequency was configured at 55.5 kHz; and a clamping force of 2 pounds was utilized. The CCD curve 1502 has been broken into nine regions 1504, 1506, 1508, 1510, 1512, 1514, 1516, 1518 and 1520 having a substantially constant slope.

Various properties of each of the nine regions of the CCD curve 1402 may correlate to properties of the tissue portion such as the outer diameter and thickness. In one example experiment, fourteen carotid arteries of various diameters were coagulated and cut with an ultrasonic instrument having a solid core end effector powered by a GEN03 generator device. Table 1 below shows the Outside Diameter and Wall Thickness of the carotid arteries as well as the Clamp Force and Power Level used. The Polynomial Fit column lists the exponent of the polynomial fit to the first region 1504 of the CCD curve for each trial. The Normalized CCD value shows the CCD value for each trial normalized by dividing each individual CCD value by the CCD value at the end of the first region 1504.

TABLE 1

| Trial | Clamp Force | Power Level | Outside Diameter (in.) | Wall Thickness | Polynomial Fit | Normalized CCD Value |
|---|---|---|---|---|---|---|
| 1 | 0.4 | 3 | 0.169 | 0.042 | .0181 | 1.2826 |
| 2 | 1 | 3 | 0.169 | 0.042 | 0.254 | * |
| 3 | 0.4 | 5 | 0.117 | 0.04 | 0.227 | * |
| 4 | 1 | 5 | 0.117 | 0.04 | 0.251 | * |
| 5 | 0.4 | 4 | 0.146 | 0.042 | 0.251 | 1.16738 |
| 6 | 1 | 4 | 0.146 | 0.042 | 0.361 | 1.47 |
| 7 | 0.4 | 4 | 0.136 | 0.05 | 0.266 | 1.14 |
| 8 | 1 | 4 | 0.136 | 0.05 | 1.231 | 1.23 |
| 9 | 0.7 | 3 | 0.094 | 0.045 | 1.765 | 1.05 |
| 10 | 0.7 | 5 | 0.094 | 0.045 | 0.744 | 1.35 |
| 11 | 0.7 | 3 | 0.156 | 0.045 | 0.15 | 1.1 |
| 12 | 0.7 | 5 | 0.156 | 0.045 | 0.214 | 1.49 |
| 13 | 0.7 | 4 | 0.119 | 0.035 | 0.791 | 1.27 |
| 14 | 0.7 | 4 | 0.119 | 0.035 | 0.295 | 1.23 |

Figure 16:
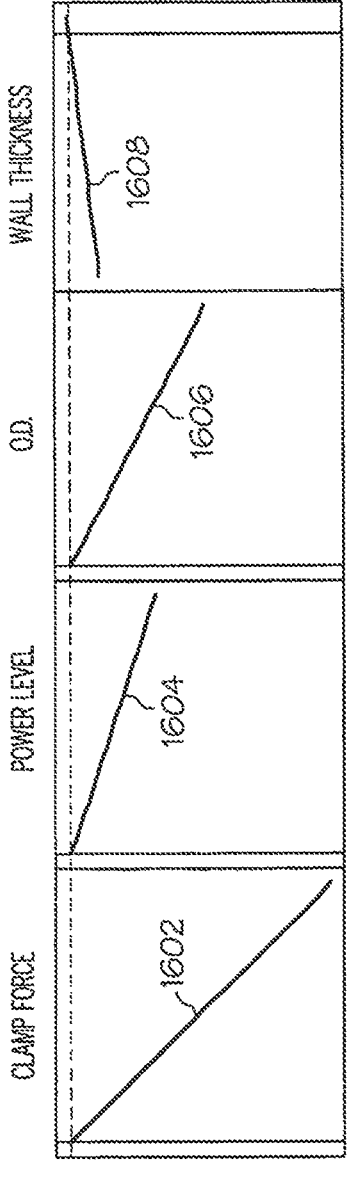
FIG. 16 shows a series of curves illustrating relationships between a normalized value of a first region of a coefficient of collagen denaturation curve and clamp force, power level, outside diameter and wall thickness.

FIG. 16 shows a series of curves 1602, 1604, 1606, 1608 illustrating relationships between the normalized value of the first point of the first region of the CCD curve clamp force, power level, outside diameter and wall thickness for the trials shown in Table 1. The degree of the slope of the curves 1602, 1604, 1606, 1608 may indicate the degree of correlation between the corresponding variable and the normalized value of the first point of the first region of the CCD curve. It can be seen that all of the curves 1602, 1604, 1606 and 1608 have non-zero slopes, and therefore all of their corresponding variables are correlated to the CCD curve. A mathematical model, such as a quadratic model, may be fit to the results of trials, such as those shown in Table 1, to derive one or more equations relating the normalized value of the first point of the first region of the CCD curve, the clamp force, the power level, outside diameter and wall thickness.

Referring back to the embodiment shown in FIG. 13, the control circuit 1302 may monitor a CCD curve generated as the device 1300 coagulates and/or cuts the tissue portion. Upon identifying a region of the CCD curve having a substantially similar slope, the control circuit 1302 may derive a property describing the region including, for example, a slope of the region, a normalized value of the curve in the region and/or a length of the first region. The control circuit 1302 may then derive a property of the tissue portion including, for example an outside diameter of the tissue portion or a thickness of the tissue portion. The tissue properties may be derived according to any suitable method. For example, mathematical models relating region properties to tissue properties may be developed, for example, as described above. The control circuit 1302 may utilize a predetermined mathematical model to relate the region property and tissue property. Also, according to various embodiments, look-up tables may be generated relating region properties to tissue properties.

Figure 17:
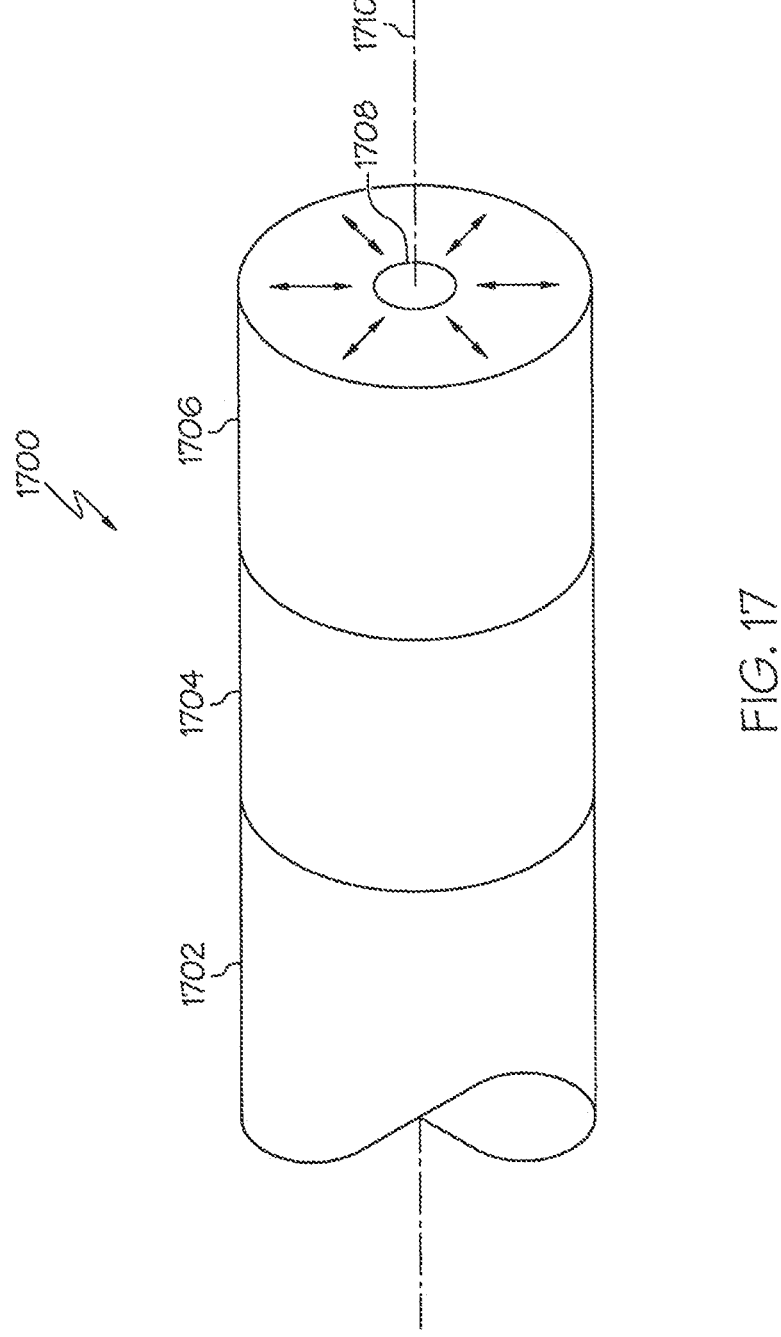
FIG. 17 illustrates one embodiment of an end effector for a surgical device including radial mode transducers.

FIG. 17 illustrates one embodiment of an end effector 1700 for a surgical device including radial mode transducers 1702, 1704, 1706. When excited by an electrical signal (e.g., from a generator) the radial mode transducers 1702, 1704, 1706 may generate ultrasonic vibrations perpendicular to a longitudinal axis 1710. The ultrasonic vibrations may have anti-nodes at the radial surfaces of the transducers 1702, 1704, 1706. As a result, the entire radial surface of the end effector 1700 may be active for coagulating and cutting tissue. A central member 1708 may extend along the longitudinal axis 1710 and may serve as an electrode for some or all of the radial mode transducer 1702, 1704, 1706. Additionally the outer radial surface of the radial mode transducers 1702, 1704, 1706 may be coated with an electrically conductive substance or alternatively may be enclosed in a metal tubular sheath, either of which may serve as an electrode. Although multiple transducers 1702, 1704, 1706 are shown, it will appreciated that some embodiments may include only one radial mode transducer.

Figure 18:
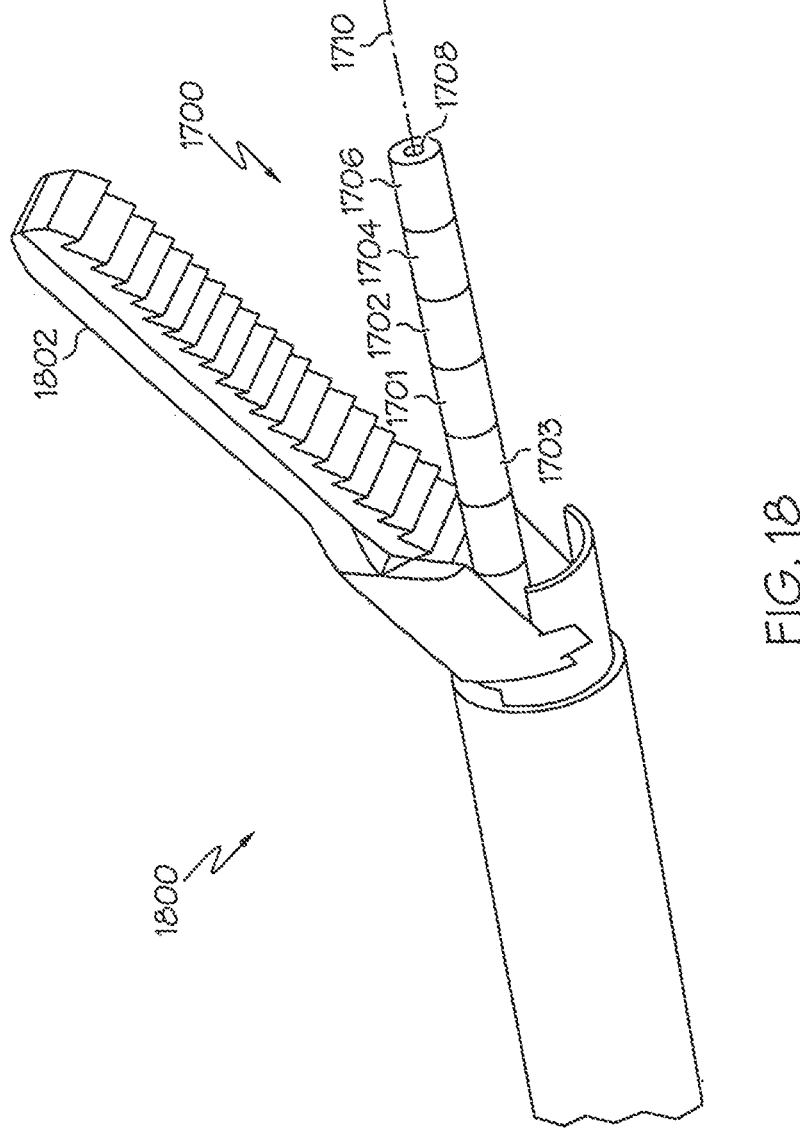
FIG. 18 illustrates one embodiment of the end effector of FIG. 17 installed on a surgical instrument including a clamp arm.
Figure 19:
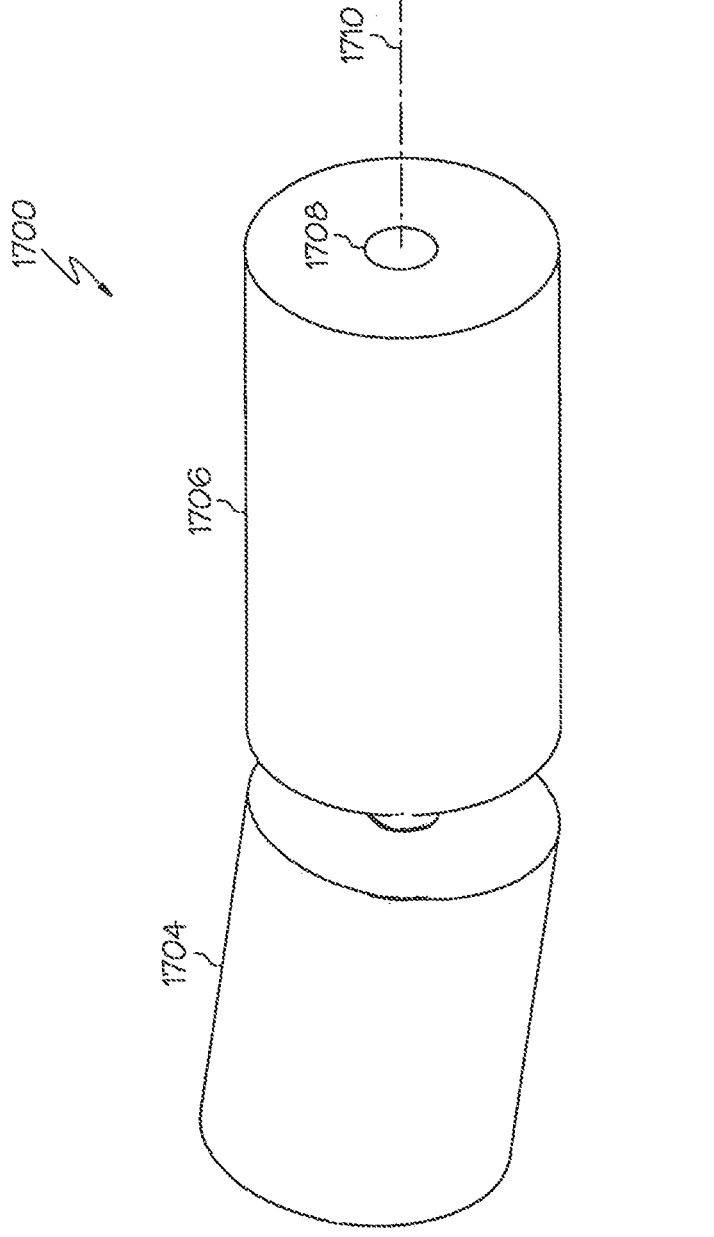
FIG. 19 illustrates one embodiment of the end effector of FIG. 17 including a flexible central member.

FIG. 18 illustrates one embodiment of the end effector 1700 of FIG. 17 installed on a surgical instrument 1800 including a clamp arm 1802. Additional radial mode transducers 1701 and 1703 are shown, although it will be appreciated that any suitable number b the different radial mode transducers, here 1706 and 1704, to flex relative to one another leading to a flexible and articulatable end effector 1700. Articulation of the end effector 1700 may be brought about in any suitable manner. For instance, the flexible central member 1708 may define a central lumen (not shown). Metal wires (not shown) may run within the central member 1708 on opposing sides of the central lumen. An articulation knob or other articulate implement near a handle portion of the instrument may be used to retract one of the metal wires. When a metal wire is retracted, it may cause the flexible central member 1708, and therefore the end effector 1700 to articulate in the direction of the retracted wire. For example, if a wire on the right side of the central member 1708 is retracted, then the end effector 1700 may articulate to the right. It will be appreciated that this is but one example of an articulation mechanism and that any suitable articulation method may be used.

Figure 20:
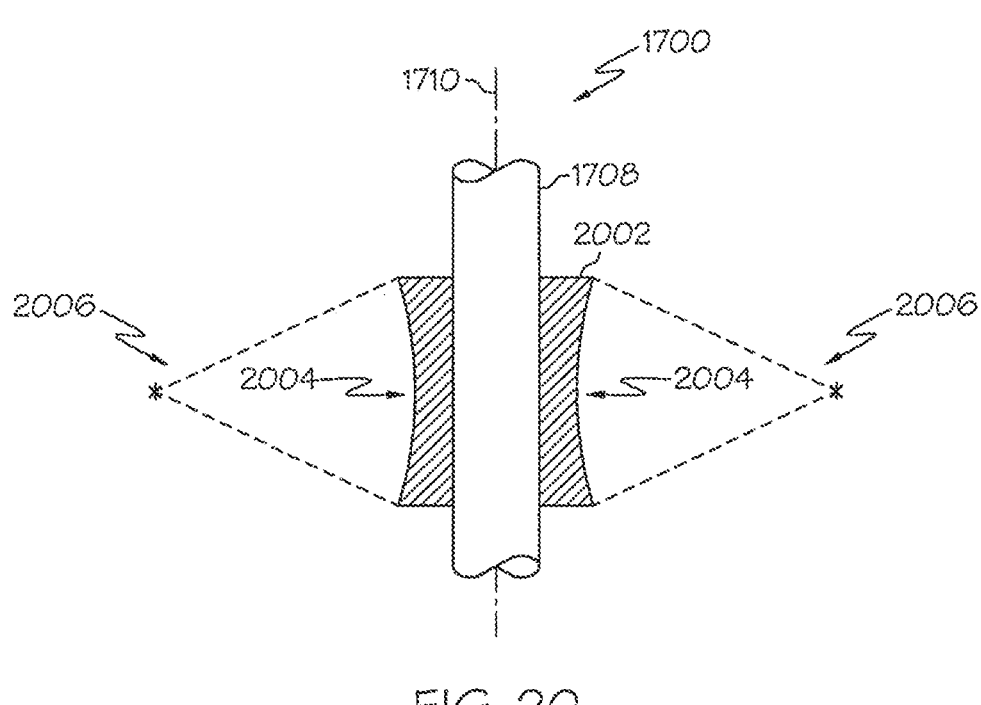
FIG. 20 illustrates one embodiment of the end effector of FIG. 17 including a transducer defining a concavity.
Figure 21:
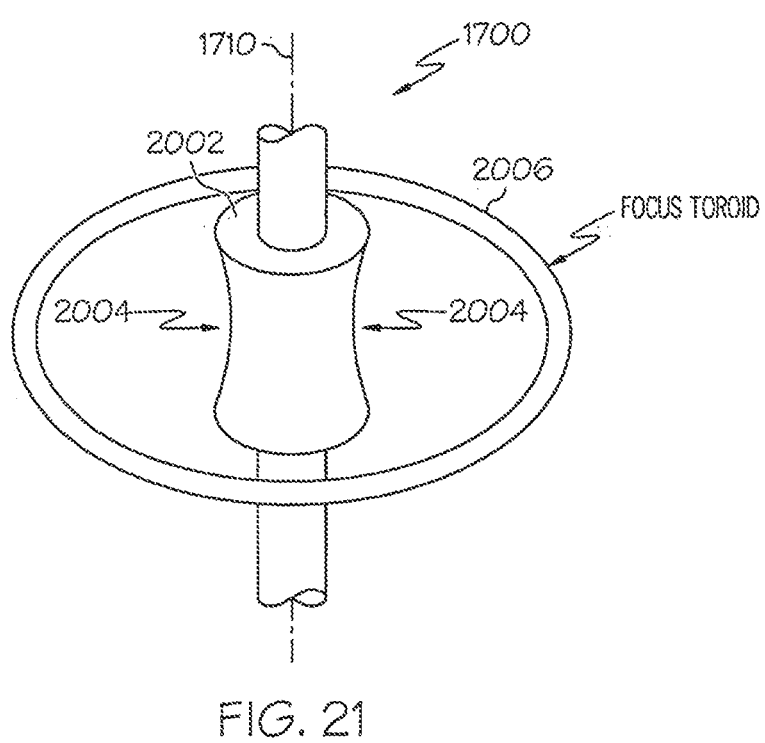
FIG. 21 illustrates one embodiment of the end effector of FIG. 20.

FIGS. 20-21 illustrate one embodiment of the end effector 1700 of FIG. 17 including a transducer 2002 defining a concavity 2004. The transducer 2002 may utilize the concavity 2004 to direct ultrasonic energy to tissue that is not in direct physical contact with the transducer 2002 or the end effector 1700. For example, the concavity of the transducer 2002 may serve to focus ultrasonic energy to points 2006. According to various embodiments, the concavity 2004 may extend radially around the transducer 2002, as shown in the embodiment of FIG. 21. Accordingly, the focal point 2006 extends radially around the transducer 2002 forming a toroid.

The devices disclosed herein can be designed to be disposed of after a single use, or they can be designed to be used multiple times. In either case, however, the device may be reconditioned for reuse after at least one use. Reconditioning can include any combination of the steps of disassembly of the device, followed by cleaning or replacement of particular elements, and subsequent reassembly. In particular, the device may be disassembled, and any number of particular elements or components of the device may be selectively replaced or removed in any combination. Upon cleaning and/or replacement of particular components, the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Preferably, the various embodiments described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized prior to surgery. This can be done by any number of ways known to those skilled in the art including beta or gamma radiation, ethylene oxide, steam.

Although various embodiments have been described herein, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A surgical device comprising:
a transducer to receive an electrical signal from a generator and to provide vibrations;
an end effector coupled to the transducer and extending from the transducer along the longitudinal axis; and
a control circuit to modify a current amplitude of the electrical signal in response to a change in a vibration frequency of the end effector.

2. The surgical device of claim 1, wherein the change in vibration frequency comprises a reduction in the vibration frequency of the end effector, and wherein to modify the current amplitude of the electrical signal comprises to reduce the amplitude of the electrical signal.

3. The surgical device of claim 1, wherein the change in the vibration frequency of the end effector comprises a reduction in a rate of decrease of the vibration frequency of the end effector.

4. The surgical device of claim 1, wherein the change in the vibration frequency of the end effector corresponds to a tissue condition of tissue captured by the end effector.

5. The surgical device of claim 4, wherein the tissue condition comprises a temperature of the tissue captured by the end effector and wherein the change in vibration frequency comprises a reduction in the vibration frequency of the end effector, and
wherein to modify the current amplitude of the electrical signal comprises to reduce the amplitude of the electrical signal.

6. The surgical device of claim 5, wherein to reduce the amplitude of the electrical signal comprises to reduce the amplitude of the electrical signal until the vibration frequency of the end effector is at a constant value.

7. A computer readable medium comprising instructions that when executed by a processor cause the processor to:

monitor an electrical signal provided to a transducer of a surgical instrument, wherein the transducer is coupled to an end effector;
monitor a vibration frequency of the end effector;
modify an amplitude of the electrical signal in response to a change in the vibration frequency.

8. The computer readable medium of claim 7, wherein the change in vibration frequency comprises a reduction in the vibration frequency of the end effector, and wherein to modify the current amplitude of the electrical signal comprises to reduce the amplitude of the electrical signal.

9. The computer readable medium of claim 7, wherein the change in the vibration frequency of the end effector comprises a reduction in a rate of decrease of the vibration frequency of the end effector.

10. The computer readable medium of claim 7, wherein the change in the vibration frequency of the end effector corresponds to a tissue condition of tissue captured by the end effector.

11. The computer readable medium of claim 10, wherein the tissue condition comprises a temperature of the tissue captured by the end effector and wherein the change in vibration frequency comprises a reduction in the vibration frequency of the end effector, and
wherein to modify the current amplitude of the electrical signal comprises to reduce the amplitude of the electrical signal.

12. The computer readable medium of claim 11, wherein to reduce the amplitude of the electrical signal comprises to reduce the amplitude of the electrical signal until the vibration frequency of the end effector is at a constant value.

13. A surgical device comprising a processor, wherein the processor is programmed to:
monitor an electrical signal provided to a transducer of a surgical instrument, wherein the transducer is coupled to an end effector;
monitor a vibration frequency of the end effector; and
modify an amplitude of the electrical signal in response to a change in the vibration frequency.

14. The surgical device of claim 13, wherein the change in vibration frequency comprises a reduction in the vibration frequency of the end effector, and wherein to modify the current amplitude of the electrical signal comprises to reduce the amplitude of the electrical signal.

15. The surgical device of claim 13, wherein the change in the vibration frequency of the end effector comprises a reduction in a rate of decrease of the vibration frequency of the end effector.

16. The surgical device of claim 13, wherein the change in the vibration frequency of the end effector corresponds to a tissue condition of tissue captured by the end effector.

17. The surgical device of claim 16, wherein the tissue condition comprises a temperature of the tissue captured by the end effector and wherein the change in vibration frequency comprises a reduction in the vibration frequency of the end effector, and
wherein to modify the current amplitude of the electrical signal comprises to reduce the amplitude of the electrical signal.

18. The surgical device of claim 17, wherein to reduce the amplitude of the electrical signal comprises to reduce the amplitude of the electrical signal until the vibration frequency of the end effector is at a constant value.

* * * * *